United States Patent
Sahin et al.

(10) Patent No.: US 11,713,346 B2
(45) Date of Patent: Aug. 1, 2023

(54) CLAUDIN-18.2-SPECIFIC IMMUNORECEPTORS AND T CELL EPITOPES

(71) Applicants: BioNTech Cell & Gene Therapies GmbH, Mainz (DE); TRON—Translationale Onkologie an der Universitatsmedizin der Johannes Gutenberg-Universität Mainz Gemein-Nutzige GMBH, Mainz (DE)

(72) Inventors: Ugur Sahin, Mainz (DE); Ozlem Tureci, Mainz (DE); Petra Oehm, Mainz (DE); Tana Omokoko, Mainz (DE); Andrea Breitkreuz, Worms (DE); Karolina Anna Mroz, Wiesbaden (DE); Lisa Hebich, Kerzenheim (DE)

(73) Assignees: BioNTech Cell & Gene Therapies GmbH, Mainz (DE); TRON—Translationale Onkologie An Der Universitätsmedizin der Johannes Gutenberg-Universität Mainz Gemeinnützige GmbH, Mainz (DE)

( * ) Notice: Subject to any disclaimer, the term of this patent is extended or adjusted under 35 U.S.C. 154(b) by 672 days.

(21) Appl. No.: 15/572,919

(22) PCT Filed: May 9, 2016

(86) PCT No.: PCT/EP2016/060337
§ 371 (c)(1),
(2) Date: Nov. 9, 2017

(87) PCT Pub. No.: WO2016/180782
PCT Pub. Date: Nov. 17, 2016

(65) Prior Publication Data
US 2018/0282389 A1 Oct. 4, 2018

(30) Foreign Application Priority Data
May 11, 2015 (WO) ................ PCT/EP2015/060357

(51) Int. Cl.
*C07K 16/28* (2006.01)
*C07K 14/725* (2006.01)
*C07K 7/06* (2006.01)
*A61K 39/00* (2006.01)
*C07K 14/705* (2006.01)
*C07K 14/74* (2006.01)

(52) U.S. Cl.
CPC ...... *C07K 14/7051* (2013.01); *A61K 39/0011* (2013.01); *C07K 7/06* (2013.01); *C07K 14/705* (2013.01); *C07K 14/70521* (2013.01); *C07K 14/70539* (2013.01); *C07K 16/28* (2013.01); *A61K 2039/5158* (2013.01); *A61K 2039/572* (2013.01); *A61K 2039/575* (2013.01); *C07K 2317/34* (2013.01); *C07K 2317/56* (2013.01); *C07K 2317/565* (2013.01); *C07K 2317/622* (2013.01); *C07K 2317/73* (2013.01); *C07K 2317/76* (2013.01); *C07K 2319/02* (2013.01); *C07K 2319/03* (2013.01); *C07K 2319/035* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,728,114 B2 * | 6/2010 | Mach | A61P 17/00 530/388.15 |
| 8,425,902 B2 * | 4/2013 | Sahin | A61P 43/00 424/130.1 |
| 2009/0169547 A1 * | 7/2009 | Sahin | A61P 43/00 424/133.1 |
| 2014/0242701 A1 | 8/2014 | Shiku et al. | |

FOREIGN PATENT DOCUMENTS

| | | | | |
|---|---|---|---|---|
| JP | 2013521785 A | | 6/2013 | |
| WO | WO-2005113587 A2 * | | 12/2005 | .......... C07K 16/303 |
| WO | WO 2008/145338 A2 | | 12/2008 | |
| WO | WO 2011/113546 A1 | | 9/2011 | |
| WO | WO 2012/038055 A1 | | 3/2012 | |
| WO | WO-2013167259 A1 * | | 11/2013 | ......... C07K 16/3046 |
| WO | WO-2013174510 A1 * | | 11/2013 | ......... C07K 16/3046 |
| WO | WO 2014/075788 A1 | | 5/2014 | |
| WO | WO-2014146672 A1 * | | 9/2014 | ................ A61P 1/04 |
| WO | WO-2015028444 A1 * | | 3/2015 | .............. A61P 35/00 |
| WO | WO 2015/113576 | | 8/2015 | |
| WO | WO-2015150327 A1 * | | 10/2015 | ............. A61K 35/17 |
| WO | WO-2016008405 A1 * | | 1/2016 | ............. C07K 16/28 |
| WO | WO-2016123143 A1 * | | 8/2016 | ......... C07K 14/7051 |
| WO | WO 2016/180782 A1 | | 11/2016 | |

OTHER PUBLICATIONS

Harlow et al. (Antibodies, A Laboratory Manual, Cold Spring Harbor laboratory, 1988, pp. 37-47). (Year: 1988).*
Edwards et al. (J. Mol. Biol. (2003) 334, 103-118). (Year: 2003).*
Lloyd et al. (Protein Engineering, Design & Selection vol. 22 No. 3 pp. 159-168, 2009). (Year: 2009).*
Meyer et al. (British Journal of Haematology, 2018, 180, 808-820). (Year: 2018).*
Kofler et al. (Mol Ther. Apr. 2011; 19(4):760-7). (Year: 2011).*
Beatty et al., Cancer Immunol Res; 2(2); 112-20. 2013. (Year: 2013).*
Chmielewski et al., OncoImmunology 1:8, 1387-1389; Nov. 2012. (Year: 2012).*
Schuberth et al. (Journal of Translational Medicine 2013, 11:187). (Year: 2013).*

(Continued)

*Primary Examiner* — Zachary S Skelding
(74) *Attorney, Agent, or Firm* — Neal, Gerber & Eisenberg LLP

(57) ABSTRACT

The present invention provides Claudin-18.2-specific immunoreceptors (T cell receptors and artificial T cell receptors (chimeric antigen receptors; CARs)) and T cell epitopes which are useful for immunotherapy.

Figure 1:
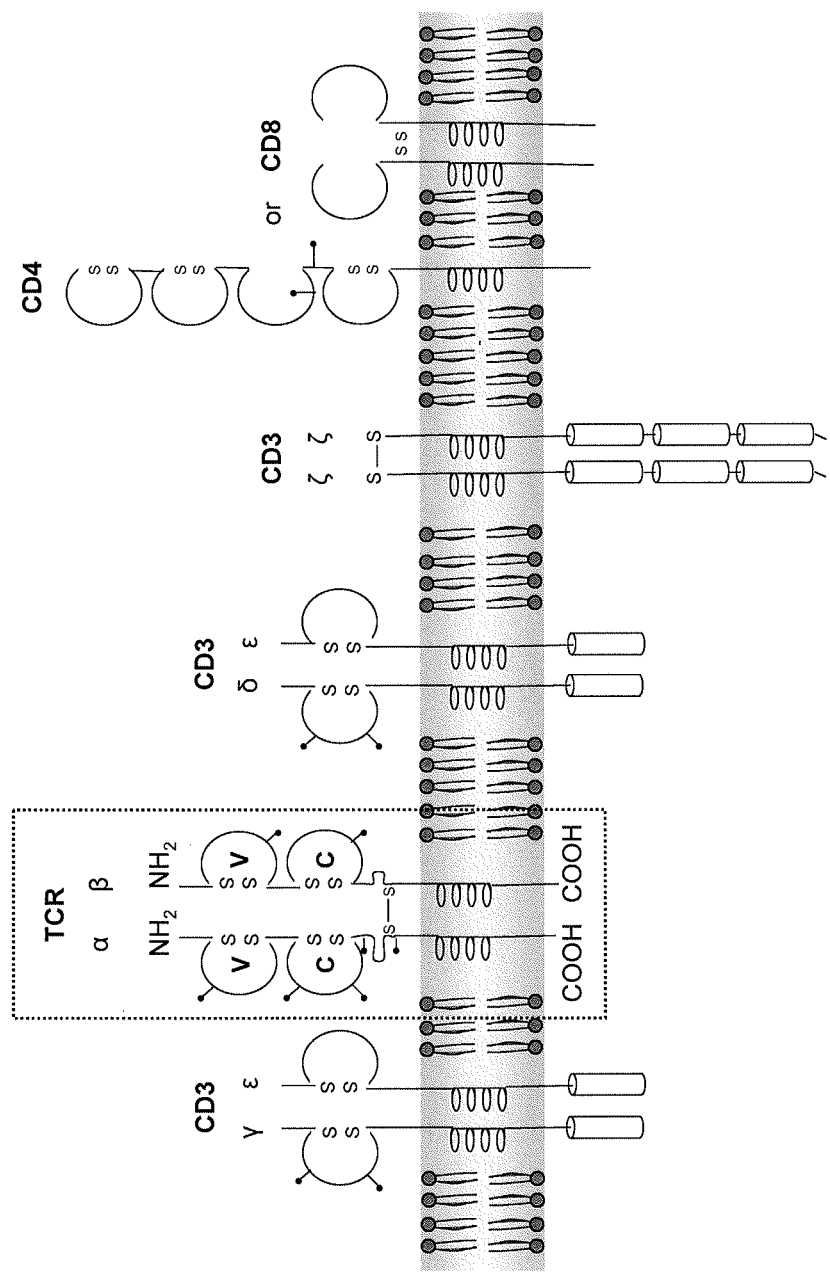

28 Claims, 12 Drawing Sheets
Specification includes a Sequence Listing.

(56) References Cited

OTHER PUBLICATIONS

Gonzalez-Mariscal et al. (Progress in Biophysics & Molecular Biology 81 (2003) 1-44). (Year: 2003).*
Micke et al. (Int. J. Cancer: 135, 2206-2214 (2014)). (Year: 2014).*
Trarbach et al. (Ann Oncol. 2014;25(suppl 4):iv218-iv219). (Year: 2014).*
Sadelain et al., *Cancer Discovery*, 3(4): 388-395 (2013).
Sahin et al., *Clinical Cancer Research*, 14(23): 7624-7634 (2008).
Shi et al., *Molecular Cancer*, 13(1): 219 (2014).
European Patent Office, International Search Report in International Application No. PCT/EP2016/060337 (dated Aug. 10, 2016).
European Patent Office, Written Opinion of the International Search Authority in International Application No. PCT/EP2016/060337 (dated Aug. 10, 2016).
Karanjawala et al., *Am. J. Surg. Pathol.*, 32(2): 188-196 (2008).
Tuereci et al., "IMAB362, a novel first-in-class monoclonal antibody for treatment of pancreatic cancer," *Cancer Research*, 74(19) (2014) (Abstract).
Excerpt of the European Nucleotide Archive, sequence AM332393, created Jan. 16, 2008 and last updated Jan. 19, 2008.
Dotti et al., Immunol Rev., 257(1): 1-35 (2014).
Beatty et al., OncoImmunology, 3(11): e970027 (2014).
Beatty et al., Pharmacol Then, 166:30-39 (Oct. 2016).
USPTO, Office Action in U.S. Appl. No. 16/448,053 dated Jan. 6, 2021.
Opposition Against European Patent No. 3 170 842 B1 (Application No. 15 821 331.4) by BioNTech Cell & Gene Therapies GmbH, 25 pages (Jun. 4, 2020).

* cited by examiner

SYFPEITHY-predicted HLA-A*02 binding peptides

| Name | Sequence | Position | Score SYFPEITHY |
|---|---|---|---|
| CLDN18.2-A2-1 | TLLGLPAML | 68-76 | 27 |
| CLDN18.2-A2-2 | GLPAMLQAV | 71-79 | 26 |
| CLDN18.2-A2-3 | SLIGIAGII | 14-22 | 24 |
| CLDN18.2-A2-4 | GIAGIIAAT | 17-25 | 24 |
| CLDN18.2-A2-5 | QGLGFVVSL | 7-15 | 23 |
| CLDN18.2-A2-6 | GLGFVVSLI | 8-16 | 22 |

CLAUDIN-18.2-SPECIFIC IMMUNORECEPTORS AND T CELL EPITOPES

CROSS REFERENCE TO RELATED APPLICATIONS

This application is a national stage entry of international application PCT/EP2016/060337, which was filed on May 9, 2016 and claimed priority to international application PCT/EP2015/060357, which was filed on May 11, 2015, the entire contents of which are incorporated herein by reference.

TECHNICAL FIELD OF THE INVENTION

The present invention relates to the provision of Claudin-18.2-specific immunoreceptors (T cell receptors and artificial T cell receptors (chimeric antigen receptors; CARs)) and T cell epitopes which are useful for immunotherapy.

BACKGROUND OF THE INVENTION

The evolution of the immune system resulted in vertebrates in a highly effective network based on two types of defense: the innate and the adaptive immunity.

In contrast to the evolutionary ancient innate immune system that relies on invariant receptors recognizing common molecular patterns associated with pathogens, the adoptive immunity is based on highly specific antigen receptors on B cells (B lymphocytes) and T cells (T lymphocytes) and clonal selection.

While B cells raise humoral immune responses by secretion of antibodies, T cells mediate cellular immune responses leading to destruction of recognized cells.

T cells play a central role in cell-mediated immunity in humans and animals. The recognition and binding of a particular antigen is mediated by the T cell receptors (TCRs) expressed on the surface of T cells.

The T cell receptor (TCR) of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. To be able to target a vast variety of antigens, the T cell receptors need to have a great diversity.

This diversity is obtained by genetic rearrangement of different discontinuous segments of genes which code for the different structural regions of TCRs. TCRs are composed of one α-chain and one β-chain or of one γ-chain and one δ-chain. The TCR α/β chains are composed of an N-terminal highly polymorphic variable region involved in antigen recognition and an invariant constant region. On the genetic level, these chains are separated into several regions, a variable (V) region, a diversity (D) region (only β- and δ-chain), a joining (J) region and a constant (C) region. The human β-chain genes contain over 60 variable (V), 2 diversity (D), over 10 joining (J) segments, and 2 constant region segments (C). The human α-chain genes contain over 50 V segments, and over 60 J segments but no D segments, as well as one C segment. The murine β-chain genes contain over 30 variable (V), 2 diversity (D), over 10 joining (J) segments, and 2 constant region segments (C). The murine α-chain genes contain almost 100 V segments, 60 J segments, no D segments, but one C segment. During the differentiation of T cells, specific T cell receptor genes are created by rearranging one V, one D (only β- and δ-chain), one J and one C region gene. The diversity of the TCRs is further amplified by imprecise V-(D)-J rearrangement wherein random nucleotides are introduced and/or deleted at the recombination sites. Since the rearrangement of the TCR gene loci occurs in the genome during maturation of T cells, each mature T cell only expresses one specific α/β TCR or γ/δ TCR.

MHC and antigen binding is mediated by the complementary determining regions 1, 2 and 3 (CDR1, CDR2, CDR3) of the TCR. The CDR3 of the β-chain which is most critical for antigen recognition and binding is encoded by the V-D-J junction of the rearranged TCR β-chain gene.

The TCR is a part of a complex signaling machinery, which includes the heterodimeric complex of the TCR α- and β-chains, the co-receptor CD4 or CD8 and the CD3 signal transduction module (FIG. 1). While the CD3 chains transfer the activation signal inside the cell, the TCR α/β heterodimer is solely responsible for antigen recognition. Thus, the transfer of the TCR α/β chains offers the opportunity to redirect T cells towards any antigen of interest.

Immunotherapy

Antigen-specific immunotherapy aims to enhance or induce specific immune responses in patients to control infectious or malignant diseases. The identification of a growing number of pathogen- and tumor-associated antigens (TAA) led to a broad collection of suitable targets for immunotherapy. Cells presenting immunogenic peptides (epitopes) derived from these antigens can be specifically targeted by either active or passive immunization strategies. Active immunization tends to induce and expand antigen-specific T cells in the patient, which are able to specifically recognize and kill diseased cells. In contrast passive immunization relies on the adoptive transfer of T cells, which were expanded and optional genetically engineered in vitro (adoptive T cell therapy).

Vaccination

Tumor vaccines aim to induce endogenous tumor-specific immune responses by active immunization. Different antigen formats can be used for tumor vaccination including whole cancer cells, proteins, peptides or immunizing vectors such as RNA, DNA or viral vectors that can be applied either directly in vivo or in vitro by pulsing of DCs following transfer into the patient.

The number of clinical studies where therapy-induced immune responses can be identified is steadily increasing due to improvements of immunization strategies and methods for detection of antigen-specific immune responses (Connerotte, T. et al. (2008). Cancer Res. 68, 3931-3940; Schmitt, M. et al. (2008) Blood 111, 1357-1365; Speiser, D. E. et al. (2008) Proc. Natl. Acad. Sci. U. S. A 105, 3849-3854; Adams, S. et al. (2008) J. Immunol. 181, 776-784).

However, in most cases detected immune responses cannot systemically be correlated with clinical outcomes (Curigliano, G. et al. (2006) Ann. Oncol. 17, 750-762; Rosenberg, S. A. et al. (2004) Nat. Med. 10, 909-915).

The exact definition of peptide epitopes derived from tumor antigens may therefore contribute to improve specificity and efficiency of vaccination strategies as well as methods for immunomonitoring.

Adoptive Cell Transfer (ACT)

ACT based immunotherapy can be broadly defined as a form of passive immunization with previously sensitized T cells that are transferred to non-immune recipients or to the autologous host after ex vivo expansion from low precursor frequencies to clinically relevant cell numbers. Cell types that have been used for ACT experiments are lymphokine-activated killer (LAK) cells (Mule, J. J. et al. (1984) Science 225, 1487-1489; Rosenberg, S. A. et al. (1985) N. Engl. J. Med. 313, 1485-1492), tumor-infiltrating lymphocytes (TILs) (Rosenberg, S. A. et al. (1994) J. Natl. Cancer Inst. 86, 1159-1166), donor lymphocytes after hematopoietic stem cell transplantation (HSCT) as well as tumor-specific T cell lines or clones (Dudley, M. E. et al. (2001) J. Immunother. 24, 363-373; Yee, C. et al. (2002) Proc. Natl. Acad. Sci. U. S. A 99, 16168-16173).

Adoptive T cell transfer was shown to have therapeutic activity against human viral infections such as CMV. While CMV infection and reactivation of endogenous latent viruses is controlled by the immune system in healthy individuals, it results in significant morbidity and mortality in immune compromised individuals such as transplant recipients or AIDS patients.

Riddell and co-workers demonstrated the reconstitution of viral immunity by adoptive T cell therapy in immune suppressed patients after transfer of CD8+ CMV-specific T cell clones derived from HLA-matched CMV-seropositive transplant donors (Riddell, S. R. (1992) Science 257, 238-241).

As an alternative approach polyclonal donor-derived CMV- or EBV-specific T cell populations were transferred to transplant recipients resulting in increased persistence of transferred T cells (Rooney, C. M. et al. (1998) Blood 92, 1549-1555; Peggs, K. S. et al. (2003) Lancet 362, 1375-1377).

For adoptive immunotherapy of melanoma Rosenberg and co-workers established an ACT approach relying on the infusion of in vitro expanded autologous tumor-infiltrating lymphocytes (TILs) isolated from excised tumors in combination with a non-myeloablative lymphodepleting chemotherapy and high-dose IL2. A recently published clinical study resulted in an objective response rate of ~50% of treated patients suffering from metastatic melanoma (Dudley, M. E. et al. (2005) J. Clin. Oncol. 23: 2346-2357).

However, patients must fulfill several premises to be eligible for ACT immunotherapy. They must have resectable tumors. The tumors must generate viable TILs under cell culture conditions. The TILs must be reactive against tumor antigens, and must expand in vitro to sufficient numbers. Especially in other cancers than melanoma, it is difficult to obtain such tumor-reactive TILs. Furthermore, repeated in vitro stimulation and clonal expansion of normal human T lymphocytes results in progressive decrease in telomerase activity and shortening of telomeres resulting in replicative senescence and decreased potential for persistence of transferred T cells (Shen, X. et al. (2007) J. Immunother. 30: 123-129).

ACT Using Gene-Engineered T Cells

An approach overcoming the limitations of ACT is the adoptive transfer of autologous T cells reprogrammed to express a tumor-reactive immunoreceptor of defined specificity during short-time ex vivo culture followed by reinfusion into the patient (Kershaw M. H. et al. (2013) Nature Reviews Cancer 13 (8):525-41). This strategy makes ACT applicable to a variety of common malignancies even if tumor-reactive T cells are absent in the patient. Since the antigenic specificity of T cells is rested entirely on the heterodimeric complex of the TCR α- and β-chain, the transfer of cloned TCR genes into T cells offers the potential to redirect them towards any antigen of interest. Therefore, TCR gene therapy provides an attractive strategy to develop antigen-specific immunotherapy with autologous lymphocytes as treatment option. Major advantages of TCR gene transfer are the creation of therapeutic quantities of antigen-specific T cells within a few days and the possibility to introduce specificities that are not present in the endogenous TCR repertoire of the patient.

Several groups demonstrated, that TCR gene transfer is an attractive strategy to redirect antigen-specificity of primary T cells (Morgan, R. A. et al. (2003) J. Immunol. 171, 3287-3295; Cooper, L. J. et al. (2000) J. Virol. 74, 8207-8212; Fujio, K. et al. (2000) J. Immunol. 165, 528-532; Kessels, H. W. et al. (2001) Nat. Immunol. 2, 957-961; Dembic, Z. et al. (1986) Nature 320, 232-238).

Feasibility of TCR gene therapy in humans was recently demonstrated in clinical trials for the treatment of malignant melanoma by Rosenberg and his group. The adoptive transfer of autologous lymphocytes retrovirally transduced with melanoma/melanocyte antigen-specific TCRs resulted in cancer regression in up to 30% of treated melanoma patients (Morgan, R. A. et al. (2006) Science 314, 126-129; Johnson, L. A. et al. (2009) Blood 114, 535-546).

Chimeric Antigen Receptors

Chimeric antigen receptors (CARs) are engineered receptors that combine a single chain variable fragment (scFv) of a monoclonal antibody with an intracellular part consisting of one or more signaling domains for T cell activation. CARs recognize native antigens in a non-MEIC-restricted manner and can therefore be used in all individuals no matter what their HLA type is and they are functional in CD4+ as well as CD8+ T cells.

Figure 2:
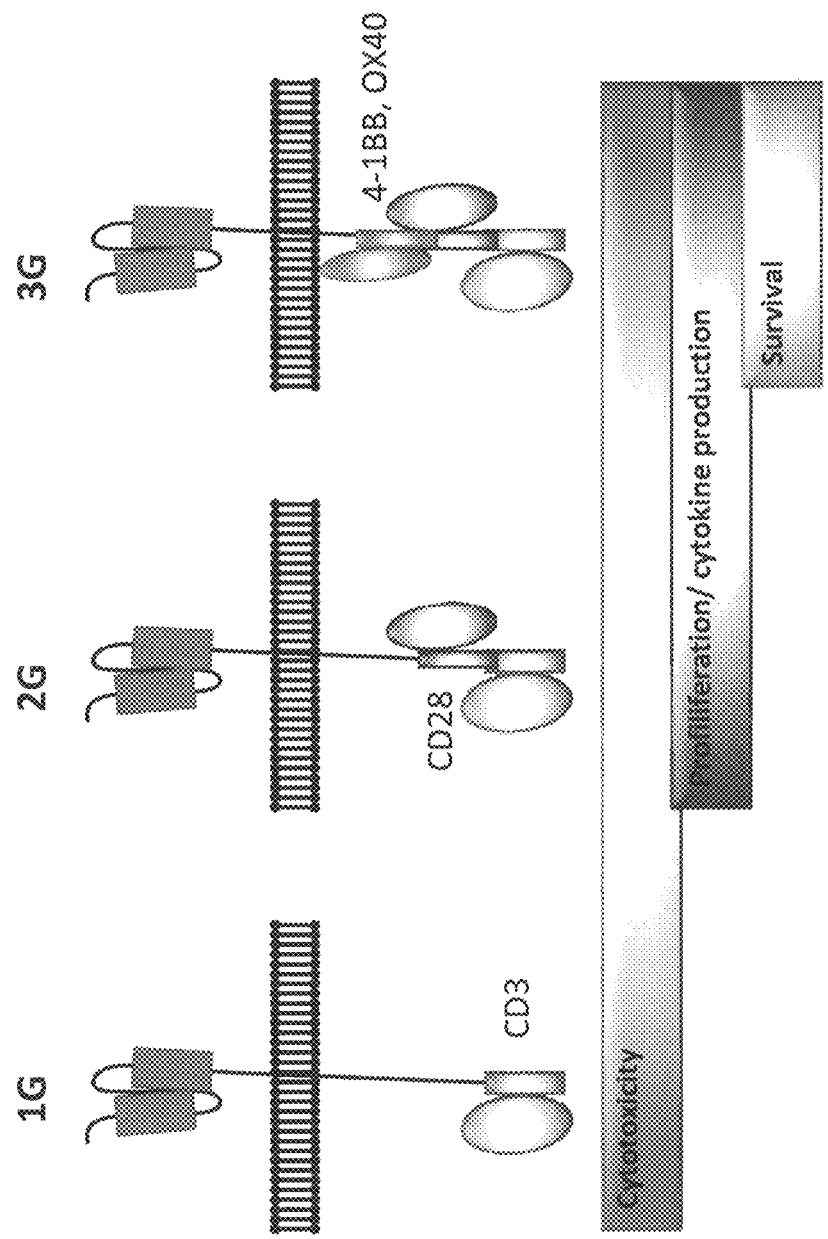

A multitude of CARs has been reported over the past decade, targeting a panel of different cell surface tumor antigens. Their biologic functions were dramatically improved by incorporation of a costimulatory domain resulting in tripartite receptors (scFv, CD28, CD3), termed 2nd generation CARs. CARs of the 3rd generation encompass additional domains of costimulatory molecules such as OX40 and 4-1BB to enhance the proliferative capacity and persistence of modified T-cells (FIG. 2).

Target Structures for Antigen-Specific Immunotherapy

The discovery of multiple tumor-associated antigens (TAAs) has provided the basis for antigen-specific immunotherapy concepts (Novellino, L. et al. (2005) Cancer Immunol. Immunother. 54, 187-207). TAAs are unusual proteins expressed on tumor cells due to their genetic instability, which have no or limited expression in normal cells. These TAAs can lead to specific recognition of malignant cells by the immune system.

Molecular cloning of TAAs by screening of tumor-derived cDNA expression libraries using autologous tumor-specific T cells (van der Bruggen, P. et al. (1991) Science 254, 1643-1647) or circulating antibodies (Sahin, U. et al. (1995) Proc. Natl. Acad. Sci. U. S. A 92, 11810-11813), reverse immunology approaches, biochemical methods (Hunt, D. F. et al. (1992) Science 256, 1817-1820), gene expression analyses or in silico cloning strategies (Helftenbein, G. et al. (2008) Gene 414, 76-84) led to a significant number of target candidates for immunotherapeutic strategies. TAAs fall in several categories, including differentiation antigens, overexpressed antigens, tumor-specific splice variants, mutated gene products, viral and cancer testis antigens (CTAs). The cancer testis family is a very promising category of TAAs as their expression is restricted to the testis and a multitude of different tumor entities (Scanlan, M. J. et al. (2002) Immunol. Rev. 188, 22-32). Until now more than 50 CT genes have been described (Scanlan, M. J. et al. (2004) Cancer Immun. 4, 1) and some of them have been addressed in clinical studies (Adams, S. et al. (2008) J. Immunol. 181, 776-784; Atanackovic, D. et al. (2004) J. Immunol. 172, 3289-3296; Chen, Q. et al. (2004) Proc. Natl.

Acad. Sci. U. S. A 101, 9363-9368; Connerotte, T. et al. (2008). Cancer Res. 68, 3931-3940; Davis, I. D. et al. (2004) Proc. Natl. Acad. Sci. U. S. A 101, 10697-10702; Jager, E. (2000) Proc. Natl. Acad. Sci. U. S. A 97, 12198-12203; Marchand, M. et al. (1999) Int. J. Cancer 80, 219-230; Schuler-Thurner, B. et al. (2000) J. Immunol. 165, 3492-3496).

In spite of the growing number of attractive target structures for immunotherapeutic approaches specific T cell clones or lines of defined HLA restriction do only exist for a few of them (Chaux, P. et al. (1999) J. Immunol. 163, 2928-2936; Zhang, Y. et al. (2002) Tissue Antigens 60, 365-371; Zhao, Y. et al. (2005) J. Immunol. 174, 4415-4423).

Claudins are integral membrane proteins located within the tight junctions of epithelia and endothelia. Claudins are predicted to have four transmembrane segments with two extracellular loops, and N- and C-termini located in the cytoplasm. The Claudin (CLDN) family of transmembrane proteins plays a critical role in the maintenance of epithelial and endothelial tight junctions and might also play a role in the maintenance of the cytoskeleton and in cell signalling.

CLDN18 belongs to the family of claudins, which are cell surface molecules with four membrane-spanning domains involved in the formation of tight junctions (Tsukita S, Nat Rev Mol Cell Biol 2001; 2:285-93). The human CLDN18 gene has two alternative first exons, giving rise to two protein isoforms (CLDN18.1 and CLDN18.2) differing in the N-terminal 69 amino acids (Niimi T, MolCellBiol 2001; 21:7380-90), including the first extracellular loop (FIG. 4A). Transcription profiling of a restricted set of tissues has shown that these isoforms have different lineage commitments, with CLDN18.1 being predominantly expressed in lung tissue whereas CLDN18.2 displays stomach specificity. CLDN18.2 expression is confined to short-lived differentiated epithelia of the gastric mucosa and is absent from the gastric stem cell zone and any other healthy tissue. CLDN18.2 expression has been associated with gastroesophageal, pancreatic, and other cancers (FIG. 4B, C; Sahin U et al., Clin Cancer Res 2008; 14:7624-34; Karanjawala Z E et al., Am J Surg Pathol 2008; 32:188-96;). A recombinant mAb against this target is currently in clinical Phase II trials, but the evaluation of CLDN18.2 as a target for T cell based therapy approaches has not been addressed yet.

The frequent overexpression of CLDN18.2 on tumors qualifies this molecule as a highly attractive target for development of therapeutics directed against CLDN18.2 such as vaccine therapeutics and therapeutic antibodies. However, hitherto no HLA-A*2-restricted CLDN18.2 T cell epitopes and T cell receptors or CARs targeting CLDN18.2 have been described and it is unknown whether CLDN18.2 expressing cancer cells can be targeted in vivo by immunotherapies involving T cells using active or passive immunization approaches.

DESCRIPTION OF INVENTION

Summary of the Invention

The present invention relates to T cell receptors and artificial T cell receptors specific for the tumor-associated antigen CLDN18.2, in particular when present on the surface of a cell such as a diseased cell or presented on the surface of a cell such as a diseased cell or an antigen-presenting cell, as well as peptides comprising epitopes recognized by these T cell receptors, i.e. CLDN18.2-T cell epitopes.

By adoptive transfer of T cells engineered to express such T cell receptor or artificial T cell receptor CLDN18.2 expressing cancer cells can be specifically targeted thereby leading to selective destruction of cancer cells. Furthermore, the T cell epitopes provided according to the invention are useful for designing vaccines against CLDN18.2-expressing cancers.

In one aspect, the invention relates to a peptide comprising an amino acid sequence selected from the group consisting of SEQ ID NOs: 2, 3, 4, 5, 6 and 7 or a variant of said amino acid sequence. In one embodiment the peptide is 100 or less, 50 or less, 20 or less, or 10 or less amino acids long. In one embodiment, the peptide can be processed to produce a peptide consisting of the amino acid sequence selected from the group consisting of SEQ ID NOs: 2, 3, 4, 5, 6 and 7 or a variant of said amino acid sequence. In one embodiment, the peptide consists of the amino acid sequence selected from the group consisting of SEQ ID NOs: 2, 3, 4, 5, 6 and 7 or a variant of said amino acid sequence.

In one embodiment, the peptide is a MHC class I or class II presented peptide, preferably a MHC class I presented peptide, or, if present within cells, can be processed to produce a procession product thereof which is a MHC class I or class II presented peptide, preferably a MHC class I presented peptide. Preferably, said MHC class I or class II presented peptide has a sequence substantially corresponding to the given amino acid sequence, i.e. an amino acid sequence selected from the group consisting of SEQ ID NOs: 2, 3, 4, 5, 6 and 7 or a variant of said amino acid sequence. Preferably, a peptide according to the invention is capable of stimulating a cellular response against a disease involving cells characterized by presentation of CLDN18.2 with class I MHC.

In further aspects, the invention relates to a nucleic acid comprising a nucleotide sequence encoding the peptide of the invention and a cell comprising the nucleic acid. The nucleic acid may be a recombinant nucleic acid. The nucleic acid may be present in a plasmid or an expression vector and may be functionally linked to a promoter. In one embodiment, the nucleic acid is RNA. Preferably, the cell expresses the peptide. The cell may be a recombinant cell and may secrete the encoded peptide or a procession product thereof, may express it on the surface and preferably may additionally express an MHC molecule which binds to said peptide or a procession product thereof and preferably presents said peptide or a procession product thereof on the cell surface. In one embodiment, the cell expresses the MHC molecule endogenously. In a further embodiment, the cell expresses the MHC molecule and/or the peptide in a recombinant manner. The cell is preferably nonproliferative. In a preferred embodiment, the cell is an antigen-presenting cell, in particular a dendritic cell, a monocyte or a macrophage.

In a further aspect, the invention relates to a cell that presents the peptide of the invention or a procession product thereof, wherein the procession product preferably is a peptide having the given amino acid sequence, i.e. an amino acid sequence selected from the group consisting of SEQ ID NOs: 2, 3, 4, 5, 6 and 7 or a variant of said amino acid sequence. In one embodiment, said cell is a cell comprising a nucleic acid comprising a nucleotide sequence encoding the peptide of the invention. Preferably said cell expresses said nucleic acid so as to produce said peptide. Optionally said cell processes said peptide so as to produce a peptide consisting of an amino acid sequence selected from the group consisting of SEQ ID NOs: 2, 3, 4, 5, 6 and 7 or a variant of said amino acid sequence. The cell may present the peptide or a procession product thereof by MHC molecules on its surface. In one embodiment, the cell endogenously expresses an MHC molecule. In a further embodiment, the cell recombinantly expresses an MHC molecule. In one embodiment, the MHC molecules of the cell are loaded (pulsed) with the peptide by addition of the peptide to the cell. The cell may recombinantly express the peptide and present said peptide or a procession product thereof on the cell surface. The cell is preferably nonproliferative. In a preferred embodiment, the cell is an antigen-presenting cell such as a dendritic cell, a monocyte or a macrophage.

In a further aspect, the invention relates to an immunoreactive cell which is reactive with a peptide of the invention, in particular when presented on the surface of a cell such as a diseased cell. The immunoreactive cell may be a cell that has been sensitized in vitro to recognize the peptide. The immunoreactive cell may be a T cell, preferably a cytotoxic T cell. Preferably, the immunoreactive cell binds to a sequence substantially corresponding to the given amino acid sequence, i.e. an amino acid sequence selected from the group consisting of SEQ ID NOs: 2, 3, 4, 5, 6 and 7 or a variant of said amino acid sequence, in particular when bound to MHC such as MHC on the surface of a cell such as a diseased cell.

In a further aspect, the invention relates to a binding agent which binds to a peptide of the invention, optionally in a complex with an MHC molecule.

In a further aspect, the invention relates to a T cell receptor which binds to a peptide of the invention, optionally in a complex with an MHC molecule, and preferably is reactive with said peptide, or a polypeptide chain of said T cell receptor. In one embodiment, the polypeptide chain of said T cell receptor is a T cell receptor α-chain or T cell receptor β-chain.

In a further aspect, the invention relates to a T cell receptor α-chain or a T cell receptor comprising said T cell receptor α-chain,
wherein said T cell receptor α-chain is selected from the group consisting of:
(i) a T cell receptor α-chain comprising at least one, preferably two, more preferably all three of the CDR sequences of a T cell receptor α-chain selected from the group consisting of SEQ ID NOs: 8, 10, 12, 14, 16 and 18 or a variant thereof and
(ii) a T cell receptor α-chain comprising a T cell receptor α-chain sequence selected from the group consisting of SEQ ID NOs: 8, 10, 12, 14, 16 and 18 or a fragment thereof, or a variant of said sequence or fragment.

In one embodiment, said SEQ ID NOs: are selected from the group consisting of SEQ ID NOs: 8, 10, 14 and 18 and said T cell receptor is reactive with a peptide comprising the amino acid sequence of SEQ ID NO: 6 or a variant of said amino acid sequence.

In one embodiment, said SEQ ID NOs: are selected from the group consisting of SEQ ID NOs: 10, 12 and 14 and said T cell receptor is reactive with a peptide comprising the amino acid sequence of SEQ ID NO: 7 or a variant of said amino acid sequence.

In a further aspect, the invention relates to a T cell receptor β-chain or a T cell receptor comprising said T cell receptor β-chain, wherein said T cell receptor β-chain is selected from the group consisting of:
(i) a T cell receptor β-chain comprising at least one, preferably two, more preferably all three of the CDR sequences of a T cell receptor β-chain selected from the group consisting of SEQ ID NOs: 9, 11, 13, 15, 17 and 19 or a variant thereof and
(ii) a T cell receptor β-chain comprising a T cell receptor β-chain sequence selected from the group consisting of SEQ ID NOs: 9, 11, 13, 15, 17 and 19 or a fragment thereof, or a variant of said sequence or fragment.

In one embodiment, said SEQ ID NOs: are selected from the group consisting of SEQ ID NOs: 9, 11, 15 and 19 and said T cell receptor is reactive with a peptide comprising the amino acid sequence of SEQ ID NO: 6 or a variant of said amino acid sequence.

In one embodiment, said SEQ ID NOs: are selected from the group consisting of SEQ ID NOs: 11, 13 and 15 and said T cell receptor is reactive with a peptide comprising the amino acid sequence of SEQ ID NO: 7 or a variant of said amino acid sequence.

In a further aspect, the invention relates to a T cell receptor selected from the group consisting of:
(I) a T cell receptor comprising:
  (i) a T cell receptor α-chain comprising at least one, preferably two, more preferably all three of the CDR sequences of the T cell receptor α-chain of SEQ ID NO: x or a variant thereof, and
  (ii) a T cell receptor β-chain comprising at least one, preferably two, more preferably all three of the CDR sequences of a T cell receptor β-chain of SEQ ID NO: x+1 or a variant thereof;
wherein x selected from the group consisting of 8, 10, 12, 14, 16 and 18 and
(II) a T cell receptor comprising:
  (i) a T cell receptor α-chain comprising the T cell receptor α-chain sequence of SEQ ID NO: x or a fragment thereof, or a variant of said sequence or fragment, and
  (ii) a T cell receptor β-chain comprising the T cell receptor β-chain sequence of SEQ ID NO: x+1 or a fragment thereof, or a variant of said sequence or fragment;
wherein x selected from the group consisting of 8, 10, 12, 14, 16 and 18.

In one embodiment, said x is selected from the group consisting of 8, 10, 14 and 18 and said T cell receptor is reactive with a peptide comprising the amino acid sequence of SEQ ID NO: 6 or a variant of said amino acid sequence.

In one embodiment, said x is selected from the group consisting of 10, 12 and 14 and said T cell receptor is reactive with a peptide comprising the amino acid sequence of SEQ ID NO: 7 or a variant of said amino acid sequence.

In one embodiment, binding of said T cell receptor when expressed by T cells and/or present on T cells to CLDN18.2-peptide epitopes as described above presented on cells such as cancer cells results in proliferation and/or activation of said T cells, wherein said activated T cells preferably release cytotoxic factors, e.g. perforins and granzymes, and initiate cytolysis and/or apoptosis of cancer cells.

In a further aspect, the invention relates to an artificial T cell receptor which binds to claudin-18.2 (CLDN18.2). In one embodiment, binding is a specific binding.

In one embodiment, said CLDN18.2 is expressed in a cancer cell. In one embodiment said CLDN18.2 is expressed on the surface of a cancer cell. In one embodiment said artificial T cell receptor binds to an extracellular domain or to an epitope in an extracellular domain of CLDN18.2. In one embodiment said artificial T cell receptor binds to native epitopes of CLDN18.2 present on the surface of living cells. In one embodiment said artificial T cell receptor binds to the first extracellular loop of CLDN18.2. In one embodiment, binding of said artificial T cell receptor when expressed by T cells and/or present on T cells to CLDN18.2 present on cells such as cancer cells results in proliferation and/or activation of said T cells, wherein said activated T cells preferably release cytotoxic factors, e.g. perforins and granzymes, and initiate cytolysis and/or apoptosis of cancer cells.

In one embodiment, the artificial T cell receptor of the invention comprises a binding domain for CLDN18.2. In one embodiment, the binding domain for CLDN18.2 is comprised by an exodomain of said artificial T cell receptor. In one embodiment, the binding domain for CLDN18.2 comprises a single-chain variable fragment (scFv) of a CLDN18.2 antibody. In one embodiment, the binding domain for CLDN18.2 comprises a variable region of a heavy chain of an immunoglobulin (VH) with a specificity for CLDN18.2 (VH(CLDN18.2)) and a variable region of a light chain of an immunoglobulin (VL) with a specificity for CLDN18.2 (VL(CLDN18.2)). In one embodiment, said heavy chain variable region (VH) and the corresponding light chain variable region (VL) are connected via a peptide linker, preferably a peptide linker comprising the amino acid sequence (GGGGS)3. In one embodiment, the binding domain for CLDN18.2 comprises a VH(CLDN18.2) comprising an amino acid sequence represented by SEQ ID NO: 23 or a fragment thereof, or a variant of said amino acid sequence or fragment. In one embodiment, the binding domain for CLDN18.2 comprises a VL(CLDN18.2) comprising an amino acid sequence represented by SEQ ID NO: 30 or a fragment thereof, or a variant of said amino acid sequence or fragment. In one embodiment, the binding domain for CLDN18.2 comprises a VH(CLDN18.2) comprising an amino acid sequence represented by SEQ ID NO: 23 or a fragment thereof, or a variant of said amino acid sequence or fragment and a VL(CLDN18.2) comprising an amino acid sequence represented by SEQ ID NO: 30 or a fragment thereof, or a variant of said amino acid sequence or fragment. In one embodiment, the binding domain for CLDN18.2 comprises an amino acid sequence represented by SEQ ID NO: 35 or a fragment thereof, or a variant of said amino acid sequence or fragment.

In one embodiment, the binding domain for CLDN18.2 recognizes the same or essentially the same epitope as a binding domain for CLDN18.2 or an antibody to CLDN18.2) comprising a VH(CLDN18.2) comprising an amino acid sequence represented by SEQ ID NO: 23 or a fragment thereof, or a variant of said amino acid sequence or fragment and a VL(CLDN18.2) comprising an amino acid sequence represented by SEQ ID NO: 30 or a fragment thereof, or a variant of said amino acid sequence or fragment and/or competes with said CLDN18.2-binding domain or CLDN18.2-antibody for binding to CLDN18.2. In one embodiment, the binding domain for CLDN18.2 recognizes the same or essentially the same epitope as the binding domain for CLDN18.2 comprising an amino acid sequence represented by SEQ ID NO: 35 or a fragment thereof, or a variant of said amino acid sequence or fragment and/or competes with said CLDN18.2-binding domain for binding to CLDN18.2. A binding domain which competes with a second binding domain or an antibody for binding to a target preferably is antagonistic to said second binding domain or antibody.

In one embodiment, the artificial T cell receptor of the invention comprises a transmembrane domain. In one embodiment, the transmembrane domain is a hydrophobic alpha helix that spans the membrane. In one embodiment, the transmembrane domain comprises the CD28 transmembrane domain or a fragment thereof.

In one embodiment, the artificial T cell receptor of the invention comprises a T cell signaling domain. In one embodiment, the T cell signaling domain is located intracellularly. In one embodiment, the T cell signaling domain comprises CD3-zeta, preferably the endodomain of CD3-zeta, optionally in combination with CD28. In one embodiment, the T cell signaling domain comprises the sequence according to SEQ ID NO: 40 or a fragment thereof, or a variant of said sequence or fragment.

In one embodiment, the artificial T cell receptor of the invention comprises a signal peptide which directs the nascent protein into the endoplasmic reticulum. In one embodiment, the signal peptide precedes the binding domain for CLDN18.2. In one embodiment, the signal peptide comprises the sequence according to SEQ ID NO: 37 or a fragment thereof, or a variant of said sequence or fragment.

In one embodiment, the artificial T cell receptor of the invention comprises a spacer region which links the binding domain for CLDN18.2 to the transmembrane domain. In one embodiment, the spacer region allows the binding domain for CLDN18.2 to orient in different directions to facilitate CLDN18.2 recognition. In one embodiment, the spacer region comprises the hinge region from IgG1. In one embodiment, the spacer region comprises the sequence according to SEQ ID NO: 38 or a fragment thereof, or a variant of said sequence or fragment.

In one embodiment, the artificial T cell receptor of the invention comprises the structure:

NH2-signal peptide-binding domain for CLDN18.2-spacer region-transmembrane domain-T cell signaling domain-COOH.

In one embodiment, the artificial T cell receptor of the invention comprises the amino acid sequence according to SEQ ID NO: 41 or a fragment thereof, or a variant of said amino acid sequence or fragment.

The above T cell receptors and artificial T cell receptors are preferably specific for the tumor-associated antigen CLDN18.2, in particular when present on the surface of a cell such as a diseased cell or when presented on the surface of a cell such as a diseased cell or an antigen-presenting cell.

The T cell receptors and artificial T cell receptors of the invention may be expressed by and/or present on the surface of cells such as T cells.

In a further aspect, the invention relates to a nucleic acid comprising a nucleotide sequence encoding the T cell receptor chain or T cell receptor of the invention or encoding the artificial T cell receptor of the invention. In one embodiment, the nucleic acid is a recombinant nucleic acid. In one embodiment, the nucleic acid is in the form of a vector or in the form of RNA.

In a further aspect, the invention relates to a cell comprising the T cell receptor chain or T cell receptor of the invention or the artificial T cell receptor of the invention and/or comprising a nucleic acid comprising a nucleotide sequence encoding the T cell receptor chain or T cell receptor of the invention or encoding the artificial T cell receptor of the invention. In one embodiment, said nucleic acid is RNA, preferably in vitro transcribed RNA. The cell may be a cell expressing the T cell receptor chain or T cell receptor of the invention or the artificial T cell receptor of the invention and/or may have the T cell receptor chain or T cell receptor of the invention or the artificial T cell receptor of the invention on its cell surface. In one embodiment, said cell is a cell which is useful for adoptive cell transfer. The cell may be an effector or stem cell, preferably an immunoreactive cell. The immunoreactive cell may be a T cell, preferably a cytotoxic T cell. In one embodiment, the immunoreactive cell is reactive with the tumor-associated antigen CLDN18.2. In one embodiment, said CLDN18.2 is present on the surface of a cell such as a diseased cell. In one embodiment, said CLDN18.2 is presented on the surface of a cell such as a diseased cell or an antigen-presenting cell, and the immunoreactive cell is reactive with a peptide of the invention, in particular when presented in the context of MI-IC, and preferably binds to a sequence substantially corresponding to the given amino acid sequence, i.e. an amino acid sequence selected from the group consisting of SEQ ID NOs: 6 and 7 or a variant of said amino acid sequence. In one embodiment, said cell lacks surface expression of an endogenous TCR or is specific for a CLDN18.2-unrelated antigen.

In one embodiment, cells of the invention prior to use in adoptive cell transfer are subjected to an antigen-specific expansion and rechallenge, wherein the antigen-specific expansion and rechallenge may be effected by exposing the cells to preferably autologous antigen presenting cells presenting CLDN18.2 or a peptide fragment thereof.

In a further aspect, the invention relates to a method of producing an immunoreactive cell comprising the step of transducing a T cell with a nucleic acid comprising a nucleotide sequence encoding the T cell receptor chain or T cell receptor of the invention or encoding the artificial T cell receptor of the invention.

Furthermore, the present invention generally embraces the treatment of diseases by targeting diseased cells such as cancer cells, in particular cancer cells expressing CLDN18.2. The methods provide for the selective eradication of cells that express on their surface and/or present the tumor-associated antigen CLDN18.2, thereby minimizing adverse effects to normal cells not expressing and/or presenting CLDN18.2. Thus, preferred diseases for a therapy are those in which CLDN18.2 is expressed and optionally presented such as cancer diseases, in particular those described herein.

When a peptide of the invention, a nucleic acid comprising a nucleotide sequence encoding the peptide of the invention or a cell of the invention comprising said nucleic acid is administered, the treatment preferably involves an active immunization. Preferably, CLDN18.2-specific T cells are expanded in the patient, which are able to recognize and kill diseased cells. When an immunoreactive cell of the invention, a T cell receptor of the invention, an artificial T cell receptor of the invention, a nucleic acid of the invention comprising a nucleotide sequence encoding a T cell receptor of the invention or encoding an artificial T cell receptor of the invention or a cell of the invention comprising a T cell receptor or an artificial T cell receptor of the invention and/or comprising a nucleic acid of the invention comprising a nucleotide sequence encoding a T cell receptor of the invention or encoding an artificial T cell receptor of the invention is administered, the treatment preferably involves a passive immunization. Preferably, CLDN18.2-specific T cells which are able to recognize and kill diseased cells and which were optionally genetically engineered and/or expanded in vitro are adoptively transferred to a patient.

In one aspect, the invention relates to a pharmaceutical composition comprising one or more of:
(i) the peptide of the invention;
(ii) the nucleic acid of the invention;
(iii) the cell of the invention;
(iv) the immunoreactive cell of the invention;
(v) the binding agent of the invention;
(vi) the T cell receptor of the invention; and
(vi) the artificial T cell receptor of the invention.

A pharmaceutical composition of the invention may comprise a pharmaceutically acceptable carrier and may optionally comprise one or more adjuvants, stabilizers etc. The pharmaceutical composition may in the form of a therapeutic or prophylactic vaccine. In one embodiment, the pharmaceutical composition is for use in treating or preventing a cancer disease such as those described herein.

Administration of a pharmaceutical composition as described above may provide MHC class II-presented epitopes that are capable of eliciting a CD4+ helper T cell response and/or a CD8+ T cell response against CLDN18.2 (including cells expressing CLDN18.2 on their surface and/or presenting CLDN18.2 in the context of MHC molecules). Alternatively or additionally, administration of a pharmaceutical composition as described above may provide MHC class I-presented epitopes that are capable of eliciting a CD8+ T cell response against CLDN18.2.

In a further aspect, the invention relates to a method of treating or preventing a cancer disease comprising administering to a patient the pharmaceutical composition of the invention.

In a further aspect, the invention relates to the peptide of the invention, the nucleic acid of the invention, the cell of the invention, the immunoreactive cell of the invention, the binding agent of the invention, the T cell receptor of the invention, or the artificial T cell receptor of the invention for use in therapy, in particular for use in treating or preventing cancer.

Another aspect relates to a method for inducing an immune response in a subject, comprising administering to the subject a pharmaceutical composition of the invention.

Another aspect relates to a method for stimulating, priming and/or expanding T cells, comprising contacting T cells with one or more of: the peptide of the invention, the nucleic acid of the invention comprising a nucleotide sequence encoding the peptide of the invention, the cell of the invention comprising said nucleic acid and/or the cell of the invention that presents the peptide of the invention or a procession product thereof. In one embodiment, the peptide of the invention is presented in the context of MHC molecules such as MHC molecules on the surface of cells, e.g. antigen-presenting cells.

In this aspect, the invention may relate to a method for preparing CLDN18.2-specific T cells. The T cells may be stimulated, primed and/or expanded in vitro or in vivo. Preferably, the T cells are present in a sample obtained from a subject. The stimulated, primed and/or expanded T cells may be administered to a subject and may be autologous, allogeneic, syngeneic to the subject.

The invention in the above aspects of a method for inducing an immune response in a subject or of a method for stimulating, priming and/or expanding T cells may relate to a method for treating cancer diseases in a subject.

Another aspect relates to a method of killing cancer cells in a subject, comprising the step of providing to the subject a therapeutically effective amount of the peptide of the invention, the nucleic acid of the invention, the cell of the invention, the immunoreactive cell of the invention, the binding agent of the invention, the T cell receptor of the invention, or the artificial T cell receptor of the invention.

The compositions and agents described herein are preferably capable of inducing or promoting a cellular response, preferably cytotoxic T cell activity, against a disease characterized by expression of CLDN18.2 and/or presentation of CLDN18.2 with class I MHC, e.g. a cancer disease.

In one aspect, the invention provides the agents and compositions described herein for use in the methods of treatment described herein.

The treatments of cancer diseases described herein can be combined with surgical resection and/or radiation and/or traditional chemotherapy.

In another aspect, the invention relates to a method for determining an immune response in a subject, comprising determining T cells reactive with a peptide of the invention or a cell of the invention presenting a peptide of the invention or a procession product thereof in a biological sample isolated from the subject. The method may comprise the steps of:

(a) incubating a sample comprising T cells isolated from a subject with one or more of:
 (i) the peptide of the invention;
 (ii) the nucleic acid of the invention comprising a nucleotide sequence encoding the peptide of the invention; and
 (iii) the cell of the invention comprising said nucleic acid or the cell of the invention presenting a peptide of the invention or a procession product thereof;
 and
(b) detecting the specific activation of the T cells, therefrom determining the presence or absence of an immune response in said subject.

The invention in the above aspects of a method for determining an immune response in a subject may relate to a method for diagnosing cancer diseases in a subject.

In one embodiment of the methods for diagnosis, the biological sample is from a tissue or organ wherein the cells when the tissue or organ is disease free do not substantially express CLDN18.2.

Typically, the level of T cells in a biological sample is compared to a reference level, wherein a deviation from said reference level is indicative of the presence and/or stage of a disease in a subject. The reference level may be a level as determined in a control sample (e.g., from a healthy tissue or subject) or a median level from healthy subjects. A "deviation" from said reference level designates any significant change, such as an increase by at least 10%, 20%, or 30%, preferably by at least 40% or 50%, or even more. Preferably, the presence of the T cells in said biological sample or a quantity of the T cells in the biological sample which is increased compared to a reference level indicates the presence of a disease.

T cells may be isolated from patient peripheral blood, lymph nodes, tissue samples such as derived from biopsy and resection, or other source. Reactivity assays may be performed on primary T cells or other appropriate derivatives. For example, T cells may be fused to generate hybridomas. Assays for measuring T cell responsiveness are known in the art, and include proliferation assays and cytokine release assays.

Assays and indices for detecting reactive T cells include but are not limited to the use of IFNγ ELISPOT and IFNγ intracellular cytokine staining. Other various methods are known in the art for determining whether a T cell clone will respond to a particular peptide. Typically the peptide is added to a suspension of the T cells for a period of from one to three days. The response of the T cells may be measured by proliferation, e.g., uptake of labeled thymidine, or by release of cytokines, e.g., IL-2. Various assays are available for detecting the presence of released cytokines. T cell cytotoxic assays can be used to detect cytotoxic T cells having specificity for antigens. In one embodiment, cytotoxic T cells are tested for their ability to kill target cells presenting an antigen with MHC class I molecules. Target cells presenting an antigen may be labeled and added to a suspension of T cells from a patient sample. The cytotoxicity may be measured by quantifying the release of label from lysed cells. Controls for spontaneous and total release may be included in the assay.

In one embodiment of the invention, a cancer described herein involves cancer cells expressing CLDN18.2 and/or presenting CLDN18.2 in the context of MHC molecules. In one embodiment of the invention, diseased cells are cancer cells. In one embodiment, diseased cells such as cancer cells are cells expressing CLDN18.2 and/or presenting CLDN18.2 in the context of MHC molecules. In one embodiment, expression of CLDN18.2 is on the surface of a diseased cell.

In one embodiment of the invention, a cancer is an adenocarcinoma, in particular an advanced adenocarcinoma. In one embodiment, a cancer is selected from the group consisting of gastric cancer, esophageal cancer, pancreatic cancer, lung cancer such as non small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis. In one embodiment, the cancer is selected from the group consisting of cancer of the stomach, cancer of the esophagus, in particular the lower esophagus, cancer of the eso-gastric junction and gastroesophageal cancer. In one embodiment, the patient is a HER2/neu negative patient or a patient with HER2/neu positive status but not eligible to trastuzumab therapy.

In one embodiment of the invention, cancer cells are cancer cells of a cancer selected from the group consisting of gastric cancer, esophageal cancer, pancreatic cancer, lung cancer such as non small cell lung cancer (NSCLC), breast cancer, ovarian cancer, colon cancer, hepatic cancer, head-neck cancer, cancer of the gallbladder and the metastasis thereof, a Krukenberg tumor, peritoneal metastasis and/or lymph node metastasis. In one embodiment, cancer cells are cancer cells of a cancer selected from the group consisting of cancer of the stomach, cancer of the esophagus, in particular the lower esophagus, cancer of the eso-gastric junction and gastroesophageal cancer.

According to the invention, CLDN18.2 preferably has the amino acid sequence according to SEQ ID NO: 1.

Other features and advantages of the instant invention will be apparent from the following detailed description and claims.

DETAILED DESCRIPTION OF THE INVENTION

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) Helvetica Chimica Acta, CH-4010 Basel, Switzerland.

The practice of the present invention will employ, unless otherwise indicated, conventional methods of biochemistry, cell biology, immunology, and recombinant DNA techniques which are explained in the literature in the field (cf., e.g., *Molecular Cloning: A Laboratory Manual, 2nd* Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The term "recombinant" in the context of the present invention means "made through genetic engineering". Preferably, a "recombinant object" such as a recombinant cell in the context of the present invention is not occurring naturally.

The term "naturally occurring" as used herein refers to the fact that an object can be found in nature. For example, a peptide or nucleic acid that is present in an organism (including viruses) and can be isolated from a source in nature and which has not been intentionally modified by man in the laboratory is naturally occurring.

The term "immune response" refers to an integrated bodily response to an antigen and preferably refers to a cellular immune response or a cellular as well as a humoral immune response. The immune response may be protective/preventive/prophylactic and/or therapeutic.

"Inducing an immune response" may mean that there was no immune response against a particular antigen before induction, but it may also mean that there was a certain level of immune response against a particular antigen before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. For example, an immune response against a tumor-associated antigen such as CLDN18.2 may be induced in a patient having a cancer disease or in a subject being at risk of developing a cancer disease. Inducing an immune response in this case may mean that the disease condition of the subject is ameliorated, that the subject does not develop metastases, or that the subject being at risk of developing a cancer disease does not develop a cancer disease.

A "cellular immune response", a "cellular response", a "cellular response against an antigen" or a similar term is meant to include a cellular response directed to cells characterized by presentation of an antigen with class I or class II MHC. The cellular response relates to cells called T cells or T-lymphocytes which act as either 'helpers' or 'killers'. The helper T cells (also termed $CD4^+$ T cells) play a central role by regulating the immune response and the killer cells (also termed cytotoxic T cells, cytolytic T cells, $CD8^+$ T cells or CTLs) kill diseased cells such as cancer cells, preventing the production of more diseased cells.

The term "antigen" relates to an agent comprising an epitope against which an immune response is to be generated and/or is directed. Preferably, an antigen in the context of the present invention is a molecule which, optionally after processing, induces an immune reaction, which is preferably specific for the antigen or cells expressing and/or presenting the antigen. The term "antigen" includes in particular proteins and peptides. An antigen is preferably a product which corresponds to or is derived from a naturally occurring antigen. Such naturally occurring antigens may include or may be derived from tumor-associated antigens.

In particular, the antigen or peptide fragments thereof should be recognizable by a T cell receptor. Preferably, the antigen or peptide if recognized by a T cell receptor is able to induce in the presence of appropriate co-stimulatory signals, clonal expansion of the T cell carrying the T cell receptor recognizing the antigen or peptide. In the context of the embodiments of the present invention, the antigen is preferably presented by a cell, preferably by an antigen presenting cell and/or a diseased cell, in the context of MHC molecules, which may result in an immune reaction against the antigen (or cell presenting the antigen).

In a preferred embodiment, an antigen is a tumor-associated antigen, i.e., a constituent of cancer cells which may be derived from the cytoplasm, the cell surface and the cell nucleus, in particular those antigens which are produced, preferably in large quantity, intracellular or as surface antigens on cancer cells.

In the context of the present invention, the term "tumor-associated antigen" or "tumor antigen" relates to proteins that are under normal conditions specifically expressed in a limited number of tissues and/or organs or in specific developmental stages, for example, the tumor-associated antigen may be under normal conditions specifically expressed in stomach tissue, preferably in the gastric mucosa, in reproductive organs, e.g., in testis, in trophoblastic tissue, e.g., in placenta, or in germ line cells, and are expressed or aberrantly expressed in one or more tumor or cancer tissues. In this context, "a limited number" preferably means not more than 3, more preferably not more than 2. The tumor-associated antigens in the context of the present invention include, for example, differentiation antigens, preferably cell type specific differentiation antigens, i.e., proteins that are under normal conditions specifically expressed in a certain cell type at a certain differentiation stage, cancer/testis antigens, i.e., proteins that are under normal conditions specifically expressed in testis and sometimes in placenta, and germ line specific antigens. In the context of the present invention, the tumor-associated antigen is preferably associated with the cell surface of a cancer cell and is preferably not or only rarely expressed in normal tissues. Preferably, the tumor-associated antigen or the aberrant expression of the tumor-associated antigen identifies cancer cells. In the context of the present invention, the tumor-associated antigen that is expressed by a cancer cell in a subject, e.g., a patient suffering from a cancer disease, is preferably a self-protein in said subject. In preferred embodiments, the tumor-associated antigen in the context of the present invention is expressed under normal conditions specifically in a tissue or organ that is non-essential, i.e., tissues or organs which when damaged by the immune system do not lead to death of the subject, or in organs or structures of the body which are not or only hardly accessible by the immune system. Preferably, the amino acid sequence of the tumor-associated antigen is identical between the tumor-associated antigen which is expressed in normal tissues and the tumor-associated antigen which is expressed in cancer tissues. Preferably, a tumor-associated antigen is presented by a cancer cell in which it is expressed.

Various aspects of the invention involve the tumor-associated antigen CLDN18.2 and the present invention may involve the stimulation or provision of an anti-tumor CTL reaction against cancer cells expressing said tumor-associated antigen and preferably presenting said tumor-associated antigen with class I MHC.

Claudins are a family of proteins that are the most important components of tight junctions, where they establish the paracellular barrier that controls the flow of molecules in the intercellular space between cells of an epithelium. Claudins are transmembrane proteins spanning the membrane 4 times with the N-terminal and the C-terminal end both located in the cytoplasm. The first extracellular loop or domain, termed EC1 or ECL1, consists on average of 53 amino acids, and the second extracellular loop or domain, termed EC2 or ECL2, consists of around 24 amino acids. Cell surface proteins of the claudin family, such as CLDN18.2, are expressed in tumors of various origins, and are particularly suited as target structures in connection with antibody-mediated cancer immunotherapy due to their selective expression (no expression in a toxicity relevant normal tissue) and localization to the plasma membrane.

CLDN18.2 is selectively expressed in normal tissues in differentiated epithelial cells of the gastric mucosa. CLDN18.2 is expressed in cancers of various origins such as pancreatic carcinoma, esophageal carcinoma, gastric carcinoma, bronchial carcinoma, breast carcinoma, and ENT tumors. CLDN18.2 is a valuable target for the prevention and/or treatment of primary tumors, such as gastric cancer, esophageal cancer, pancreatic cancer, lung cancer such as non small cell lung cancer (NSCLC), ovarian cancer, colon cancer, hepatic cancer, head-neck cancer, and cancers of the gallbladder, and metastases thereof, in particular gastric cancer metastasis such as Krukenberg tumors, peritoneal metastasis, and lymph node metastasis.

The term "CLDN" as used herein means claudin and includes CLDN18.2. Preferably, a claudin is a human claudin.

The term "CLDN18" relates to claudin 18 and includes any variants, including claudin 18 splice variant 1 (claudin 18.1 (CLDN18.1)) and claudin 18 splice variant 2 (claudin 18.2 (CLDN18.2)).

The term "CLDN18.2" preferably relates to human CLDN18.2, and, in particular, to a protein comprising, preferably consisting of the amino acid sequence according to SEQ ID NO: 1 of the sequence listing or a variant of said amino acid sequence. The first extracellular loop or domain of CLDN18.2 preferably comprises amino acids 27 to 81, more preferably amino acids 29 to 78 of the amino acid sequence shown in SEQ ID NO: 1. The second extracellular loop or domain of CLDN18.2 preferably comprises amino acids 140 to 180 of the amino acid sequence shown in SEQ ID NO: 1. Said first and second extracellular loops or domains preferably form the extracellular portion or domain of CLDN18.2.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

According to the various aspects of the invention, the aim is preferably to induce or determine an immune response against cancer cells expressing CLDN18.2 and preferably being characterized by presentation of CLDN18.2, and to diagnose, treat or prevent a cancer disease involving cells expressing CLDN18.2. Preferably the immune response involves the stimulation of an anti-CLDN18.2 CTL response against cancer cells expressing CLDN18.2 and preferably presenting CLDN18.2 with class I MHC.

According to the invention, the term "CLDN18.2-expressing cancer" or "CLDN18.2-positive cancer" means a cancer involving cancer cells expressing CLDN18.2, preferably on the surface of said cancer cells. Alternatively or additionally, said cancer cells expressing CLDN18.2 present CLDN18.2 in the context of MHC molecules. Cancer cells presenting CLDN18.2 in the context of MHC molecules can be targeted by immunoreactive cells carrying T cell receptors while cancer cells expressing CLDN18.2 on the surface can be targeted by immunoreactive cells carrying artificial T cell receptors.

"Cell surface" is used in accordance with its normal meaning in the art, and thus includes the outside of the cell which is accessible to binding by proteins and other molecules CLDN18.2 is expressed on the surface of cells if it is located at the surface of said cells and is accessible to binding by CLDN18.2-specific antibodies added to the cells.

The term "extracellular portion" or "exodomain" in the context of the present invention refers to a part of a molecule such as a protein that is facing the extracellular space of a cell and preferably is accessible from the outside of said cell, e.g., by antigen-binding molecules such as antibodies located outside the cell. Preferably, the term refers to one or more extracellular loops or domains or a fragment thereof.

The term "portion" refers to a fraction. With respect to a particular structure such as an amino acid sequence or protein the term "portion" thereof may designate a continuous or a discontinuous fraction of said structure. Preferably, a portion of an amino acid sequence comprises at least 1%, at least 5%, at least 10%, at least 20%, at least 30%, preferably at least 40%, preferably at least 50%, more preferably at least 60%, more preferably at least 70%, even more preferably at least 80%, and most preferably at least 90% of the amino acids of said amino acid sequence. Preferably, if the portion is a discontinuous fraction said discontinuous fraction is composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

The terms "part" and "fragment" are used interchangeably herein and refer to a continuous element. For example, a part of a structure such as an amino acid sequence or protein refers to a continuous element of said structure. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. In the context of the present invention, a "part" of a structure such as an amino acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence. A part or fragment of a protein sequence preferably comprises a sequence of at least 6, in particular at least 8, at least 12, at least 15, at least 20, at least 30, at least 50, or at least 100 consecutive amino acids of the protein sequence. Portions, parts or fragments as discussed above are encompassed by the term "variant" used herein.

According to the invention, CLDN18.2 is not substantially expressed in a cell if the level of expression is lower compared to expression in stomach cells or stomach tissue. Preferably, the level of expression is less than 10%, preferably less than 5%, 3%, 2%, 1%, 0.5%, 0.1% or 0.05% of the expression in stomach cells or stomach tissue or even lower. Preferably, CLDN18.2 is not substantially expressed in a cell if the level of expression exceeds the level of expression in non-cancerous tissue other than stomach by no more than 2-fold, preferably 1.5-fold, and preferably does not exceed the level of expression in said non-cancerous tissue. Preferably, CLDN18.2 is not substantially expressed in a cell if the level of expression is below the detection limit and/or if the level of expression is too low to allow binding by CLDN18.2-specific antibodies added to the cells.

According to the invention, CLDN18.2 is expressed in a cell if the level of expression exceeds the level of expression in non-cancerous tissue other than stomach preferably by more than 2-fold, preferably 10-fold, 100-fold, 1000-fold, or 10000-fold. Preferably, CLDN18.2 is expressed in a cell if the level of expression is above the detection limit and/or if the level of expression is high enough to allow binding by CLDN18.2-specific antibodies added to the cells. Preferably, CLDN18.2 expressed in a cell is expressed or exposed on the surface of said cell.

"Target cell" shall mean a cell which is a target for an immune response such as a cellular immune response. Target cells include cells that present an antigen or an antigen epitope, i.e. a peptide fragment derived from an antigen, and include any undesirable cell such as a cancer cell. In preferred embodiments, the target cell is a cell expressing CLDN18.2 which preferably is present on the cell surface and/or presented with class I MHC.

The term "epitope" refers to an antigenic determinant in a molecule such as an antigen, i.e., to a part in or fragment of the molecule that is recognized by the immune system, for example, that is recognized by a T cell, in particular when presented in the context of MHC molecules. An epitope of a protein such as a tumor-associated antigen preferably comprises a continuous or discontinuous portion of said protein and is preferably between 5 and 100, preferably between 5 and 50, more preferably between 8 and 30, most preferably between 10 and 25 amino acids in length, for example, the epitope may be preferably 9, 10, 11, 12, 13, 14, 15, 16, 17, 18, 19, 20, 21, 22, 23, 24, or 25 amino acids in length. It is particularly preferred that the epitope in the context of the present invention is a T cell epitope.

Terms such as "epitope", "antigen fragment", "antigen peptide" or "immunogenic peptide" are used interchangeably herein and preferably relate to an incomplete representation of an antigen which is preferably capable of eliciting an immune response against the antigen or a cell expressing or comprising and preferably presenting the antigen. Preferably, the terms relate to an immunogenic portion of an antigen. Preferably, it is a portion of an antigen that is recognized (i.e., specifically bound) by a T cell receptor, in particular if presented in the context of MHC molecules. Certain preferred immunogenic portions bind to an MHC class I or class II molecule such as on the surface of a cell and thus are MHC binding peptides. As used herein, a peptide is said to "bind to" an MHC class I or class II molecule if such binding is detectable using any assay known in the art.

Preferably, the peptides disclosed herein comprising an amino acid sequence selected from the group consisting of SEQ ID NOs: 2, 3, 4, 5, 6 and 7 or a variant of said amino acid sequence are capable of stimulating an immune response, preferably a cellular response against CLDN18.2 or cells characterized by expression of CLDN18.2 and preferably characterized by presentation of CLDN18.2. Preferably, such peptide is capable of stimulating a cellular response against a cell characterized by presentation of CLDN18.2 with class I MHC and preferably is capable of stimulating CLDN18.2-responsive CTL. Preferably, the peptides according to the invention are MHC class I and/or class II presented peptides or can be processed to produce MHC class I and/or class II presented peptides. Preferably, the sequence bound to the MHC molecule is selected from SEQ ID NOs: 2, 3, 4, 5, 6 and 7.

If an antigen peptide is to be presented directly, i.e. without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably the sequence of an antigen peptide which is to be presented directly substantially corresponds and is preferably completely identical to a sequence selected from SEQ ID NOs: 2, 3, 4, 5, 6 and 7.

If an antigen peptide is to be presented following processing, in particular following cleavage, the peptide produced by processing has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length. Preferably, the sequence of the peptide which is to be presented following processing substantially corresponds and is preferably completely identical to a sequence selected from SEQ ID NOs: 2, 3, 4, 5, 6 and 7. Thus, an antigen peptide according to the invention in one embodiment comprises a sequence selected from SEQ ID NOs: 2, 3, 4, 5, 6 and 7 and following processing of the antigen peptide makes up a sequence selected from SEQ ID NOs: 2, 3, 4, 5, 6 and 7.

Peptides having amino acid sequences substantially corresponding to a sequence of a peptide which is presented by MHC molecules may differ at one or more residues that are not essential for TCR recognition of the peptide as presented by the MHC, or for peptide binding to MHC. Such substantially corresponding peptides preferably are also capable of stimulating an antigen-specific cellular response such as antigen-specific CTL. Peptides having amino acid sequences differing from a presented peptide at residues that do not affect TCR recognition but improve the stability of binding to MHC may improve the immunogenicity of the antigen peptide, and may be referred to herein as "optimized peptides". Using existing knowledge about which of these residues may be more likely to affect binding either to the MHC or to the TCR, a rational approach to the design of substantially corresponding peptides may be employed. Resulting peptides that are functional are contemplated as antigen peptides. Sequences as discussed above are encompassed by the term "variant" used herein.

"Antigen processing" refers to the degradation of an antigen into procession products, which are fragments of said antigen (e.g., the degradation of a protein into peptides) and the association of one or more of these fragments (e.g., via binding) with MHC molecules for presentation by cells, preferably antigen presenting cells to specific T cells.

An antigen-presenting cell (APC) is a cell that displays antigen in the context of major histocompatibility complex (MHC) on its surface. T cells may recognize this complex using their T cell receptor (TCR). Antigen-presenting cells process antigens and present them to T cells.

Professional antigen-presenting cells are very efficient at internalizing antigen, either by phagocytosis or by receptor-mediated endocytosis, and then displaying a fragment of the antigen, bound to a class II MHC molecule, on their membrane. The T cell recognizes and interacts with the antigen-class II MHC molecule complex on the membrane of the antigen-presenting cell. An additional co-stimulatory signal is then produced by the antigen-presenting cell, leading to activation of the T cell. The expression of co-stimulatory molecules is a defining feature of professional antigen-presenting cells. Antigen-presenting cells include professional antigen-presenting cells and non-professional antigen-presenting cells.

The main types of professional antigen-presenting cells are dendritic cells, which have the broadest range of antigen presentation, and are probably the most important antigen-presenting cells, macrophages, B-cells, monocytes and certain activated epithelial cells.

Non-professional antigen-presenting cells do not constitutively express the MHC class II proteins required for interaction with naive T cells; these are expressed only upon stimulation of the non-professional antigen-presenting cells by certain cytokines such as IFNγ.

Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity.

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFa to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which can be used as a simple way to discriminate between two well characterized phenotypes. However, this nomenclature should not be construed to exclude all possible intermediate stages of differentiation.

Immature dendritic cells are characterized as antigen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g. CD54 and CD11) and costimulatory molecules (e.g., CD40, CD80, CD86 and 4-1 BB).

Dendritic cell maturation is referred to as the status of dendritic cell activation at which such antigen-presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD40L, and substances released from cells undergoing stressful cell death. The dendritic cells can be derived by culturing bone marrow cells in vitro with cytokines, such as granulocyte-macrophage colony-stimulating factor (GM-CSF) and tumor necrosis factor alpha.

Cells such as antigen presenting cells or target cells can be loaded with MHC class I presented peptides by exposing, i.e. pulsing, the cells with the peptide or transducing the cells with nucleic acid, preferably RNA, encoding a peptide or protein comprising the peptide to be presented, e.g. a nucleic acid encoding the antigen.

In some embodiments, a pharmaceutical composition of the invention comprises an antigen presenting cell loaded with antigen peptide. In this respect, protocols may rely on in vitro culture/differentiation of dendritic cells manipulated in such a way that they artificially present antigen peptide. Production of genetically engineered dendritic cells may involve introduction of nucleic acids encoding antigens or antigen peptides into dendritic cells. Transfection of dendritic cells with mRNA is a promising antigen-loading technique of stimulating strong antitumor immunity. Such transfection may take place ex vivo, and a pharmaceutical composition comprising such transfected cells may then be used for therapeutic purposes. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., Immunology and cell Biology 75: 456-460, 1997. Antigen loading of dendritic cells may be achieved by incubating dendritic cells or progenitor cells with antigen, DNA (naked or within a plasmid vector) or RNA; or with antigen-expressing recombinant bacteria or viruses (e.g., vaccinia, fowlpox, adenovirus or lentivirus vectors).

The term "immunogenicity" relates to the relative efficiency of an antigen to induce an immune reaction.

The term "immune effector functions" in the context of the present invention includes any functions mediated by components of the immune system that result, for example, in the killing of tumor cells, or in the inhibition of tumor growth and/or inhibition of tumor development, including inhibition of tumor dissemination and metastasis. Preferably, the immune effector functions in the context of the present invention are T cell mediated effector functions. Such functions comprise in the case of a helper T cell ($CD4^+$ T cell) the recognition of an antigen or an antigen peptide derived from an antigen in the context of MHC class II molecules by T cell receptors, the release of cytokines and/or the activation of $CD8^+$ lymphocytes (CTLs) and/or B-cells, and in the case of CTL the recognition of an antigen or an antigen peptide derived from an antigen in the context of MHC class I molecules by T cell receptors, the elimination of cells presented in the context of MHC class I molecules, i.e., cells characterized by presentation of an antigen with class I MHC, for example, via apoptosis or perforin-mediated cell lysis, production of cytokines such as IFN-γ and TNF-α, and specific cytolytic killing of antigen expressing target cells.

The term "immunoreactive cell" or "immune effector cell" in the context of the present invention relates to a cell which exerts effector functions during an immune reaction. An "immunoreactive cell" preferably is capable of binding an antigen such as an antigen expressed on the surface of a cell or a cell characterized by presentation of an antigen or an antigen peptide derived from an antigen and mediating an immune response. For example, such cells secrete cytokines and/or chemokines, kill microbes, secrete antibodies, recognize infected or cancerous cells, and optionally eliminate such cells. For example, immunoreactive cells comprise T cells (cytotoxic T cells, helper T cells, tumor infiltrating T cells), B cells, natural killer cells, neutrophils, macrophages, and dendritic cells. Preferably, in the context of the present invention, "immunoreactive cells" are T cells, preferably $CD4^+$ and/or $CD8^+$ T cells.

Preferably, an "immunoreactive cell" recognizes an antigen or an antigen peptide derived from an antigen with some degree of specificity, in particular if presented in the context of MHC molecules such as on the surface of antigen presenting cells or diseased cells such as cancer cells. Preferably, said recognition enables the cell that recognizes an antigen or an antigen peptide derived from said antigen to be responsive or reactive. If the cell is a helper T cell ($CD4^+$ T cell) bearing receptors that recognize an antigen or an antigen peptide derived from an antigen in the context of MHC class II molecules such responsiveness or reactivity may involve the release of cytokines and/or the activation of $CD8^+$ lymphocytes (CTLs) and/or B-cells. If the cell is a CTL such responsiveness or reactivity may involve the elimination of cells presented in the context of MHC class I molecules, i.e., cells characterized by presentation of an antigen with class I MHC, for example, via apoptosis or perforin-mediated cell lysis. According to the invention, CTL responsiveness may include sustained calcium flux, cell division, production of cytokines such as IFN-γ and TNF-α, up-regulation of activation markers such as CD44 and CD69, and specific cytolytic killing of antigen expressing target cells. CTL responsiveness may also be determined using an artificial reporter that accurately indicates CTL responsiveness. Such CTL that recognizes an antigen or an antigen peptide derived from an antigen and are responsive or reactive are also termed "antigen-responsive CTL" herein. If the cell is a B cell such responsiveness may involve the release of immunoglobulins.

According to the invention, the term "immunoreactive cell" also includes a cell which can mature into an immune cell (such as T cell, in particular T helper cell, or cytolytic T cell) with suitable stimulation. Immunoreactive cells comprise $CD34^+$ hematopoietic stem cells, immature and mature T cells and immature and mature B cells. If production of cytolytic or T helper cells recognizing an antigen is desired, the immunoreactive cell is contacted with a cell presenting an antigen or antigen peptide under conditions which favor production, differentiation and/or selection of cytolytic T cells and of T helper cells. The differentiation of T cell precursors into a cytolytic T cell, when exposed to an antigen, is similar to clonal selection of the immune system.

A "lymphoid cell" is a cell which, optionally after suitable modification, e.g. after transfer of a T cell receptor, is capable of producing an immune response such as a cellular immune response, or a precursor cell of such cell, and includes lymphocytes, preferably T lymphocytes, lymphoblasts, and plasma cells. A lymphoid cell may be an immunoreactive cell as described herein. A preferred lymphoid cell is a T cell lacking endogenous expression of a T cell receptor and which can be modified to express such T cell receptor on the cell surface.

The terms "T cell" and "T lymphocyte" are used interchangeably herein and include T helper cells (CD4+ T cells) and cytotoxic T cells (CTLs, CD8+ T cells) which comprise cytolytic T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptors (TCR). The thymus is the principal organ responsible for the T cell's maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 protein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein at their surface. These cells recognize their targets by binding to antigen associated with MHC class I, which is present on the surface of nearly every cell of the body.

A majority of T cells have a T cell receptor (TCR) existing as a complex of several proteins. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

The structure of the T cell receptor is very similar to immunoglobulin Fab fragments, which are regions defined as the combined light and heavy chain of an antibody arm. Each chain of the TCR is a member of the immunoglobulin superfamily and possesses one N-terminal variable (V) domain, one constant (C) domain, a transmembrane/cell membrane-spanning region, and a short cytoplasmic tail at the C-terminal end.

According to the invention, the term "variable region of a T cell receptor" relates to the variable domains of the TCR chains.

The variable region of both the TCR α-chain and β-chain have three hypervariable or complementarity determining regions (CDRs), whereas the variable region of the β-chain has an additional area of hypervariability (HV4) that does not normally contact antigen and therefore is not considered a CDR. CDR3 is the main CDR responsible for recognizing processed antigen, although CDR1 of the α-chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens.

According to the invention, the term "at least one of the CDR sequences" preferably means at least the CDR3 sequence. The term "CDR sequences of a T cell receptor chain" preferably relates to CDR1, CDR2 and CDR3 of the α-chain or β-chain of a T cell receptor.

The constant domain of the TCR domain consists of short connecting sequences in which a cysteine residue forms disulfide bonds, which forms a link between the two chains.

All T cells originate from hematopoietic stem cells in the bone marrow. Hematopoietic progenitors derived from hematopoietic stem cells populate the thymus and expand by cell division to generate a large population of immature thymocytes. The earliest thymocytes express neither CD4 nor CD8, and are therefore classed as double-negative (CD4-CD8-) cells. As they progress through their development they become double-positive thymocytes (CD4+ CD8+), and finally mature to single-positive (CD4+CD8- or CD4-CD8+) thymocytes that are then released from the thymus to peripheral tissues.

The first signal in activation of T cells is provided by binding of the T cell receptor to a short peptide presented by the major histocompatibility complex (MHC) on another cell. This ensures that only a T cell with a TCR specific to that peptide is activated. The partner cell is usually a professional antigen presenting cell (APC), usually a dendritic cell in the case of naïve responses, although B cells and macrophages can be important APCs. The peptides presented to CD8+ T cells by MHC class I molecules are 8-10 amino acids in length; the peptides presented to CD4+ T cells by MHC class II molecules are longer, as the ends of the binding cleft of the MHC class II molecule are open.

T cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system. Alternatively, T cells may be derived from related or unrelated humans, non-human animals, cell lines or cultures. A "sample comprising T cells" may, for example, be peripheral blood mononuclear cells (PBMC).

T cells may be stimulated with antigen, peptide, nucleic acid and/or antigen presenting cells (APCs) that express an antigen. Such stimulation is performed under conditions and for a time sufficient to permit the generation of T cells that are specific for an antigen, a peptide and/or cells presenting an antigen or a peptide.

Specific activation of CD4+ or CD8+ T cells may be detected in a variety of ways. Methods for detecting specific T cell activation include detecting the proliferation of T cells, the production of cytokines (e.g., lymphokines), or the generation of cytolytic activity. For CD4+ T cells, a preferred method for detecting specific T cell activation is the detection of the proliferation of T cells. For CD8+ T cells, a preferred method for detecting specific T cell activation is the detection of the generation of cytolytic activity.

In order to generate CD8+ T cell lines, antigen-presenting cells, preferably autologous antigen-presenting cells, transfected with a nucleic acid which produces the antigen may be used as stimulator cells.

Nucleic acids such as RNA encoding T cell receptor (TCR) chains may be introduced into lymphoid cells such as T cells or other cells with lytic potential. In a suitable embodiment, the TCR α- and β-chains are cloned out from an antigen-specific T cell line and used for adoptive T cell therapy. In this respect, the present invention provides T cell receptors specific for CLDN18.2 or CLDN18.2 peptides disclosed herein. In general, this aspect of the invention relates to T cell receptors which recognize or bind CLDN18.2 peptides presented in the context of MHC. The nucleic acids encoding α- and β-chains of a T cell receptor, e.g. a T cell receptor provided according to the present invention, may be contained on separate nucleic acid molecules such as expression vectors or alternatively, on a single nucleic acid molecule. Accordingly, the term "a nucleic acid encoding a T cell receptor" or similar terms relate to nucleic acid molecules encoding the T cell receptor chains on the same or preferably on different nucleic acid molecules.

The term "immunoreactive cell reactive with a peptide" relates to an immunoreactive cell which when it recognizes the peptide, in particular if presented in the context of MHC molecules such as on the surface of antigen presenting cells or diseased cells such as cancer cells, exerts effector functions of immunoreactive cells as described above.

The term "T cell receptor reactive with a peptide" relates to a T cell receptor which when present on an immunoreactive cell recognizes the peptide, in particular if presented in the context of MHC molecules such as on the surface of antigen presenting cells or diseased cells such as cancer cells, such that the immunoreactive cell exerts effector functions of immunoreactive cells as described above.

The term "antigen-reactive T cell" or similar terms relate to a T cell which recognizes an antigen if presented in the context of MHC molecules such as on the surface of antigen presenting cells or diseased cells such as cancer cells and exerts effector functions of T cells as described above.

The term "antigen-specific lymphoid cell" relates to a lymphoid cell which, in particular when provided with an antigen-specific T cell receptor, recognizes the antigen if presented in the context of MHC molecules such as on the surface of antigen presenting cells or diseased cells such as cancer cells and preferably exerts effector functions of T cells as described above. T cells and other lymphoid cells are considered to be specific for antigen if the cells kill target cells expressing an antigen and/or presenting an antigen peptide. T cell specificity may be evaluated using any of a variety of standard techniques, for example, within a chromium release assay or proliferation assay. Alternatively, synthesis of lymphokines (such as interferon-γ) can be measured The term "major histocompatibility complex" and the abbreviation "MHC" include MHC class I and MHC class II molecules and relate to a complex of genes which occurs in all vertebrates. MHC proteins or molecules are important for signaling between lymphocytes and antigen presenting cells or diseased cells in immune reactions, wherein the MHC proteins or molecules bind peptides and present them for recognition by T cell receptors. The proteins encoded by the MHC are expressed on the surface of cells, and display both self antigens (peptide fragments from the cell itself) and nonself antigens (e.g., fragments of invading microorganisms) to a T cell.

The MHC region is divided into three subgroups, class I, class II, and class III. MHC class I proteins contain an α-chain and β2-microglobulin (not part of the MHC encoded by chromosome 15). They present antigen fragments to cytotoxic T cells. On most immune system cells, specifically on antigen-presenting cells, MHC class II proteins contain α- and β-chains and they present antigen fragments to T-helper cells. MHC class III region encodes for other immune components, such as complement components and some that encode cytokines.

In humans, genes in the MHC region that encode antigen-presenting proteins on the cell surface are referred to as human leukocyte antigen (HLA) genes. However the abbreviation MHC is often used to refer to HLA gene products. HLA genes include the nine so-called classical MHC genes: HLA-A, HLA-B, HLA-C, HLA-DPA1, HLA-DPB1, HLA-DQA1, HLA-DQB1, HLA-DRA, and HLA-DRB1.

In one preferred embodiment of all aspects of the invention an MHC molecule is an HLA molecule.

By "cell characterized by presentation of an antigen", "cell presenting an antigen", "antigen presented by a cell", "antigen presented" or similar expressions is meant a cell such as a diseased cell such as a cancer cell, or an antigen presenting cell presenting the antigen it expresses or a fragment derived from said antigen, e.g. by processing of the antigen, in the context of MHC molecules, in particular MHC Class I molecules. Similarly, the terms "disease characterized by presentation of an antigen" denotes a disease involving cells characterized by presentation of an antigen, in particular with class I MHC. Presentation of an antigen by a cell may be effected by transfecting the cell with a nucleic acid such as RNA encoding the antigen.

By "fragment of an antigen which is presented" or similar expressions is meant that the fragment can be presented by MHC class I or class II, preferably MHC class I, e.g. when added directly to antigen presenting cells. In one embodiment, the fragment is a fragment which is naturally presented by cells expressing an antigen.

Some therapeutic methods are based on a reaction of the immune system of a patient, which results in a lysis of diseased cells which present an antigen with class I MHC. In this connection, for example autologous cytotoxic T lymphocytes specific for a complex of an antigen peptide and an MHC molecule may be administered to a patient having a disease. The production of such cytotoxic T lymphocytes in vitro is known. An example of a method of differentiating T cells can be found in WO-A-9633265. Generally, a sample containing cells such as blood cells is taken from the patient and the cells are contacted with a cell which presents the complex and which can cause propagation of cytotoxic T lymphocytes (e.g. dendritic cells). The target cell may be a transfected cell such as a COS cell. These transfected cells present the desired complex on their surface and, when contacted with cytotoxic T lymphocytes, stimulate propagation of the latter. The clonally expanded autologous cytotoxic T lymphocytes are then administered to the patient.

In another method of selecting cytotoxic T lymphocytes, fluorogenic tetramers of MHC class I molecule/peptide complexes are used for obtaining specific clones of cytotoxic T lymphocytes (Altman et al. (1996), Science 274:94-96; Dunbar et al. (1998), Curr. Biol. 8:413-416, 1998).

Furthermore, cells presenting the desired complex (e.g. dendritic cells) may be combined with cytotoxic T lymphocytes of healthy individuals or another species (e.g. mouse) which may result in propagation of specific cytotoxic T lymphocytes with high affinity. The high affinity T cell receptor of these propagated specific T lymphocytes may be cloned and optionally humanized to a different extent, and the T cell receptors thus obtained then transduced via gene transfer, for example using retroviral vectors, into T cells of patients. Adoptive transfer may then be carried out using these genetically altered T lymphocytes (Stanislawski et al. (2001), Nat Immunol. 2:962-70; Kessels et al. (2001), Nat Immunol. 2:957-61.

Cytotoxic T lymphocytes may also be generated in vivo in a manner known per se. One method uses nonproliferative cells expressing an MHC class I/peptide complex. The cells used here will be those which usually express the complex, such as irradiated tumor cells or cells transfected with one or both genes necessary for presentation of the complex (i.e. the antigenic peptide and the presenting MHC molecule). Another preferred form is the introduction of an antigen in the form of recombinant RNA which may be introduced into cells by liposomal transfer or by electroporation, for example. The resulting cells present the complex of interest and are recognized by autologous cytotoxic T lymphocytes which then propagate.

A similar effect can be achieved by combining an antigen or an antigen peptide with an adjuvant in order to make incorporation into antigen-presenting cells in vivo possible. The antigen or antigen peptide may be represented as protein, as DNA (e.g. within a vector) or as RNA. The antigen may be processed to produce a peptide partner for the MHC molecule, while a fragment thereof may be presented without the need for further processing. The latter is the case in particular, if these can bind to MHC molecules. Preference is given to administration forms in which the complete antigen is processed in vivo by a dendritic cell, since this may also produce T helper cell responses which are needed for an effective immune response (Ossendorp et al., Immunol Lett. (2000), 74:75-9; Ossendorp et al. (1998), J. Exp. Med. 187:693-702. In general, it is possible to administer an effective amount of the tumor-associated antigen to a patient by intradermal injection, for example. However, injection may also be carried out intranodally into a lymph node (Maloy et al. (2001), Proc Natl Acad Sci USA 98:3299-303).

According to the invention the term "artificial T cell receptor" is synonymous with the terms "chimeric T cell receptor" and "chimeric antigen receptor (CAR)".

These terms relate to engineered receptors, which confer an arbitrary specificity such as the specificity of a monoclonal antibody onto an immune effector cell such as a T cell. In this way, a large number of cancer-specific T cells can be generated for adoptive cell transfer. Thus, an artificial T cell receptor may be present on T cells, e.g. instead of or in addition to the T cell's own T cell receptor. Such T cells do not necessarily require processing and presentation of an antigen for recognition of the target cell but rather may recognize preferably with specificity any antigen present on a target cell. Preferably, said artificial T cell receptor is expressed on the surface of the cells. For the purpose of the present invention T cells comprising an artificial T cell receptor are comprised by the term "T cell" as used herein.

In one embodiment, a single-chain variable fragment (scFv) derived from a monoclonal antibody is fused to CD3-zeta transmembrane and endodomain. Such molecules result in the transmission of a zeta signal in response to recognition by the scFv of its antigen target on a target cell and killing of the target cell that expresses the target antigen. Antigen recognition domains which also may be used include among others T-cell receptor (TCR) alpha and beta single chains. In fact almost anything that binds a given target with high affinity can be used as an antigen recognition domain.

Following antigen recognition, receptors cluster and a signal is transmitted to the cell. In this respect, a "T cell signaling domain" is a domain, preferably an endodomain, which transmits an activation signal to the T cell after antigen is bound. The most commonly used endodomain component is CD3-zeta.

Adoptive cell transfer therapy with CAR-engineered T cells expressing chimeric antigen receptors is a promising anti-cancer therapeutic as CAR-modified T cells can be engineered to target virtually any tumor antigen. For example, patient's T cells may be genetically engineered to express CARs specifically directed towards antigens on the patient's tumor cells, then infused back into the patient.

According to the invention an artificial T cell receptor may replace the function of a T cell receptor as described above and, in particular, may confer reactivity such as cytolytic activity to a cell such as a T cell as described above. However, in contrast to the binding of the T cell receptor to an antigen peptide-MHC complex as described above, an artificial T cell receptor may bind to an antigen, in particular expressed on the cell surface.

The T-cell surface glycoprotein CD3-zeta chain is a protein that in humans is encoded by the CD247 gene. CD3-zeta together with T-cell receptor alpha/beta and gamma/delta heterodimers and CD3-gamma, -delta, and -epsilon, forms the T-cell receptor-CD3 complex. The zeta chain plays an important role in coupling antigen recognition to several intracellular signal-transduction pathways. The term "CD3-zeta" preferably relates to human CD3-zeta, and, in particular, to a protein comprising, preferably consisting of the amino acid sequence of SEQ ID NO: 40 of the sequence listing or a variant of said amino acid sequence.

CD28 (Cluster of Differentiation 28) is one of the molecules expressed on T cells that provide co-stimulatory signals, which are required for T cell activation. CD28 is the receptor for CD80 (B7.1) and CD86 (B7.2). Stimulation through CD28 in addition to the T cell receptor (TCR) can provide a potent co-stimulatory signal to T cells for the production of various interleukins (IL-6 in particular). The term "CD28" preferably relates to human CD28, and, in particular, to a protein comprising, preferably consisting of the amino acid sequence of SEQ ID NO: 39 of the sequence listing or a variant of said amino acid sequence.

According to the invention, CARs may generally comprise three domains.

The first domain is the binding domain which recognizes and binds CLDN18.2.

The second domain is the co-stimulation domain. The co-stimulation domain serves to enhance the proliferation and survival of the cytotoxic lymphocytes upon binding of the CAR to a targeted moiety. The identity of the co-stimulation domain is limited only in that it has the ability to enhance cellular proliferation and survival upon binding of the targeted moiety by the CAR. Suitable co-stimulation domains include CD28, CD137 (4-1BB), a member of the tumor necrosis factor (TNF) receptor family, CD134 (OX40), a member of the TNFR-superfamily of receptors, and CD278 (ICOS), a CD28-superfamily co-stimulatory molecule expressed on activated T cells. The skilled person will understand that sequence variants of these noted co-stimulation domains can be used without adversely impacting the invention, where the variants have the same or similar activity as the domain on which they are modeled. Such variants will have at least about 80% sequence identity to the amino acid sequence of the domain from which they are derived. In some embodiments of the invention, the CAR constructs comprise two co-stimulation domains. While the particular combinations include all possible variations of the four noted domains, specific examples include CD28+ CD137 (4-1BB) and CD28+CD134 (OX40).

The third domain is the activation signaling domain (or T cell signaling domain). The activation signaling domain serves to activate cytotoxic lymphocytes upon binding of the CAR to CLDN18.2. The identity of the activation signaling domain is limited only in that it has the ability to induce activation of the selected cytotoxic lymphocyte upon binding of the CLDN18.2 by the CAR. Suitable activation signaling domains include the T cell CD3[zeta] chain and Fc receptor [gamma]. The skilled artisan will understand that sequence variants of these noted activation signaling domains can be used without adversely impacting the invention, where the variants have the same or similar activity as the domain on which they are modeled. Such variants will have at least about 80% sequence identity to the amino acid sequence of the domain from which they are derived.

The CARs of the present invention may comprise the three domains, together in the form of a fusion protein. Such fusion proteins will generally comprise a binding domain, one or more co-stimulation domains, and an activation signaling domain, linked in a N-terminal to C-terminal direction. However, the CARs of the present invention are not limited to this arrangement and other arrangements are acceptable and include a binding domain, an activation signaling domain, and one or more co-stimulation domains. It will be understood that because the binding domain must be free to bind CLDN18.2, the placement of the binding domain in the fusion protein will generally be such that display of the region on the exterior of the cell is achieved. In the same manner, because the co-stimulation and activation signaling domains serve to induce activity and proliferation of the cytotoxic lymphocytes, the fusion protein will generally display these two domains in the interior of the cell. The CARs may include additional elements, such as a signal peptide to ensure proper export of the fusion protein to the cells surface, a transmembrane domain to ensure the fusion protein is maintained as an integral membrane protein, and a hinge domain (or spacer region) that imparts flexibility to the binding domain and allows strong binding to CLDN18.2.

The cells used in connection with the CAR system of the present invention are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target tumor cells. The cytotoxic lymphocytes will preferably be autologous cells, although heterologous cells or allogenic cells can be used.

According to the invention, a "reference" such as a reference sample or reference organism may be used to correlate and compare the results obtained in the methods of the invention from a test sample or test organism. Typically the reference organism is a healthy organism, in particular an organism which does not suffer from a disease such as a cancer disease. A "reference value" or "reference level" can be determined from a reference empirically by measuring a sufficiently large number of references. Preferably the reference value is determined by measuring at least 2, preferably at least 3, preferably at least 5, preferably at least 8, preferably at least 12, preferably at least 20, preferably at least 30, preferably at least 50, or preferably at least 100 references.

According to the invention, the term "binding agent" includes any compound that has a binding capacity to a target. Preferably, such binding agent comprises at least one binding domain for the target. The term includes molecules such as antibodies and antibody fragments, bispecific or multispecific molecules, chimeric antigen receptors (CARs) and all artificial binding molecules (scaffolds) having a binding capacity to the target including but not limited to nanobodies, affibodies, anticalins, DARPins, monobodies, avimers, and microbodies. In one embodiment said binding is a specific binding.

The term "immunoglobulin" relates to proteins of the immunoglobulin superfamily, preferably to antigen receptors such as antibodies or the B cell receptor (BCR). The immunoglobulins are characterized by a structural domain, i.e., the immunoglobulin domain, having a characteristic immunoglobulin (Ig) fold. The term encompasses membrane bound immunoglobulins as well as soluble immunoglobulins. Membrane bound immunoglobulins are also termed surface immunoglobulins or membrane immunoglobulins, which are generally part of the BCR. Soluble immunoglobulins are generally termed antibodies. Immunoglobulins generally comprise several chains, typically two identical heavy chains and two identical light chains which are linked via disulfide bonds. These chains are primarily composed of immunoglobulin domains, such as the $V_L$ (variable light chain) domain, $C_L$ (constant light chain) domain, and the $C_H$ (constant heavy chain) domains $C_H1$, $C_H2$, $C_H3$, and $C_H4$. There are five types of mammalian immunoglobulin heavy chains, i.e., α, δ, ε, γ, and μ which account for the different classes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus. In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

The term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies and chimeric antibodies. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "monoclonal antibody" as used herein refers to a preparation of antibody molecules of single molecular composition. A monoclonal antibody displays a single binding specificity and affinity. In one embodiment, the monoclonal antibodies are produced by a hybridoma which includes a B cell obtained from a non-human animal, e.g., mouse, fused to an immortalized cell.

The term "recombinant antibody", as used herein, includes all antibodies that are prepared, expressed, created or isolated by recombinant means, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

The term "human antibody", as used herein, is intended to include antibodies having variable and constant regions derived from human germline immunoglobulin sequences. Human antibodies may include amino acid residues not encoded by human germline immunoglobulin sequences (e.g., mutations introduced by random or site-specific mutagenesis in vitro or by somatic mutation in vivo).

The term "humanized antibody" refers to a molecule having an antigen binding site that is substantially derived from an immunoglobulin from a non-human species, wherein the remaining immunoglobulin structure of the molecule is based upon the structure and/or sequence of a human immunoglobulin. The antigen binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g. modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However the definition is not limited to this particular example.

Antibodies may be derived from different species, including but not limited to mouse, rat, rabbit, guinea pig and human.

Antibodies described herein include IgA such as IgA1 or IgA2, IgG1, IgG2, IgG3, IgG4, IgE, IgM, and IgD antibodies. In various embodiments, the antibody is an IgG1 antibody, more particularly an IgG1, kappa or IgG1, lambda isotype (i.e. IgG1, κ, λ), an IgG2a antibody (e.g. IgG2a, κ, λ), an IgG2b antibody (e.g. IgG2b, κ, λ), an IgG3 antibody (e.g. IgG3, κ, λ) or an IgG4 antibody (e.g. IgG4, κ, λ).

The antibodies described herein are preferably isolated. An "isolated antibody" as used herein, is intended to refer to an antibody which is substantially free of other antibodies having different antigenic specificities (e.g., an isolated antibody that specifically binds to CLDN18.2 is substantially free of antibodies that specifically bind antigens other than CLDN18.2). An isolated antibody that specifically binds to an epitope, isoform or variant of human CLDN18.2 may, however, have cross-reactivity to other related antigens, e.g., from other species (e.g., CLDN18.2 species homologs). Moreover, an isolated antibody may be substantially free of other cellular material and/or chemicals. In one embodiment of the invention, a combination of "isolated" monoclonal antibodies relates to antibodies having different specificities and being combined in a well defined composition or mixture.

The terms "antigen-binding portion" of an antibody (or simply "binding portion") or "antigen-binding fragment" of an antibody (or simply "binding fragment") or similar terms refer to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) Fab fragments, monovalent fragments consisting of the VL, VH, CL and CH domains; (ii) F(ab')$_2$ fragments, bivalent fragments comprising two Fab fragments linked by a disulfide bridge at the hinge region; (iii) Fd fragments consisting of the VH and CH domains; (iv) Fv fragments consisting of the VL and VH domains of a single arm of an antibody, (v) dAb fragments (Ward et al., (1989) Nature 341: 544-546), which consist of a VH domain; (vi) isolated complementarity determining regions (CDR), and (vii) combinations of two or more isolated CDRs which may optionally be joined by a synthetic linker. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242: 423-426; and Huston et al. (1988) Proc. Natl. Acad. Sci. USA 85: 5879-5883). Such single chain antibodies are also intended to be encompassed within the term "antigen-binding fragment" of an antibody. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

According to the invention, the term "binding domain for CLDN18.2" includes and preferably relates to the antigen-binding portion of a CLDN18.2 antibody, i.e. an antibody which is directed against CLDN18.2 and is preferably specific for CLDN18.2.

The term "binding domain" characterizes in connection with the present invention a structure, e.g. of an antibody, which binds to/interacts with a given target structure/antigen/epitope. Thus, the binding domain according to the invention designates an "antigen-interaction-site".

All antibodies and derivatives of antibodies such as antibody fragments as described herein for the purposes of the invention are encompassed by the term "antibody".

Antibodies can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g. described in Spieker-Polet et al., Proc. Natl. Acad. Sci. U.S.A. 92:9348 (1995), see also Rossi et al., Am. J. Clin. Pathol. 124: 295 (2005)).

To generate antibodies, mice can be immunized with carrier-conjugated peptides derived from the antigen sequence, i.e. the sequence against which the antibodies are to be directed, an enriched preparation of recombinantly expressed antigen or fragments thereof and/or cells expressing the antigen, as described. Alternatively, mice can be immunized with DNA encoding the antigen or fragments thereof. In the event that immunizations using a purified or enriched preparation of the antigen do not result in antibodies, mice can also be immunized with cells expressing the antigen, e.g., a cell line, to promote immune responses.

The immune response can be monitored over the course of the immunization protocol with plasma and serum samples being obtained by tail vein or retroorbital bleeds. Mice with sufficient titers of immunoglobulin can be used for fusions. Mice can be boosted intraperitoneally or intravenously with antigen expressing cells 3 days before sacrifice and removal of the spleen to increase the rate of specific antibody secreting hybridomas.

To generate hybridomas producing monoclonal antibodies, splenocytes and lymph node cells from immunized mice can be isolated and fused to an appropriate immortalized cell line, such as a mouse myeloma cell line. The resulting hybridomas can then be screened for the production of antigen-specific antibodies. Individual wells can then be screened by ELISA for antibody secreting hybridomas. By Immunofluorescence and FACS analysis using antigen expressing cells, antibodies with specificity for the antigen can be identified. The antibody secreting hybridomas can be replated, screened again, and if still positive for monoclonal antibodies can be subcloned by limiting dilution. The stable subclones can then be cultured in vitro to generate antibody in tissue culture medium for characterization.

The ability of antibodies and other binding agents to bind an antigen can be determined using standard binding assays (e.g., ELISA, Western Blot, Immunofluorescence and flow cytometric analysis).

Antibodies and derivatives of antibodies are useful for providing binding domains such as antibody fragments, in particular for providing VL and VH regions.

A binding domain for CLDN18.2 which may be present within an artificial T cell receptor has the ability of binding to CLDN18.2, i.e. the ability of binding to an epitope present in CLDN18.2, preferably an epitope located within the extracellular domains of CLDN18.2, in particular the first extracellular loop, preferably amino acid positions 29 to 78 of CLDN18.2. In particular embodiments, a binding domain for CLDN18.2 binds to an epitope on CLDN18.2 which is not present on CLDN18.1. Most preferably, a binding domain for CLDN18.2 binds to an epitope on CLDN18.2 which is not present on a CLDN protein other than CLDN18.2.

A binding domain for CLDN18.2 preferably binds to CLDN18.2 but not to CLDN18.1. Preferably, a binding domain for CLDN18.2 is specific for CLDN18.2. Preferably, a binding domain for CLDN18.2 binds to CLDN18.2 expressed on the cell surface. In particular preferred embodiments, a binding domain for CLDN18.2 binds to native epitopes of CLDN18.2 present on the surface of living cells.

In a preferred embodiment, a binding domain for CLDN18.2 comprises a heavy chain variable region (VH) comprising an amino acid sequence selected from the group consisting of SEQ ID NOs: 20, 21, 22, 23, 24 and 25, or a fragment thereof, or a variant of said amino acid sequence or fragment.

In a preferred embodiment, a binding domain for CLDN18.2 comprises a light chain variable region (VL) comprising an amino acid sequence selected from the group consisting of SEQ ID NOs: 26, 27, 28, 29, 30, 31, 32, 33 and 34, or a fragment thereof, or a variant of said amino acid sequence or fragment.

In certain preferred embodiments, a binding domain for CLDN18.2 comprises a combination of heavy chain variable region (VH) and light chain variable region (VL) selected from the following possibilities (i) to (ix):
  (i) the VH comprises an amino acid sequence represented by SEQ ID NO: 20 or a fragment thereof and the VL comprises an amino acid sequence represented by SEQ ID NO: 27 or a fragment thereof,
  (ii) the VH comprises an amino acid sequence represented by SEQ ID NO: 21 or a fragment thereof and the VL comprises an amino acid sequence represented by SEQ ID NO: 26 or a fragment thereof,
  (iii) the VH comprises an amino acid sequence represented by SEQ ID NO: 22 or a fragment thereof and the VL comprises an amino acid sequence represented by SEQ ID NO: 28 or a fragment thereof,
  (iv) the VH comprises an amino acid sequence represented by SEQ ID NO: 24 or a fragment thereof and the VL comprises an amino acid sequence represented by SEQ ID NO: 31 or a fragment thereof,
  (v) the VH comprises an amino acid sequence represented by SEQ ID NO: 23 or a fragment thereof and the VL comprises an amino acid sequence represented by SEQ ID NO: 30 or a fragment thereof,
  (vi) the VH comprises an amino acid sequence represented by SEQ ID NO: 25 or a fragment thereof and the VL comprises an amino acid sequence represented by SEQ ID NO: 29 or a fragment thereof,
  (vii) the VH comprises an amino acid sequence represented by SEQ ID NO: 25 or a fragment thereof and the VL comprises an amino acid sequence represented by SEQ ID NO: 32 or a fragment thereof,
  (viii) the VH comprises an amino acid sequence represented by SEQ ID NO: 25 or a fragment thereof and the VL comprises an amino acid sequence represented by SEQ ID NO: 33 or a fragment thereof,
  (ix) the VH comprises an amino acid sequence represented by SEQ ID NO: 25 or a fragment thereof and the VL comprises an amino acid sequence represented by SEQ ID NO: 34 or a fragment thereof.

In a particularly preferred embodiment, a binding domain for CLDN18.2 comprises the following combination of heavy chain variable region (VH) and light chain variable region (VL):
the VH comprises an amino acid sequence represented by SEQ ID NO: 23 or a fragment thereof and the VL comprises an amino acid sequence represented by SEQ ID NO: 30 or a fragment thereof.

In a further particularly preferred embodiment, a binding domain for CLDN18.2 comprises the following combination of heavy chain variable region (VH) and light chain variable region (VL):
the VH comprises an amino acid sequence represented by SEQ ID NO: 21 or a fragment thereof and the VL comprises an amino acid sequence represented by SEQ ID NO: 26 or a fragment thereof.

In a preferred embodiment, a binding domain for CLDN18.2 comprises (i) a VH comprising a CDR3 comprising the following sequence: TRSWRGNSFDY and/or (ii) a VL comprising a CDR3 comprising the following sequence: QNDYSYPFT.

In a preferred embodiment, a binding domain for CLDN18.2 comprises
(i) a VH comprising the following set of complementarity-determining regions CDR1, CDR2 and CDR3:

```
CDR1:
                                    (SEQ ID NO: 42)
GYTFTSYW,

CDR2:
                                    (SEQ ID NO: 43)
IYPSDSYT,

CDR3:
                                    (SEQ ID NO: 44)
TRSWRGNSFDY
``` and/or
(ii) a VL comprising the following set of complementarity-determining regions CDR1, CDR2 and CDR3:

```
CDR1:
                                    (SEQ ID NO: 45)
QSLLNSGNQKNY,

CDR2:
                                    (SEQ ID NO: 46)
WAS,

CDR3:
                                    (SEQ ID NO: 47)
QNDYSYPFT.
```

In a preferred embodiment, a binding domain for CLDN18.2 comprises a combination of VH and VL each comprising the following set of complementarity-determining regions CDR1, CDR2 and CDR3:

```
VH:
CDR1:
                                    (SEQ ID NO: 42)
GYTFTSYW,

CDR2:
                                    (SEQ ID NO: 43)
IYPSDSYT,

CDR3:
                                    (SEQ ID NO: 44)
TRSWRGNSFDY,

VL:
CDR1:
                                    (SEQ ID NO: 45)
QSLLNSGNQKNY,

CDR2:
                                    (SEQ ID NO: 46)
WAS,

CDR3:
                                    (SEQ ID NO: 47)
QNDYSYPFT.
```

Preferably, a combination of heavy chain variable region (VH) and light chain variable region (VL) described herein is arranged in a single chain Fv (scFv).

The term "fragment" refers, in particular, to one or more of the complementarity-determining regions (CDRs), preferably at least the CDR3 variable region, of the heavy chain variable region (VH) and/or of the light chain variable region (VL). In one embodiment said one or more of the complementarity-determining regions (CDRs) are selected from a set of complementarity-determining regions CDR1, CDR2 and CDR3. In a particularly preferred embodiment, the term "fragment" refers to the complementarity-determining regions CDR1, CDR2 and CDR3 of the heavy chain variable region (VH) and/or of the light chain variable region (VL).

In one embodiment a binding domain for CLDN18.2 comprising one or more CDRs, a set of CDRs or a combination of sets of CDRs as described herein comprises said CDRs together with their intervening framework regions. Preferably, the portion will also include at least about 50% of either or both of the first and fourth framework regions, the 50% being the C-terminal 50% of the first framework region and the N-terminal 50% of the fourth framework region. Construction of binding agents made by recombinant DNA techniques may result in the introduction of residues N- or C-terminal to the variable regions encoded by linkers introduced to facilitate cloning or other manipulation steps, including the introduction of linkers to join variable regions of the invention to further protein sequences including immunoglobulin heavy chains, other variable domains (for example in the production of diabodies) or protein labels.

In one embodiment a binding domain for CLDN18.2 comprising one or more CDRs, a set of CDRs or a combination of sets of CDRs as described herein comprises said CDRs in a human antibody framework.

In one embodiment, a binding domain for CLDN18.2 according to the invention relates to a binding domain for CLDN18.2 which recognizes, i.e. binds to, the same or essentially the same epitope as a binding domain for CLDN18.2 described herein (such as an antibody comprising a combination of heavy chain variable region (VH) and light chain variable region (VL) described herein), and/or competes with said binding domain for CLDN18.2 for binding to CLDN18.2.

The term "binding" according to the invention preferably relates to a specific binding.

According to the present invention, an agent such as a T cell receptor or an antibody is capable of binding to a predetermined target if it has a significant affinity for said predetermined target and binds to said predetermined target in standard assays. "Affinity" or "binding affinity" is often measured by equilibrium dissociation constant ($K_D$). Preferably, the term "significant affinity" refers to the binding to a predetermined target with a dissociation constant ($K_D$) of $10^{-5}$ M or lower, $10^{-6}$ M or lower, $10^{-7}$ M or lower, $10^{-8}$ M or lower, $10^{-9}$ M or lower, $10^{-10}$ M or lower, $10^{-11}$ M or lower, or $10^{-12}$ M or lower.

An agent is not (substantially) capable of binding to a target if it has no significant affinity for said target and does not bind significantly, in particular does not bind detectably, to said target in standard assays. Preferably, the agent does not detectably bind to said target if present in a concentration of up to 2, preferably 10, more preferably 20, in particular 50 or 100 µg/ml or higher. Preferably, an agent has no significant affinity for a target if it binds to said target with a $K_D$ that is at least 10-fold, 100-fold, $10^3$-fold, $10^4$-fold, $10^5$-fold, or $10^6$-fold higher than the $K_D$ for binding to the predetermined target to which the agent is capable of binding. For example, if the $K_D$ for binding of an agent to the target to which the agent is capable of binding is $10^{-7}$ M, the $K_D$ for binding to a target for which the agent has no significant affinity would be at least $10^{-6}$ M, $10^{-5}$ M, $10^{-4}$ M, $10^{-3}$ M, $10^{-2}$ M, or $10^{-1}$ M.

An agent is specific for a predetermined target if it is capable of binding to said predetermined target while it is not (substantially) capable of binding to other targets, i.e. has no significant affinity for other targets and does not significantly bind to other targets in standard assays. According to the invention, an agent is specific for CLDN18.2 if it is capable of binding to CLDN18.2 but is not (substantially) capable of binding to other targets. Preferably, an agent is specific for CLDN18.2 if the affinity for and the binding to such other targets does not significantly exceed the affinity for or binding to CLDN18.2-unrelated proteins such as bovine serum albumin (BSA), casein, human serum albumin (HSA) or non-claudin transmembrane proteins such as MHC molecules or transferrin receptor or any other specified polypeptide. Preferably, an agent is specific for a predetermined target if it binds to said target with a $K_D$ that is at least 10-fold, 100-fold, $10^3$-fold, $10^4$-fold, $10^5$-fold, or $10^6$-fold lower than the $K_D$ for binding to a target for which it is not specific. For example, if the $K_D$ for binding of an agent to the target for which it is specific is $10^{-7}$ M, the $K_D$ for binding to a target for which it is not specific would be at least $10^{-6}$ M, $10^{-5}$ M, $10^{-4}$ M, $10^{-3}$ M, $10^{-2}$ M, or $10^{-1}$ M.

Binding of an agent to a target can be determined experimentally using any suitable method; see, for example, Berzofsky et al., "Antibody-Antigen Interactions" In Fundamental Immunology, Paul, W. E., Ed., Raven Press New York, N Y (1984), Kuby, Janis Immunology, W. H. Freeman and Company New York, N Y (1992), and methods described herein. Affinities may be readily determined using conventional techniques, such as by equilibrium dialysis; by using the BIAcore 2000 instrument, using general procedures outlined by the manufacturer; by radioimmunoassay using radiolabeled target antigen; or by another method known to the skilled artisan. The affinity data may be analyzed, for example, by the method of Scatchard et al., Ann N.Y. Acad. ScL, 51:660 (1949). The measured affinity of a particular antibody-antigen interaction can vary if measured under different conditions, e.g., salt concentration, pH. Thus, measurements of affinity and other antigen-binding parameters, e.g., $K_D$, $IC_{50}$, are preferably made with standardized solutions of antibody and antigen, and a standardized buffer.

It is to be understood that the peptide and protein agents described herein may be provided in vitro or in vivo in the form of a nucleic acid such as RNA encoding the agent and/or in the form of a host cell comprising a nucleic acid such as RNA encoding the agent. In particular, a variety of methods may be used to introduce CAR constructs into T cells including non-viral-based DNA transfection, transposon-based systems and viral-based systems. Non-viral-based DNA transfection has low risk of insertional mutagenesis. Transposon-based systems can integrate transgenes more efficiently than plasmids that do not contain an integrating element. Viral-based systems include the use of γ-retroviruses and lentiviral vectors. γ-Retroviruses are relatively easy to produce, efficiently and permanently transduce T cells, and have preliminarily proven safe from an integration standpoint in primary human T cells. Lentiviral vectors also efficiently and permanently transduce T cells but are more expensive to manufacture. They are also potentially safer than retrovirus based systems.

The peptide and protein agents described herein may be delivered to a patient by administering a nucleic acid such as RNA encoding the agent and/or by administering a host cell comprising a nucleic acid such as RNA encoding the agent. A nucleic acid when administered to a patient may be present in naked form or in a suitable delivery vehicle such as in the form of liposomes or viral particles, or within a host cell. The nucleic acid provided can produce the agent over extended time periods in a sustained manner mitigating the instability at least partially observed for therapeutic proteins. If a nucleic acid is administered to a patient without being present within a host cell, it is preferably taken up by cells of the patient for expression of the agent encoded by the nucleic acid. If a nucleic acid is administered to a patient while being present within a host cell, it is preferably expressed by the host cell within the patient so as to produce the agent encoded by the nucleic acid.

The term "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the invention, a nucleic acid is preferably an isolated nucleic acid.

Nucleic acids may be comprised in a vector. The term "vector" as used herein includes any vectors known to the skilled person including plasmid vectors, cosmid vectors, phage vectors such as lambda phage, viral vectors such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In the context of the present invention, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term includes double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

According to the present invention, the term "RNA" includes and preferably relates to "mRNA" which means "messenger RNA" and relates to a "transcript" which may be produced using DNA as template and encodes a peptide or protein. mRNA typically comprises a 5' non translated region (5'-UTR), a protein or peptide coding region and a 3' non translated region (3'-UTR). mRNA has a limited half-time in cells and in vitro. Preferably, mRNA is produced by in vitro transcription using a DNA template. In one embodiment of the invention, the RNA is obtained by in vitro transcription or chemical synthesis. The in vitro transcription methodology is known to the skilled person. For example, there is a variety of in vitro transcription kits commercially available.

In one embodiment of the present invention, RNA is self-replicating RNA, such as single stranded self-replicating RNA. In one embodiment, the self-replicating RNA is single stranded RNA of positive sense. In one embodiment, the self-replicating RNA is viral RNA or RNA derived from viral RNA. In one embodiment, the self-replicating RNA is alphaviral genomic RNA or is derived from alphaviral genomic RNA. In one embodiment, the self-replicating RNA is a viral gene expression vector. In one embodiment, the virus is Semliki forest virus. In one embodiment, the self-replicating RNA contains one or more transgenes at least one of said transgenes encoding the agents described herein. In one embodiment, if the RNA is viral RNA or derived from viral RNA, the transgenes may partially or completely replace viral sequences such as viral sequences encoding structural proteins. In one embodiment, the self-replicating RNA is in vitro transcribed RNA.

In order to increase expression and/or stability of the RNA used according to the present invention, it may be modified, preferably without altering the sequence of the expressed peptide or protein.

The term "modification" in the context of RNA as used according to the present invention includes any modification of RNA which is not naturally present in said RNA.

In one embodiment of the invention, the RNA used according to the invention does not have uncapped 5'-triphosphates. Removal of such uncapped 5'-triphosphates can be achieved by treating RNA with a phosphatase.

The RNA according to the invention may have modified naturally occurring or synthetic ribonucleotides in order to increase its stability and/or decrease cytotoxicity. For example, in one embodiment, in the RNA used according to the invention 5-methylcytidine is substituted partially or completely, preferably completely, for cytidine. Alternatively or additionally, in one embodiment, in the RNA used according to the invention pseudouridine is substituted partially or completely, preferably completely, for uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage. In one embodiment, this guanosine is methylated at the 7-position. The term "conventional 5'-cap" refers to a naturally occurring RNA 5'-cap, preferably to the 7-methylguanosine cap (m7G). In the context of the present invention, the term "5'-cap" includes a 5'-cap analog that resembles the RNA cap structure and is modified to possess the ability to stabilize RNA if attached thereto, preferably in vivo and/or in a cell.

Providing an RNA with a 5'-cap or 5'-cap analog may be achieved by in vitro transcription of a DNA template in the presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

The RNA may comprise further modifications. For example, a further modification of the RNA used in the present invention may be an extension or truncation of the naturally occurring poly(A) tail or an alteration of the 5'- or 3'-untranslated regions (UTR) such as introduction of a UTR which is not related to the coding region of said RNA, for example, the insertion of one or more, preferably two copies of a 3'-UTR derived from a globin gene, such as alpha2-globin, alpha1-globin, beta-globin, preferably beta-globin, more preferably human beta-globin.

Therefore, in order to increase stability and/or expression of the RNA used according to the present invention, it may be modified so as to be present in conjunction with a poly-A sequence, preferably having a length of 10 to 500, more preferably 30 to 300, even more preferably 65 to 200 and especially 100 to 150 adenosine residues. In an especially preferred embodiment the poly-A sequence has a length of approximately 120 adenosine residues. In addition, incorporation of two or more 3'-non translated regions (UTR) into the 3'-non translated region of an RNA molecule can result in an enhancement in translation efficiency. In one particular embodiment the 3'-UTR is derived from the human β-globin gene.

The term "stability" of RNA relates to the "half-life" of RNA. "Half-life" relates to the period of time which is needed to eliminate half of the activity, amount, or number of molecules. In the context of the present invention, the half-life of an RNA is indicative for the stability of said RNA. The half-life of RNA may influence the "duration of expression" of the RNA. It can be expected that RNA having a long half-life will be expressed for an extended time period.

In the context of the present invention, the term "transcription" relates to a process, wherein the genetic code in a DNA sequence is transcribed into RNA. Subsequently, the RNA may be translated into protein. According to the present invention, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present invention encompassed by the term "vector".

The term "translation" according to the invention relates to the process in the ribosomes of a cell by which a strand of messenger RNA directs the assembly of a sequence of amino acids to make a peptide or protein.

Nucleic acids may, according to the invention, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that the nucleic acids are also functionally linked naturally and the term "heterologous" means that the nucleic acids are not functionally linked naturally.

A nucleic acid and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" or "expression control element" comprises according to the invention promoters, ribosome binding sites, enhancers and other control elements which regulate transcription of a gene or translation of a mRNA. In particular embodiments of the invention, the expression control sequences can be regulated. The exact structure of expression control sequences may vary as a function of the species or cell type, but generally comprises 5'-untranscribed and 5'- and 3'-untranslated sequences which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences.

The term "expression" is used according to the invention in its most general meaning and comprises the production of RNA and/or peptides or proteins, e.g. by transcription and/or translation. With respect to RNA, the term "expression" or "translation" relates in particular to the production of peptides or proteins. It also comprises partial expression of nucleic acids. Moreover, expression can be transient or stable. According to the invention, the term expression also includes an "aberrant expression" or "abnormal expression".

"Aberrant expression" or "abnormal expression" means according to the invention that expression is altered, preferably increased, compared to a reference, e.g. a state in a subject not having a disease associated with aberrant or abnormal expression of a certain protein, e.g., a tumor antigen. An increase in expression refers to an increase by at least 10%, in particular at least 20%, at least 50% or at least 100%, or more. In one embodiment, expression is only found in a diseased tissue, while expression in a healthy tissue is repressed.

The term "specifically expressed" means that a protein is essentially only expressed in a specific tissue or organ. For example, a tumor antigen specifically expressed in gastric mucosa means that said protein is primarily expressed in gastric mucosa and is not expressed in other tissues or is not expressed to a significant extent in other tissue or organ types. Thus, a protein that is exclusively expressed in cells of the gastric mucosa and to a significantly lesser extent in any other tissue, such as testis, is specifically expressed in cells of the gastric mucosa. In some embodiments, a tumor antigen may also be specifically expressed under normal conditions in more than one tissue type or organ, such as in 2 or 3 tissue types or organs, but preferably in not more than 3 different tissue or organ types. In this case, the tumor antigen is then specifically expressed in these organs. For example, if a tumor antigen is expressed under normal conditions preferably to an approximately equal extent in lung and stomach, said tumor antigen is specifically expressed in lung and stomach.

According to the invention, the term "nucleic acid encoding" means that nucleic acid, if present in the appropriate environment, preferably within a cell, can be expressed to produce a protein or peptide it encodes.

Some aspects of the invention rely on the adoptive transfer of host cells which are transfected in vitro with a nucleic acid such as RNA encoding an agent described herein and transferred to recipients such as patients, preferably after ex vivo expansion from low precursor frequencies to clinically relevant cell numbers. The host cells used for treatment according to the invention may be autologous, allogeneic, or syngeneic to a treated recipient.

The term "autologous" is used to describe anything that is derived from the same subject. For example, "autologous transplant" refers to a transplant of tissue or organs derived from the same subject. Such procedures are advantageous because they overcome the immunological barrier which otherwise results in rejection.

The term "allogeneic" is used to describe anything that is derived from different individuals of the same species. Two or more individuals are said to be allogeneic to one another when the genes at one or more loci are not identical.

The term "syngeneic" is used to describe anything that is derived from individuals or tissues having identical genotypes, i.e., identical twins or animals of the same inbred strain, or their tissues.

The term "heterologous" is used to describe something consisting of multiple different elements. As an example, the transfer of one individual's bone marrow into a different individual constitutes a heterologous transplant. A heterologous gene is a gene derived from a source other than the subject.

The term "transfection" relates to the introduction of nucleic acids, in particular RNA, into a cell. For purposes of the present invention, the term "transfection" also includes the introduction of a nucleic acid into a cell or the uptake of a nucleic acid by such cell, wherein the cell may be present in a subject, e.g., a patient. Thus, according to the present invention, a cell for transfection of a nucleic acid described herein can be present in vitro or in vivo, e.g. the cell can form part of an organ, a tissue and/or an organism of a patient. According to the invention, transfection can be transient or stable. For some applications of transfection, it is sufficient if the transfected genetic material is only transiently expressed. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. RNA can be transfected into cells to transiently express its coded protein.

According to the present invention, any technique useful for introducing, i.e. transferring or transfecting, nucleic acids into cells may be used. Preferably, RNA is transfected into cells by standard techniques. Such techniques include electroporation, lipofection and microinjection. In one particularly preferred embodiment of the present invention, RNA is introduced into cells by electroporation.

Electroporation or electropermeabilization relates to a significant increase in the electrical conductivity and permeability of the cell plasma membrane caused by an externally applied electrical field. It is usually used in molecular biology as a way of introducing some substance into a cell.

According to the invention it is preferred that introduction of nucleic acid encoding a protein or peptide into cells results in expression of said protein or peptide.

The term "peptide" according to the invention comprises oligo- and polypeptides and refers to substances comprising two or more, preferably 3 or more, preferably 4 or more, preferably 6 or more, preferably 8 or more, preferably 9 or more, preferably 10 or more, preferably 13 or more, preferably 16 more, preferably 21 or more and up to preferably 8, 10, 20, 30, 40 or 50, in particular 100 amino acids joined covalently by peptide bonds. The term "protein" refers to large peptides, preferably to peptides with more than 100 amino acid residues, but in general the terms "peptides" and "proteins" are synonyms and are used interchangeably herein.

According to the invention, a peptide may include natural amino acids and non-natural amino acids. In one embodiment, a peptide merely includes natural amino acids.

According to the invention, the term "non-natural amino acid" refers to an amino acid having a structure different from those of the 20 natural amino acid species. Since non-natural amino acids have structures similar to those of natural amino acids, non-natural amino acids may be classified as derivatives or analogs of given natural amino acids.

Preferably, the proteins and peptides described according to the invention have been isolated. The terms "isolated protein" or "isolated peptide" mean that the protein or peptide has been separated from its natural environment. An isolated protein or peptide may be in an essentially purified state. The term "essentially purified" means that the protein or peptide is essentially free of other substances with which it is associated in nature or in vivo.

The teaching given herein with respect to specific amino acid sequences, e.g. those shown in the sequence listing, is to be construed so as to also relate to variants of said specific sequences resulting in sequences which are functionally equivalent to said specific sequences, e.g. amino acid sequences exhibiting properties identical or similar to those of the specific amino acid sequences. One important property is to retain binding of a peptide to an MHC molecule and/or to a T cell receptor or of a T cell receptor to its target or to sustain effector functions of a T cell. Preferably, a sequence modified with respect to a specific sequence, when it replaces the specific sequence in a T cell receptor retains binding of said T cell receptor to the target and preferably functions of said T cell receptor or T cell carrying the T cell receptor as described herein.

For example, the sequences shown in the sequence listing can be modified so as to remove one or more, preferably all free cysteine residues, in particular by replacing the cysteine residues by amino acids other than cysteine, preferably serine, alanine, threonine, glycine, tyrosine, leucine or methionine, most preferably alanine or serine.

It will be appreciated by those skilled in the art that in particular the sequences of the CDR sequences, hypervariable and variable regions can be modified without losing the ability to bind to a target. For example, CDR regions will be either identical or highly homologous to the regions of antibodies specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions specifically disclosed herein.

A peptide "variant" may retain the immunogenicity of a given peptide (e.g. the ability of the variant to react with T cell lines or clones is not substantially diminished relative to the given peptide). In other words, the ability of a variant to react with T cell lines or clones may be enhanced or unchanged, relative to the given peptide, or may be diminished by less than 50%, and preferably less than 20%, relative to the given peptide.

A variant may be identified by evaluating its ability to bind to a MHC molecule. In one preferred embodiment, a variant peptide has a modification such that the ability of the variant peptide to bind to a MHC molecule is increased relative to the given peptide. The ability of the variant peptide to bind to a MHC molecule may be increased by at least 2-fold, preferably at least 3-fold, 4-fold, or 5-fold relative to that of a given peptide. Accordingly, within certain preferred embodiments, a peptide comprises a variant in which 1 to 3 amino acid resides within an immunogenic portion are substituted such that the ability to react with T cell lines or clones is statistically greater than that for the unmodified peptide. Such substitutions are preferably located within an MHC binding site of the peptide. Preferred substitutions allow increased binding to MHC class I or class II molecules. Certain variants contain conservative substitutions.

The term "variant" according to the invention also includes mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

For the purposes of the present invention, "variants" of an amino acid sequence comprise amino acid insertion variants, amino acid addition variants, amino acid deletion variants and/or amino acid substitution variants. Amino acid deletion variants that comprise the deletion at the N-terminal and/or C-terminal end of the protein are also called N-terminal and/or C-terminal truncation variants.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein.

Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

Homologous amino acid sequences exhibit according to the invention at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing proteins and peptides having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

The invention includes derivatives of the peptides or proteins described herein which are comprised by the terms "peptide" and "protein". According to the invention, "derivatives" of proteins and peptides are modified forms of proteins and peptides. Such modifications include any chemical modification and comprise single or multiple substitutions, deletions and/or additions of any molecules associated with the protein or peptide, such as carbohydrates, lipids and/or proteins or peptides. In one embodiment, "derivatives" of proteins or peptides include those modified analogs resulting from glycosylation, acetylation, phosphorylation, amidation, palmitoylation, myristoylation, isoprenylation, lipidation, alkylation, derivatization, introduction of protective/blocking groups, proteolytic cleavage or binding to an antibody or to another cellular ligand. The term "derivative" also extends to all functional chemical equivalents of said proteins and peptides. Preferably, a modified peptide has increased stability and/or increased immunogenicity.

Also included are mimetics of peptides. Such mimetics may comprise amino acids linked to one or more amino acid mimetics (i.e., one or more amino acids within the peptide may be replaced by an amino acid mimetic) or may be entirely nonpeptide mimetics. An amino acid mimetic is a compound that is conformationally similar to an amino acid, e.g. such that it can be substituted for an amino acid without substantially diminishing the ability to react with T cell lines or clones. A nonpeptide mimetic is a compound that does not contain amino acids, and that has an overall conformation that is similar to a peptide, e.g. such that the ability of the mimetic to react with T cell lines or clones is not substantially diminished relative to the ability of a given peptide.

According to the invention, a variant, derivative, modified form, fragment, part or portion of an amino acid sequence, peptide or protein preferably has a functional property of the amino acid sequence, peptide or protein, respectively, from which it has been derived, i.e. it is functionally equivalent. In one embodiment, a variant, derivative, modified form, fragment, part or portion of an amino acid sequence, peptide or protein is immunologically equivalent to the amino acid sequence, peptide or protein, respectively, from which it has been derived. In one embodiment, the functional property is an immunological property.

A particular property is the ability to form a complex with MHC molecules and, where appropriate, generate an immune response, preferably by stimulating cytotoxic or T helper cells.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect such as induction of a humoral and/or cellular immune response, the strength and/or duration of the induced immune reaction, or the specificity of the induced immune reaction. In the context of the present invention, the term "immunologically equivalent" is preferably used with respect to the immunological effects or properties of a peptide or peptide variant used for immunization. For example, an amino acid sequence is immunologically equivalent to a reference amino acid sequence if said amino acid sequence when exposed to the immune system of a subject induces an immune reaction having a specificity of reacting with the reference amino acid sequence.

The term "derived" means according to the invention that a particular entity, in particular a particular sequence, is present in the object from which it is derived, in particular an organism or molecule. In the case of amino acid sequences, especially particular sequence regions, "derived" in particular means that the relevant amino acid sequence is derived from an amino acid sequence in which it is present.

The term "cell" or "host cell" preferably relates to an intact cell, i.e. a cell with an intact membrane that has not released its normal intracellular components such as enzymes, organelles, or genetic material. An intact cell preferably is a viable cell, i.e. a living cell capable of carrying out its normal metabolic functions. Preferably said term relates according to the invention to any cell which can be transfected with an exogenous nucleic acid. Preferably, the cell when transfected with an exogenous nucleic acid and transferred to a recipient can express the nucleic acid in the recipient. The term "cell" includes bacterial cells; other useful cells are yeast cells, fungal cells or mammalian cells. Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*. Suitable yeast cells include cells from species of *Saccharomyces* (Tor example *Saccharomyces cerevisiae*), *Schizosaccharomyces* (for example Schizo *Saccharomyces pombe*), *Pichia* (for example *Pichia pastoris* and *Pichia* methanolicd), and *Hansenula*. Suitable mammalian cells include for example CHO cells, BHK cells, HeLa cells, COS cells, 293 HEK and the like. However, amphibian cells, insect cells, plant cells, and any other cells used in the art for the expression of heterologous proteins can be used as well. Mammalian cells are particularly preferred for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR).

A cell which comprises a nucleic acid molecule preferably express the peptide or protein encoded by the nucleic acid.

The cell may be a recombinant cell and may secrete the encoded peptide or protein, may express it on the surface and preferably may additionally express an MHC molecule which binds to said peptide or protein or a procession product thereof. In one embodiment, the cell expresses the MHC molecule endogenously. In a further embodiment, the cell expresses the MHC molecule and/or the peptide or protein or the procession product thereof in a recombinant manner. The cell is preferably nonproliferative. In a preferred embodiment, the cell is an antigen-presenting cell, in particular a dendritic cell, a monocyte or a macrophage.

The term "clonal expansion" refers to a process wherein a specific entity is multiplied. In the context of the present invention, the term is preferably used in the context of an immunological response in which lymphocytes are stimulated by an antigen, proliferate, and the specific lymphocyte recognizing said antigen is amplified. Preferably, clonal expansion leads to differentiation of the lymphocytes.

A disease associated with antigen expression may be detected based on the presence of T cells that specifically react with a peptide in a biological sample. Within certain methods, a biological sample comprising CD4+ and/or CD8+ T cells isolated from a patient is incubated with a peptide of the invention, a nucleic acid encoding such peptide and/or an antigen-presenting cell that expresses and/or presents at least an immunogenic portion of such a peptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). For CD4+ T cells, activation is preferably detected by evaluating proliferation of the T cells. For CD8+ T cells, activation is preferably detected by evaluating cytolytic activity. A level of proliferation that is at least two fold greater and/or a level of cytolytic activity that is at least 20% greater than in disease-free subjects indicates the presence of a disease associated with antigen expression in the subject.

"Reduce" or "inhibit" as used herein means the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increase" or "enhance" preferably relate to an increase or enhancement by about at least 10%, preferably at least 20%, preferably at least 30%, more preferably at least 40%, more preferably at least 50%, even more preferably at least 80%, and most preferably at least 100%.

The agents, compositions and methods described herein can be used to treat a subject with a disease, e.g., a disease characterized by the presence of diseased cells expressing CLDN18.2 and preferably presenting CLDN18.2 in the context of MHC molecules. Examples of diseases which can be treated and/or prevented encompass all diseases expressing CLDN18.2. Particularly preferred diseases are cancer diseases.

The agents, compositions and methods described herein may also be used for immunization or vaccination to prevent a disease described herein.

The terms "normal tissue" or "normal conditions" refer to healthy tissue or the conditions in a healthy subject, i.e., non-pathological conditions, wherein "healthy" preferably means non-cancerous.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality. According to the invention, the term "disease" includes cancer, in particular those forms of cancer described herein. Any reference herein to cancer or particular forms of cancer also includes cancer metastasis thereof. In a preferred embodiment, a disease to be treated according to the present application involves cells expressing CLDN18.2 and optionally presenting CLDN18.2 in the context of MHC molecules.

"Diseases involving cells expressing CLDN18.2" or similar expressions means according to the invention that CLDN18.2 is expressed in cells of a diseased tissue or organ. In one embodiment, expression of CLDN18.2 in cells of a diseased tissue or organ is increased compared to the state in a healthy tissue or organ. An increase refers to an increase by at least 10%, in particular at least 20%, at least 50%, at least 100%, at least 200%, at least 500%, at least 1000%, at least 10000% or even more. In one embodiment, expression is only found in a diseased tissue, while expression in a healthy tissue is repressed. According to the invention, diseases involving cells expressing CLDN18.2 include cancer diseases. Furthermore, according to the invention, cancer diseases preferably are those wherein the cancer cells express CLDN18.2.

The terms "cancer disease" or "cancer" refer to or describe the physiological condition in an individual that is typically characterized by unregulated cell growth. Examples of cancers include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. The term "cancer" according to the invention also comprises cancer metastases. Preferably, a "cancer disease" is characterized by cells expressing CLDN18.2 and a cancer cell expresses CLDN18.2.

A diseased cell preferably is a cell expressing CLDN18.2 said CLDN18.2 preferably being present on the surface of said cell as transmembrane protein and/or being presented by said cell in the context of MHC such as MHC I. A cell expressing CLDN18.2 preferably is a cancer cell, preferably of the cancers described herein.

In one embodiment, a cancer disease is a malignant disease which is characterized by the properties of anaplasia, invasiveness, and metastasis. A malignant tumor may be contrasted with a non-cancerous benign tumor in that a malignancy is not self-limited in its growth, is capable of invading into adjacent tissues, and may be capable of spreading to distant tissues (metastasizing), while a benign tumor has none of those properties.

In one embodiment, a cancer according to the invention involves cancer cells expressing CLDN18.2. In one embodiment, the cancer is CLDN18.2 positive. In one embodiment, expression of CLDN18.2 is at the surface of the cells. In one embodiment, at least 50%, preferably 60%, 70%, 80% or 90% of the cancer cells are CLDN18.2 positive and/or at least 40%, preferably at least 50% of the cancer cells are positive for surface expression of CLDN18.2. In one embodiment, at least 95% or at least 98% of the cancer cells are CLDN18.2 positive. In one embodiment, at least 60%, at least 70%, at least 80% or at least 90% of the cancer cells are positive for surface expression of CLDN18.2.

In one embodiment, a CLDN18.2-expressing cancer, a cancer involving cancer cells expressing CLDN18.2 or a CLDN18.2 positive cancer is selected from the group consisting of gastric cancer, esophageal cancer, pancreatic cancer, lung cancer such as non small cell lung cancer (NSCLC), ovarian cancer, colon cancer, hepatic cancer, head-neck cancer, and cancer of the gallbladder and metastases thereof, in particular gastric cancer metastasis such as Krukenberg tumors, peritoneal metastasis and lymph node metastasis. In one embodiment, the cancer is an adenocarcinoma, in particular an advanced adenocarcinoma. Particularly preferred cancer diseases are adenocarcinomas of the stomach, the esophagus, the pancreatic duct, the bile ducts, the lung and the ovary. In one embodiment, the cancer is selected from the group consisting of cancer of the stomach, cancer of the esophagus, in particular the lower esophagus, cancer of the eso-gastric junction and gastroesophageal cancer. In a particularly preferred embodiment, the cancer is gastroesophageal cancer such as metastatic, refractory or recurrent advanced gastroesophageal cancer.

According to the invention, the term "tumor" or "tumor disease" refers to a swelling or lesion formed by an abnormal growth of cells (called neoplastic cells or tumor cells). By "tumor cell" is meant an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign, pre-malignant or malignant.

According to the invention, a "carcinoma" is a malignant tumor derived from epithelial cells. This group represents the most common cancers, including the common forms of breast, prostate, lung and colon cancer.

"Adenocarcinoma" is a cancer that originates in glandular tissue. This tissue is also part of a larger tissue category known as epithelial tissue. Epithelial tissue includes skin, glands and a variety of other tissue that lines the cavities and organs of the body. Epithelium is derived embryologically from ectoderm, endoderm and mesoderm. To be classified as adenocarcinoma, the cells do not necessarily need to be part of a gland, as long as they have secretory properties. This form of carcinoma can occur in some higher mammals, including humans. Well differentiated adenocarcinomas tend to resemble the glandular tissue that they are derived from, while poorly differentiated may not. By staining the cells from a biopsy, a pathologist will determine whether the tumor is an adenocarcinoma or some other type of cancer. Adenocarcinomas can arise in many tissues of the body due to the ubiquitous nature of glands within the body. While each gland may not be secreting the same substance, as long as there is an exocrine function to the cell, it is considered glandular and its malignant form is therefore named adenocarcinoma. Malignant adenocarcinomas invade other tissues and often metastasize given enough time to do so. Ovarian adenocarcinoma is the most common type of ovarian carcinoma. It includes the serous and mucinous adenocarcinomas, the clear cell adenocarcinoma and the endometrioid adenocarcinoma.

Lymphoma and leukemia are malignancies derived from hematopoietic (blood-forming) cells.

Blastic tumor or blastoma is a tumor (usually malignant) which resembles an immature or embryonic tissue. Many of these tumors are most common in children.

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" according to the invention relates to "distant metastasis" which relates to a metastasis which is remote from the primary tumor and the regional lymph node system. In one embodiment, the term "metastasis" according to the invention relates to lymph node metastasis.

The cells of a secondary or metastatic tumor are like those in the original tumor. This means, for example, that, if ovarian cancer metastasizes to the liver, the secondary tumor is made up of abnormal ovarian cells, not of abnormal liver cells. The tumor in the liver is then called metastatic ovarian cancer, not liver cancer.

A relapse or recurrence occurs when a person is affected again by a condition that affected them in the past. For example, if a patient has suffered from a tumor disease, has received a successful treatment of said disease and again develops said disease said newly developed disease may be considered as relapse or recurrence. However, according to the invention, a relapse or recurrence of a tumor disease may but does not necessarily occur at the site of the original tumor disease. Thus, for example, if a patient has suffered from ovarian tumor and has received a successful treatment a relapse or recurrence may be the occurrence of an ovarian tumor or the occurrence of a tumor at a site different to ovary. A relapse or recurrence of a tumor also includes situations wherein a tumor occurs at a site different to the site of the original tumor as well as at the site of the original tumor. Preferably, the original tumor for which the patient has received a treatment is a primary tumor and the tumor at a site different to the site of the original tumor is a secondary or metastatic tumor.

The term "treatment" or "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to human beings, non-human primates or other mammals (e.g. mouse, rat, rabbit, dog, cat, cattle, swine, sheep, horse or primate) that can be afflicted with or are susceptible to a disease or disorder (e.g., cancer) but may or may not have the disease or disorder. In many embodiments, the individual is a human being. Unless otherwise stated, the terms "individual" and "subject" do not denote a particular age, and thus encompass adults, elderlies, children, and newborns. In preferred embodiments of the present invention, the "individual" or "subject" is a "patient". The term "patient" means according to the invention a subject for treatment, in particular a diseased subject.

By "being at risk" is meant a subject, i.e. a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

The term "immunotherapy" relates to a treatment involving a specific immune reaction.

In the context of the present invention, terms such as "protect", "prevent", "prophylactic", "preventive", or "protective" relate to the prevention or treatment or both of the occurrence and/or the propagation of a disease in a subject and, in particular, to minimizing the chance that a subject will develop a disease or to delaying the development of a disease. For example, a person at risk for a tumor, as described above, would be a candidate for therapy to prevent a tumor.

A prophylactic administration of an immunotherapy, for example, a prophylactic administration of an agent or composition of the invention, preferably protects the recipient from the development of a disease. A therapeutic administration of an immunotherapy, for example, a therapeutic administration of an agent or composition of the invention, may lead to the inhibition of the progress/growth of the disease. This comprises the deceleration of the progress/growth of the disease, in particular a disruption of the progression of the disease, which preferably leads to elimination of the disease.

Immunotherapy may be performed using any of a variety of techniques, in which agents provided herein preferably function to remove CLDN18.2-expressing cells from a patient. Such removal may take place as a result of enhancing or inducing an immune response in a patient specific for CLDN18.2 or a cell expressing CLDN18.2 and/or presenting CLDN18.2 in the context of MHC molecules.

Within certain embodiments, immunotherapy may be active immunotherapy, in which treatment relies on the in vivo stimulation of the endogenous host immune system to react against diseased cells with the administration of immune response-modifying agents (such as peptides and nucleic acids as provided herein).

Within other embodiments, immunotherapy may be passive immunotherapy, in which treatment involves the delivery of agents with established tumor-immune reactivity (such as effector cells) that can directly or indirectly mediate antitumor effects and does not necessarily depend on an intact host immune system. Examples of effector cells include T lymphocytes (such as CD8+ cytotoxic T lymphocytes and CD4+ T-helper lymphocytes), and antigen-presenting cells (such as dendritic cells and macrophages). T cell receptors specific for the CLDN18.2 peptides recited herein and artificial T cell receptors specific for CLDN18.2 may be transferred into effector cells for adoptive immunotherapy.

As noted above, immunoreactive peptides as provided herein may be used to rapidly expand antigen-specific T cell cultures in order to generate a sufficient number of cells for immunotherapy. In particular, antigen-presenting cells, such as dendritic cells, macrophages, monocytes, fibroblasts and/or B cells, may be pulsed with immunoreactive peptides or transfected with one or more nucleic acids using standard techniques well known in the art. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al. (1997), Immunological Reviews 157, 177.

Alternatively, a nucleic acid expressing a peptide recited herein may be introduced into antigen-presenting cells taken from a patient and clonally propagated ex vivo for transplant back into the same patient.

Transfected cells may be reintroduced into the patient using any means known in the art, preferably in sterile form by intravenous, intracavitary, intraperitoneal or intratumor administration.

Methods disclosed herein may involve the administration of autologous T cells that have been activated in response to a peptide or peptide-expressing antigen presenting cell. Such T cells may be CD4+ and/or CD8+, and may be proliferated as described above. The T cells may be administered to the subject in an amount effective to inhibit the development of a disease.

The term "immunization" or "vaccination" describes the process of treating a subject with the purpose of inducing an immune response for therapeutic or prophylactic reasons.

The term "in vivo" relates to the situation in a subject.

According to the invention, a "sample" may be any sample useful according to the present invention, in particular a biological sample such a tissue sample, including body fluids, and/or a cellular sample and may be obtained in the conventional manner such as by tissue biopsy, including punch biopsy, and by taking blood, bronchial aspirate, sputum, urine, feces or other body fluids. According to the invention, the term "sample" also includes processed samples such as fractions or isolates of biological samples, e.g. nucleic acid and peptide/protein isolates.

The compounds and agents described herein may be administered in the form of any suitable pharmaceutical composition.

The pharmaceutical compositions of the invention are preferably sterile and contain an effective amount of the agents described herein and optionally of further agents as discussed herein to generate the desired reaction or the desired effect.

Pharmaceutical compositions are usually provided in a uniform dosage form and may be prepared in a manner known per se. A pharmaceutical composition may e.g. be in the form of a solution or suspension.

A pharmaceutical composition may comprise salts, buffer substances, preservatives, carriers, diluents and/or excipients all of which are preferably pharmaceutically acceptable. The term "pharmaceutically acceptable" refers to the non-toxicity of a material which does not interact with the action of the active component of the pharmaceutical composition.

Salts which are not pharmaceutically acceptable may be used for preparing pharmaceutically acceptable salts and are included in the invention. Pharmaceutically acceptable salts of this kind comprise in a non limiting way those prepared from the following acids: hydrochloric, hydrobromic, sulfuric, nitric, phosphoric, maleic, acetic, salicylic, citric, formic, malonic, succinic acids, and the like. Pharmaceutically acceptable salts may also be prepared as alkali metal salts or alkaline earth metal salts, such as sodium salts, potassium salts or calcium salts.

Suitable buffer substances for use in a pharmaceutical composition include acetic acid in a salt, citric acid in a salt, boric acid in a salt and phosphoric acid in a salt.

Suitable preservatives for use in a pharmaceutical composition include benzalkonium chloride, chlorobutanol, paraben and thimerosal.

An injectable formulation may comprise a pharmaceutically acceptable excipient such as Ringer Lactate.

The term "carrier" refers to an organic or inorganic component, of a natural or synthetic nature, in which the active component is combined in order to facilitate, enhance or enable application. According to the invention, the term "carrier" also includes one or more compatible solid or liquid fillers, diluents or encapsulating substances, which are suitable for administration to a patient.

Possible carrier substances for parenteral administration are e.g. sterile water, Ringer, Ringer lactate, sterile sodium chloride solution, polyalkylene glycols, hydrogenated naphthalenes and, in particular, biocompatible lactide polymers, lactide/glycolide copolymers or polyoxyethylene/polyoxypropylene copolymers.

The term "excipient" when used herein is intended to indicate all substances which may be present in a pharmaceutical composition and which are not active ingredients such as, e.g., carriers, binders, lubricants, thickeners, surface active agents, preservatives, emulsifiers, buffers, flavoring agents, or colorants.

The agents and compositions described herein may be administered via any conventional route, such as by parenteral administration including by injection or infusion. Administration is preferably parenterally, e.g. intravenously, intraarterially, subcutaneously, intradermally or intramuscularly.

Compositions suitable for parenteral administration usually comprise a sterile aqueous or nonaqueous preparation of the active compound, which is preferably isotonic to the blood of the recipient. Examples of compatible carriers and solvents are Ringer solution and isotonic sodium chloride solution. In addition, usually sterile, fixed oils are used as solution or suspension medium.

The agents and compositions described herein are administered in effective amounts. An "effective amount" refers to the amount which achieves a desired reaction or a desired effect alone or together with further doses. In the case of treatment of a particular disease or of a particular condition, the desired reaction preferably relates to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition.

An effective amount of an agent or composition described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the agents described herein may depend on various of such parameters. In the case that a reaction in a patient is insufficient with an initial dose, higher doses (or effectively higher doses achieved by a different, more localized route of administration) may be used.

The agents and compositions described herein can be administered to patients, e.g., in vivo, to treat or prevent a variety of disorders such as those described herein. Preferred patients include human patients having disorders that can be corrected or ameliorated by administering the agents and compositions described herein. This includes disorders involving cells characterized by expression of CLDN18.2.

For example, in one embodiment, agents described herein can be used to treat a patient with a cancer disease, e.g., a cancer disease such as described herein characterized by the presence of cancer cells expressing CLDN18.2.

The pharmaceutical compositions and methods of treatment described according to the invention may also be used for immunization or vaccination to prevent a disease described herein.

The pharmaceutical composition of the invention may be administered together with supplementing immunity-enhancing substances such as one or more adjuvants and may comprise one or more immunity-enhancing substances to further increase its effectiveness, preferably to achieve a synergistic effect of immunostimulation. The term "adjuvant" relates to compounds which prolongs or enhances or accelerates an immune response. Various mechanisms are possible in this respect, depending on the various types of adjuvants. For example, compounds which allow the maturation of the DC, e.g. lipopolysaccharides or CD40 ligand, form a first class of suitable adjuvants. Generally, any agent which influences the immune system of the type of a "danger signal" (LPS, GP96, dsRNA etc.) or cytokines, such as GM-CSF, can be used as an adjuvant which enables an immune response to be intensified and/or influenced in a controlled manner. CpG oligodeoxynucleotides can optionally also be used in this context, although their side effects which occur under certain circumstances, as explained above, are to be considered. Particularly preferred adjuvants are cytokines, such as monokines, lymphokines, interleukins or chemokines, e.g. IL-1, IL-2, IL-3, IL-4, IL-5, IL-6, IL-7, IL-8, IL-9, IL-10, IL-12, IFNα, IFNγ, GM-CSF, LT-α, or growth factors, e.g. hGH. Further known adjuvants are aluminium hydroxide, Freund's adjuvant or oil such as Montanide®, most preferred Montanide® ISA51. Lipopeptides, such as Pam3Cys, are also suitable for use as adjuvants in the pharmaceutical composition of the present invention.

The pharmaceutical composition can be administered locally or systemically, preferably systemically.

The term "systemic administration" refers to the administration of an agent such that the agent becomes widely distributed in the body of an individual in significant amounts and develops a desired effect. For example, the agent may develop its desired effect in the blood and/or reaches its desired site of action via the vascular system. Typical systemic routes of administration include administration by introducing the agent directly into the vascular system or oral, pulmonary, or intramuscular administration wherein the agent is adsorbed, enters the vascular system, and is carried to one or more desired site(s) of action via the blood.

According to the present invention, it is preferred that the systemic administration is by parenteral administration. The term "parenteral administration" refers to administration of an agent such that the agent does not pass the intestine. The term "parenteral administration" includes intravenous administration, subcutaneous administration, intradermal administration or intraarterial administration but is not limited thereto.

Administration may also be carried out, for example, orally, intraperitonealy or intramuscularly.

The agents and compositions provided herein may be used alone or in combination with conventional therapeutic regimens such as surgery, irradiation, chemotherapy and/or bone marrow transplantation (autologous, syngeneic, allogeneic or unrelated).

The present invention is described in detail by the figures and examples below, which are used only for illustration purposes and are not meant to be limiting. Owing to the description and the examples, further embodiments which are likewise included in the invention are accessible to the skilled worker.

FIGURES

FIG. 1: Representation of the TCR-CD3 complex. The intracytoplasmic CD3 immunoreceptor tyrosine-based activation motifs (ITAMs) are indicated as cylinders (adapted from "The T cell receptor facts book", MP Lefranc, G Lefranc, 2001).

FIG. 2: The design of successive generations of CARs. Schematic representation of the different generations of CARs (1G, first generation, 2G, second generation, 3G, third generation). The first generation contains extracellular scFvs and the cytoplasmic CD3 chain/ZAP70 mediating cytotoxicity, the second generation additionally CD28/PI3K promoting proliferation and the third generation furthermore 4-1BB or OX40/TRAF sustaining cell survival (Casucci, M. et al. (2011) 2: 378-382).

Figure 3:
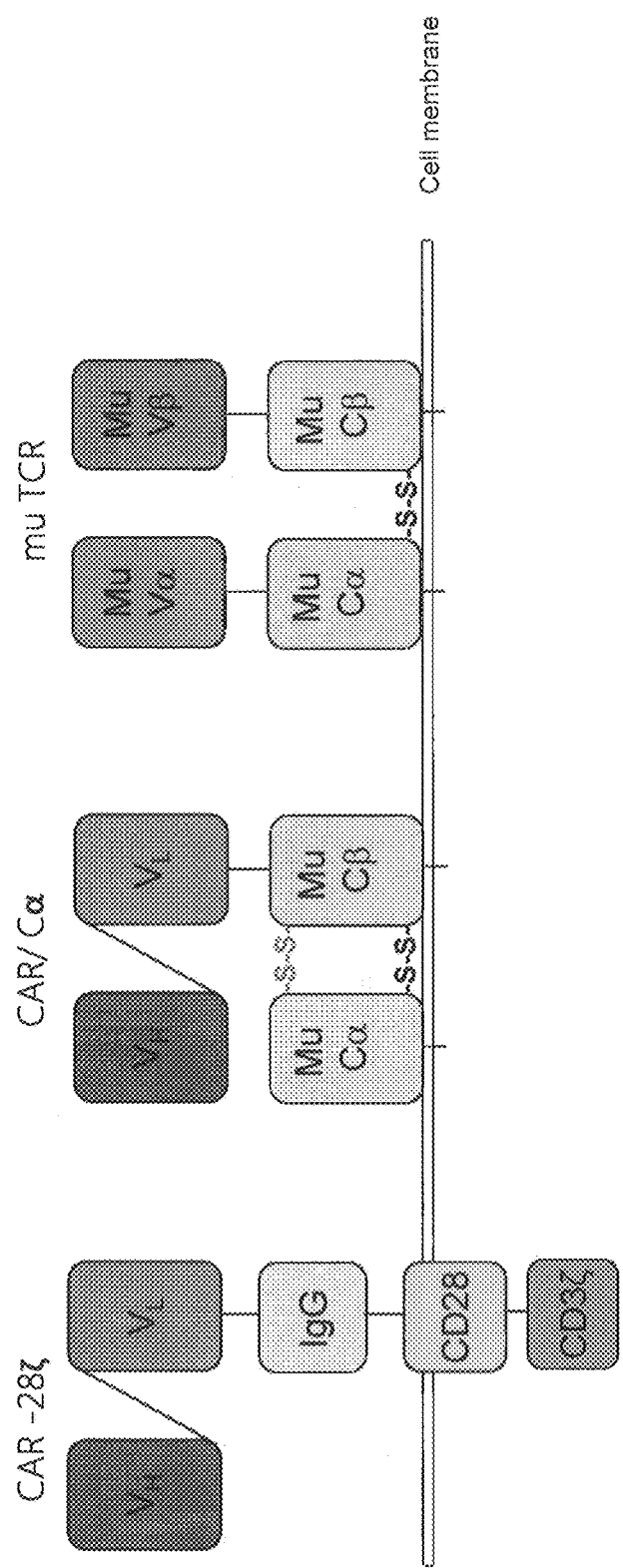
Figure 4:
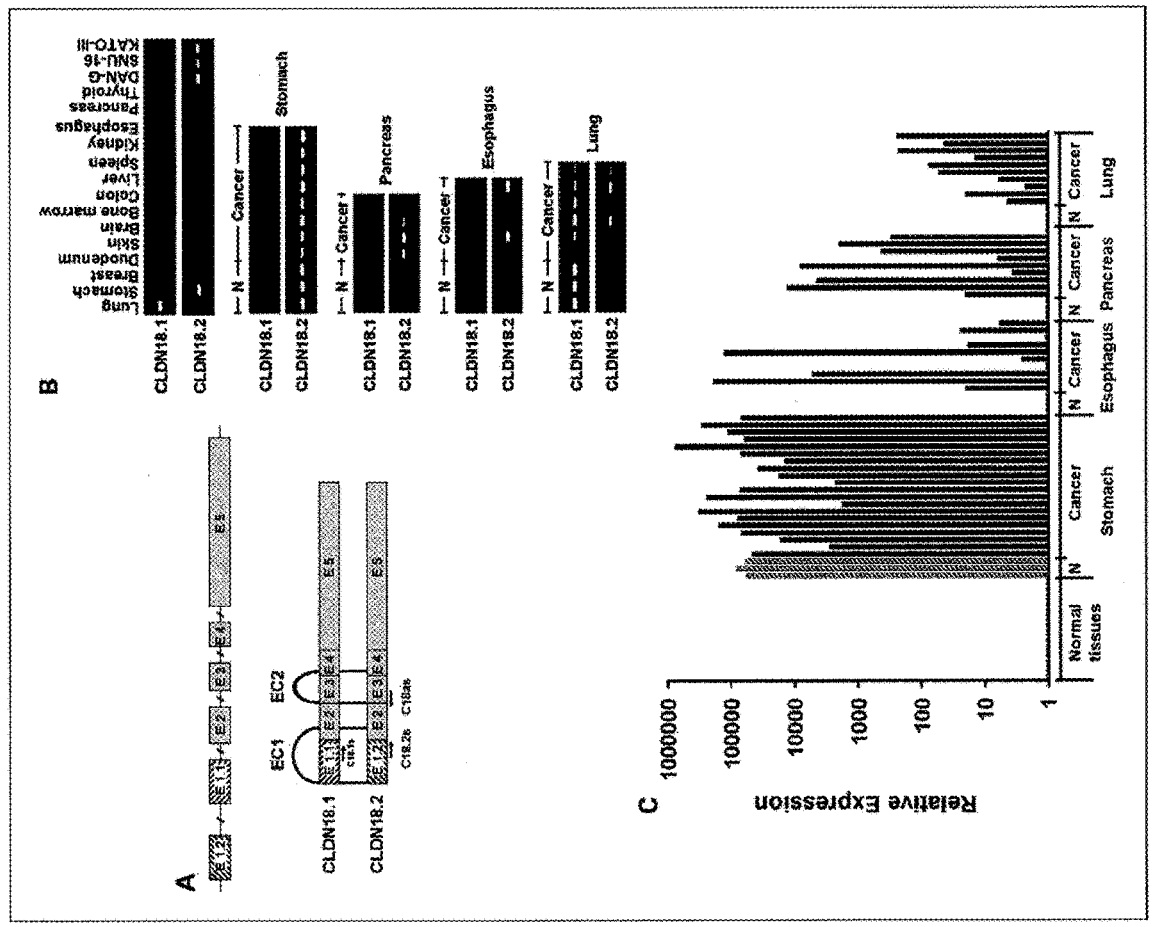

FIG. 3: Schematic representation of the different receptor formats for the redirection of T cells against CLDN18.2. Left: a second generation CAR consisting of a CLDN18.2-specific scFv fragment, a IgG1-derived spacer domain, a CD28 costimulatory and a CD3ζ signaling domain (CAR-28ζ); middle: a novel CAR format based on the linkage of the scFv with the constant domain of the murine TCRß chain and coexpression of the constant domain of the murine TCRα chain (CAR/Cα); right: a murine TCR composed of TCR α/β chains (mu, murine TCR);

FIG. 4: Profiling of CLDN18.1 and CLDN18.2 transcripts in a panel of human tissues. A, genomic structure of the CLDN18 locus (top). Hatched boxes, exons unique for CLDN18.1 (E 1.1) or CLDN18.2 (E 1.2), respectively; bottom, exon composition of CLDN18 variants; arches, the two extracellular domains; arrows, the primers used for RT-PCR. B, comparative analysis of the CLDN18 isoforms in normal human tissues (N), primary tumor specimen, and tumor cell lines by end-point RT-PCR. C, quantification in normal human tissues (N), primary tumor specimen, and tumor cell lines by real-time PCR (Sahin U et al., Clin Cancer Res 2008; 14:7624-34).

Figure 5:
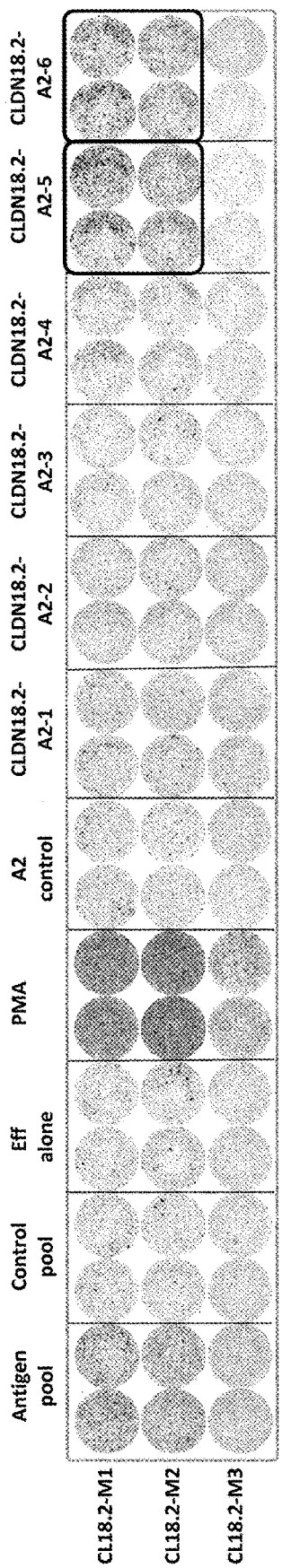

FIG. 5: Ex-vivo reactivity of spleen cells from immunized HLA-A*02-transgenic mice against CLDN18.2-derived peptides analyzed by IFNy-ELISPOT assay. HLA-A*02 CLDN18.2-specific binding peptides were predicted for the first 80 amino acids of CLDN18.2 applying a specific algorithm (Rammensee H. et al. (1999) Immunogenetics 50, 213-9). Spleen cells of CLDN18.2-immunized HLA-A*02-transgenic mice were analyzed for reactivity against CLDN18.2 peptide pool or predicted HLA-A*02-binding CLDN18.2-derived peptides CLDN18.2-A2-1-6. Positive control: PMA-treated spleen cells; negative control: an irrelevant peptide pool (HIV-gag), irrelevant nonamer peptide (PLAC1-31-39).

Figure 6:
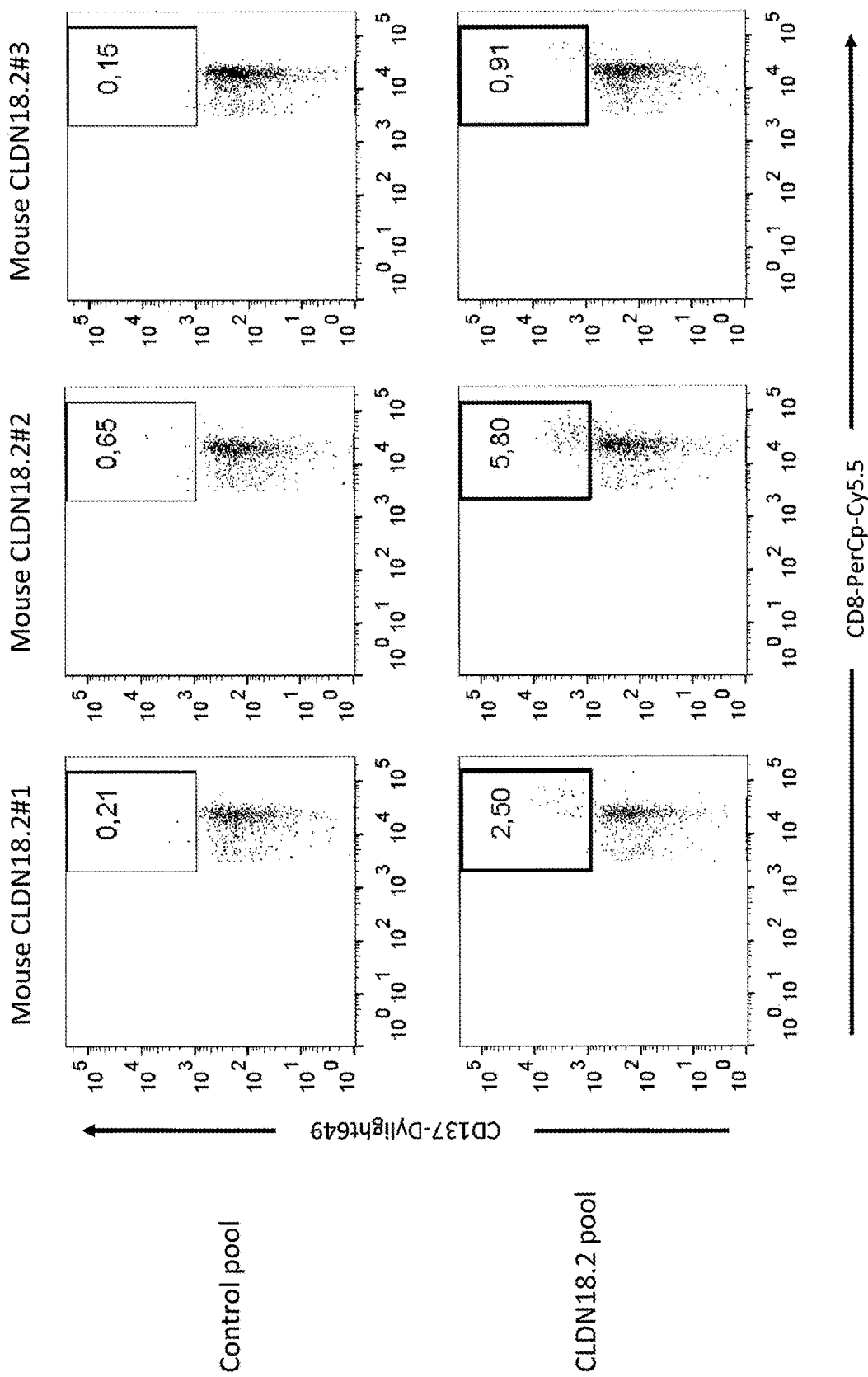

FIG. 6: Flow cytometry sorting of CLDN18.2-specific murine CD8+ T cells from HLA-A*02-transgenic mice after in-vitro restimulation. Single CD8+/CD137+ T cells were isolated after restimulation of spleen cells with CLDN18.2 overlapping peptide pool. Control: spleen cells restimulated with irrelevant peptide pool (HIV-gag).

Figure 7:
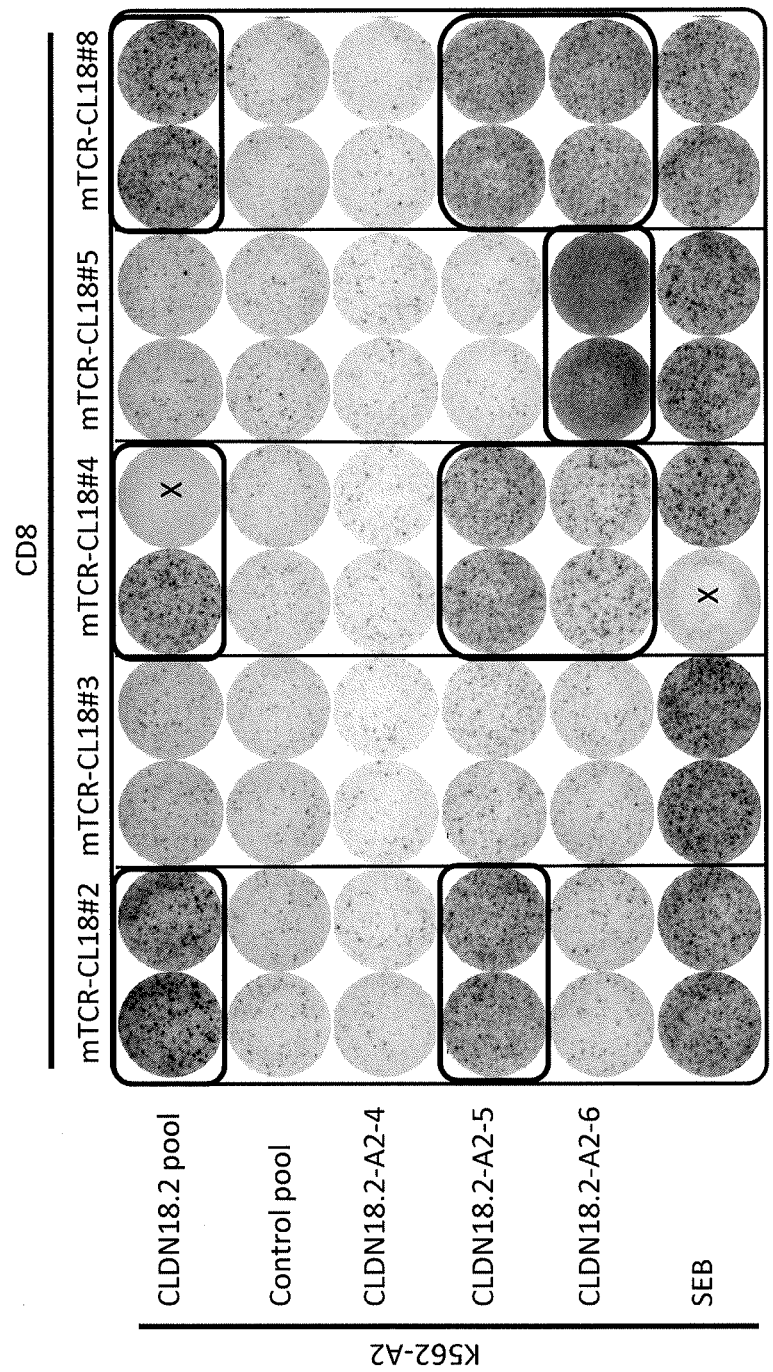
Figure 8:
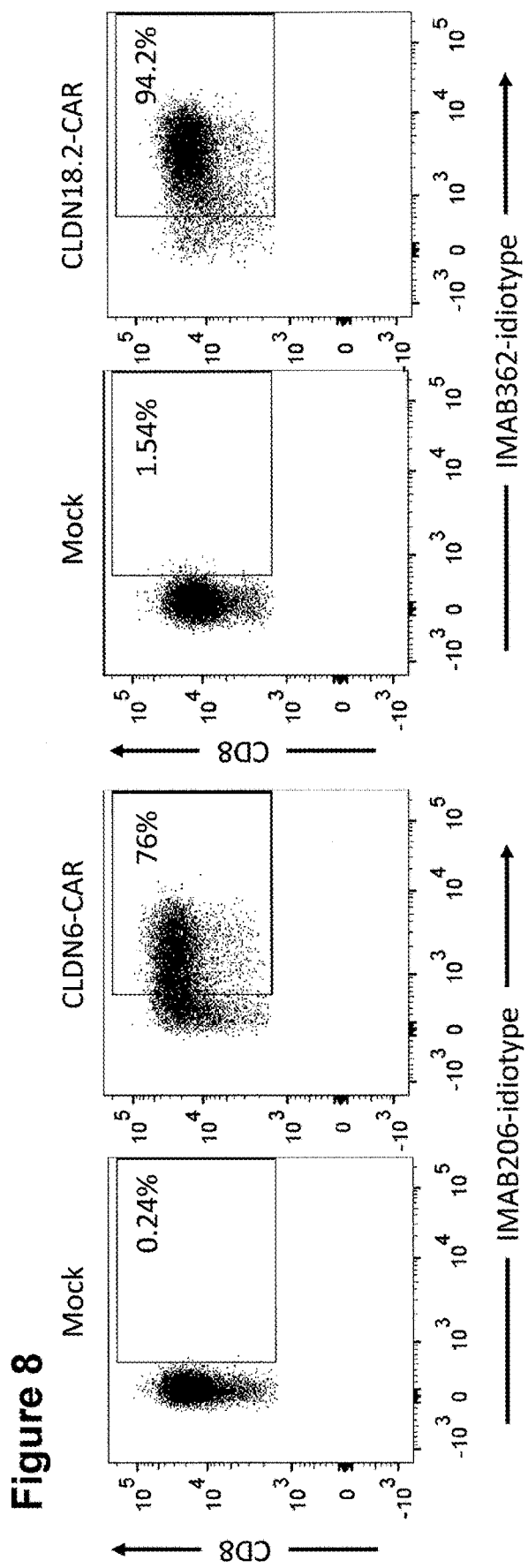

FIG. 7: Specificity testing of TCRs isolated from CD8+ T cells of CLDN18.2-immunized mice. CD8+ T cells of a HLA-A*02-positive healthy donor were transfected with TCR-α/β chain RNAs and tested for recognition of K562-A2 cells pulsed with CLDN18.2 overlapping 15 mer peptides (=CLDN18.2 pool) or CLDN18.2-derived HLA-A*02 binding peptides (CLDN18.2-A2-4, CLDN218.2-A2-5, CLDN18.2-A2-6) by IFNy-ELISPOT. Negative controls: irrelevant peptide pool (HIV-gag), irrelevant 9 mer peptide (PLAC1-31-39); Positive control: SEB;

FIG. 8: Surface expression of CLDN18.2- and CLDN6-specific CARs on human preactivated CD8+ T cells. CD8+ T cells were preactivated with OKT3 and transfected with 20 µg CAR-RNA. 20 h after electroporation cells were stained with a PE-conjugated anti-CD8 antibody and idiotype-specific flurochrome-conjugated antibodies specific for the CLDN18.2-CAR and the CLDN6-CAR, respectively. Cells were gated on single CD8+T lymphocytes.

Figure 9:
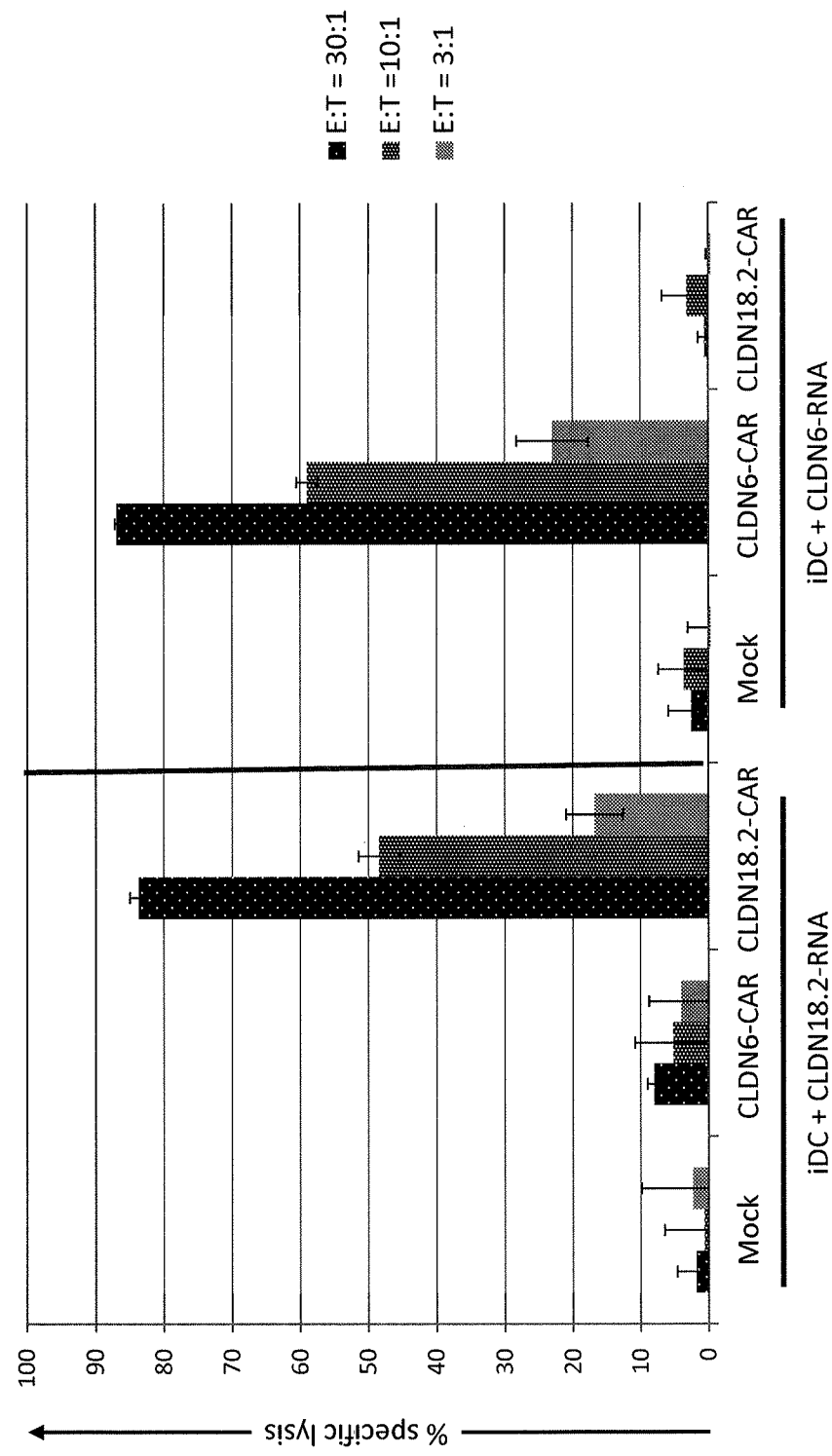

FIG. 9: Specific lysis of CLDN18.2-expressing target cells mediated by the CLDN18.2-CARs. Preactivated CD8+ T cells were transfected with 20 µg CAR RNA and cocultured 20 h later together with autologous iDCs transfected with RNA encoding either with CLDN18.2-CAR using titrated E:T ratios (30:1, 10:1, 3:1). Negative controls: T cells transfected with a CLND6-specific CAR or without CAR RNA (=mock), iDCs transfected with CLDN6-RNA. Specific lysis was analyzed by luciferase-based cytotoxicity assay after 4h coculture.

Figure 10:
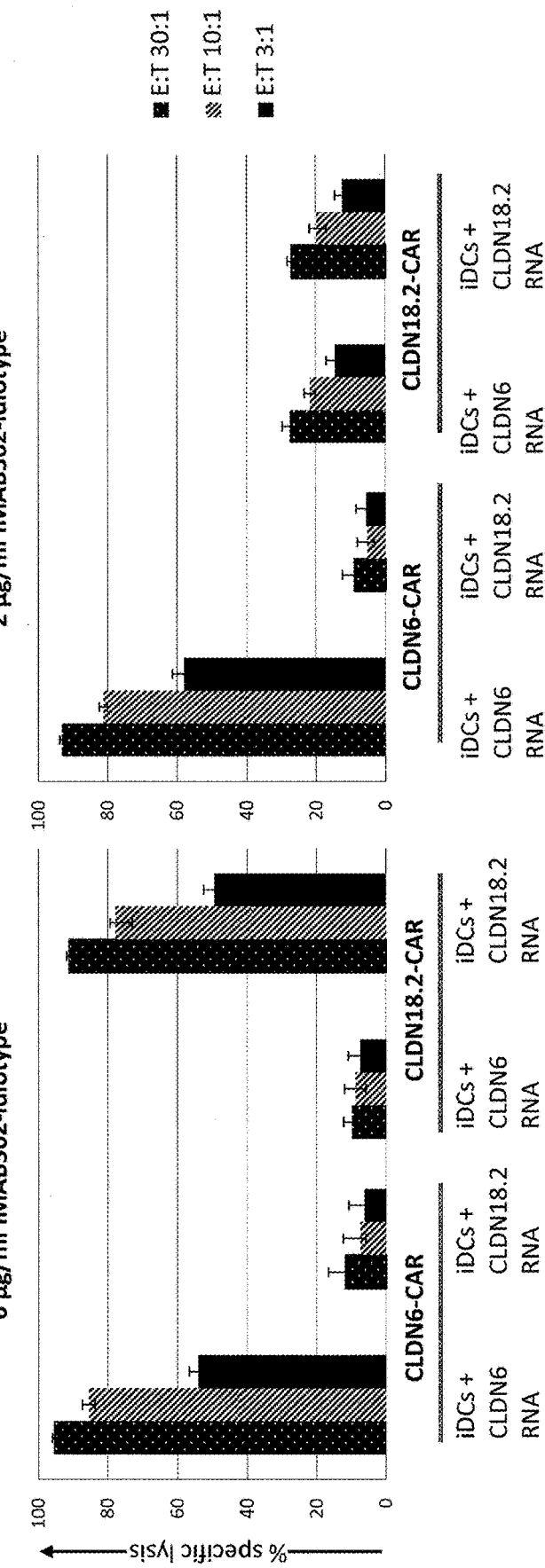

FIG. 10: Specific inhibition of CLDN18.2-CAR mediated lysis of CLDN18.2-expressing target cells by addition of an idiotype-specific antibody. Preactivated CD8+ T cells were transfected with 20 µg CAR RNA and cocultured 20 h later together with autologous iDCs transfected either with CLDN18.2- or with CLDN6-RNA using an E:T ratio of 30:1. Effector T cells were preincubated with or without 2 µg/ml of an idiotype-specific antibody for 1h before target cells were added. Specific lysis was analyzed by luciferase-based cytotoxicity assay after 4h coculture.

Figure 11A:
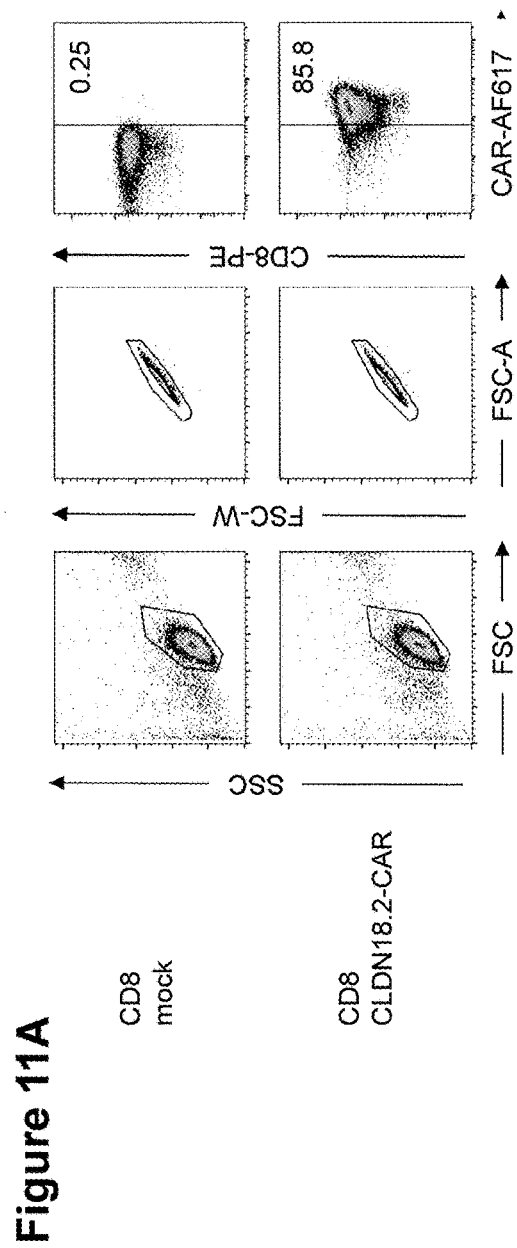
Figure 11B:
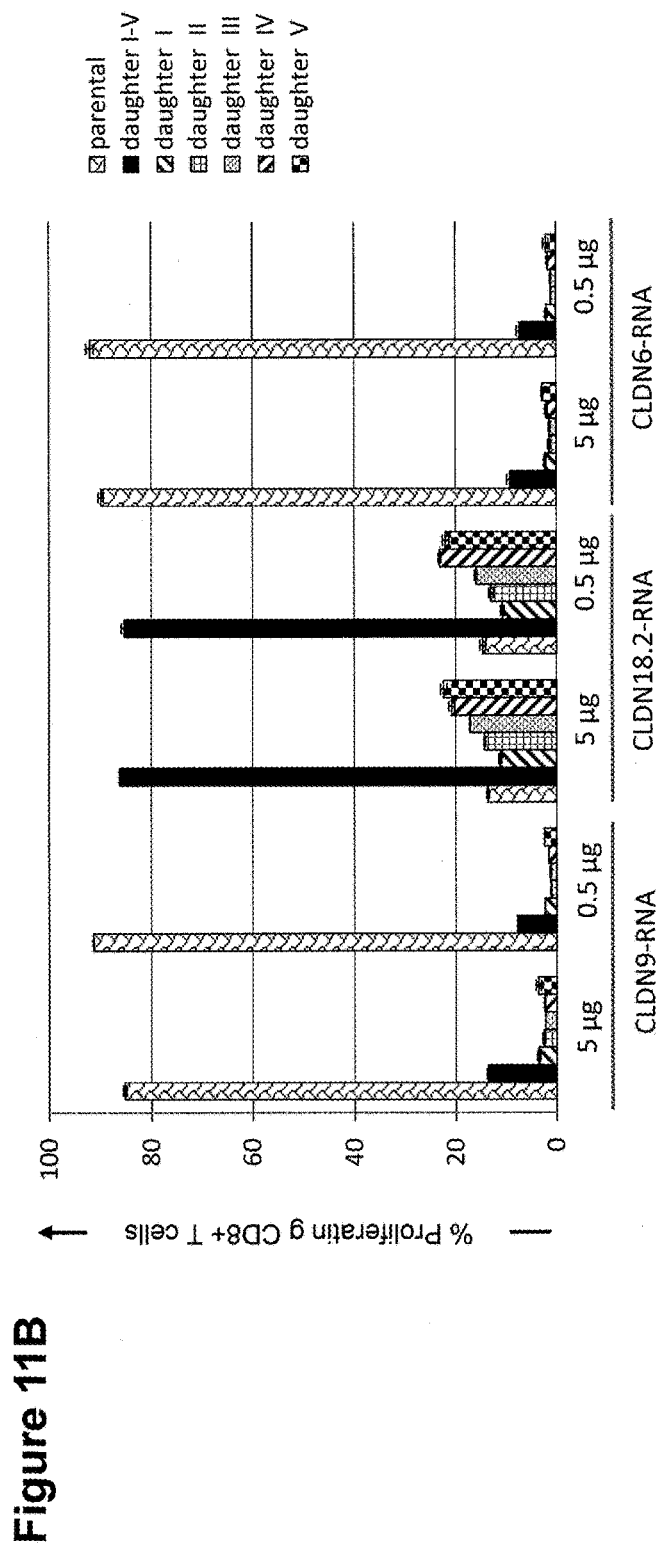

FIG. 11A-11B: In vitro antigen-specific proliferation of CLDN18.2-CAR T cells. CD8+ T cells were electroporated with RNA encoding either the CLDN18.2-CAR or without RNA (mock) and labeled with carboxyfluorescein succinimidyl ester (CFSE). CAR T cells were co-cultured with iDCs transfected with 5 µg IVT-RNA encoding either CLDN18.2 or the control antigens CLDN9 or CLDN6. After 96 h co-culture cells were harvested, and the CFSE fluorescence was analyzed by flow cytometry. Cells were gated on CD8+ living single lymphocytes.

Figure 12A:
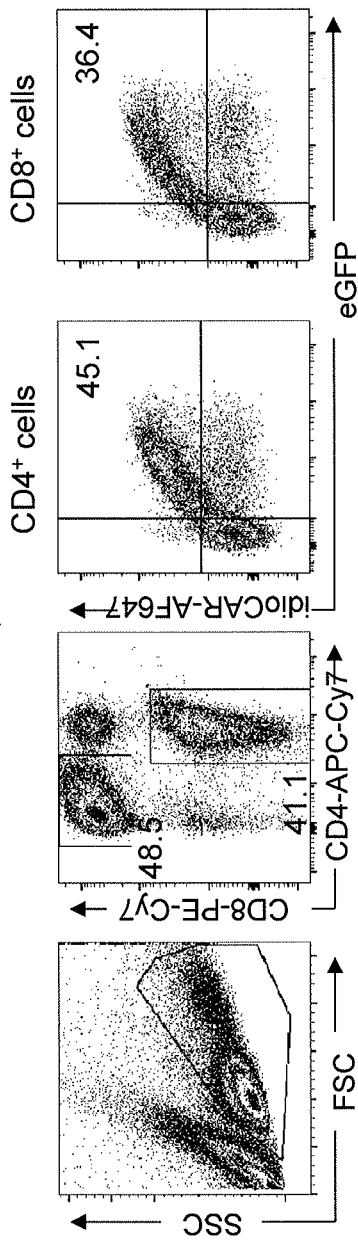
Figure 12B:

FIG. 12A-12B: In vivo antigen-specific activation of CLDN18.2-CAR T cell in mice after vaccination. BALB/c-mice were i.v. engrafted with 5×10⁶ CLDN18-2-CAR-ef-fLuc-GFP transduced T cells. 24 h after ACT, mice were vaccinated i.v. with $RNA_{(F12-Lip)}$ comprising 25 µg CLDN18.2 RNA or Ctrl RNA. FIG. 12A: Transduction efficiency of T cells was measured via flow cytometry using fluorochrome-coupled antibodies FIG. 12B: In vivo-luminescence intensities in mice were measured 48 h after vaccination. Off-color images represent light intensity (black, least intense; white up to dark-grey, most intense) which was superimposed over the greyscale reference photo.

EXAMPLES

The techniques and methods used herein are described herein or carried out in a manner known per se and as described, for example, in Sambrook et al., Molecular Cloning: A Laboratory Manual, 2$^{nd}$ Edition (1989) Cold Spring Harbor Laboratory Press, Cold Spring Harbor, N.Y.

All methods including the use of kits and reagents are carried out according to the manufacturers' information unless specifically indicated.

Example 1: Materials and Methods

Cell Lines and Reagents

The human chronic myeloid leukemia cell line K562 (Lozzio, C. B. & Lozzio, B. B (1975), Blood 45, 321-334) stably transfected with HLA-A*0201 (Britten, C. M. et al. (2002), J. Immunol. Methods 259, 95-110) (referred to e.g. as K562-A2) and used for TCR validation assays was cultured under standard conditions. The primary human newborn foreskin fibroblast cell line CCD-1079Sk (ATCC No. CRL-2097) was cultured according to the manufacturers' instructions.

Peripheral Blood Mononuclear Cells (PBMCs), Monocytes and Dendritic Cells (DCs)

PBMCs were isolated by Ficoll-Hypaque (Amersham Biosciences, Uppsala, Sweden) density gradient centrifugation from buffy coats. HLA allelotypes were determined by PCR standard methods. Monocytes were enriched with anti-CD14 microbeads (Miltenyi Biotech, Bergisch-Gladbach, Germany). Immature DCs (iDCs) were obtained by differentiating monocytes for 5 days in cytokine-supplemented culture medium as described in Kreiter et al. (2007), Cancer Immunol. Immunother., CII, 56, 1577-87.

Peptides and Peptide Pulsing of Stimulator Cells

Pools of N- and C-terminally free 15-mer peptides with 11 amino acid overlaps corresponding to sequences of Claudin-18.2 or HIV-gag (referred to as antigen peptide pool) were synthesized by standard solid phase chemistry (JPT GmbH, Berlin, Germany) and dissolved in DMSO to a final concentration of 0.5 mg/ml. Nonamer peptides were reconstituted in PBS 10% DMSO. For pulsing stimulator cells were incubated for 1 h at 37° C. in culture medium using different peptide concentrations.

Vectors for In Vitro Transcription (IVT) of RNA

All constructs are variants of the previously described pST1-sec-insert-213gUTR-A(120)-Sap1 plasmid (Holtkamp, S. et al. (2006), Blood 108, 4009-4017). For generation of plasmids encoding murine TCR chains, cDNAs coding for murine TCR-α, -$β_1$ and -$β_2$ constant regions were ordered from a commercial provider and cloned analogously (GenBank accession numbers M14506, M64239 and X67127, respectively). Specific V(D)J PCR products were introduced into such cassettes to yield full-length TCR chains (referred to as pST1-murineTCRαß-2ßgUTR-A(120)).

Full-length CLDN18.2, CLDN18.2 aa 1-80 and CLDN6 antigens were cloned linked to the MHC class I trafficking signal (MITD) in pST1 plasmids previously described (Kreiter, S. et al. (2008), J. Immunol. 180, 309-318).

Generation of In Vitro Transcribed (IVT) RNA and Transfer into Cells

Generation of IVT RNA was performed as described previously (Holtkamp, S. et al. (2006), Blood 108, 4009-4017) and added to cells suspended in X-VIVO 15 medium (Lonza, Basel, Switzerland) in a pre-cooled 4-mm gap sterile electroporation cuvette (Bio-Rad Laboratories GmbH, Munich, Germany). Electroporation was performed with a Gene-Pulser-II apparatus (Bio-Rad Laboratories GmbH, Munich, Germany) (T cells: 450 V/250 µF; K562-A2: 200 V/300 µF).

In Vivo Priming of T Cells by Intranodal Immunization of HLA A2.1/DR1 Mice with IVT RNA T cells of A2/DR1 mice (Pajot A. et al. (2004), Eur. J. Immunol. 34, 3060-69) were primed in vivo against the antigen of interest by repetitive intranodal immunization using antigen-encoding IVT RNA (Kreiter S. et al. (2010), Cancer Research 70, 9031-40). For intranodal immunizations, mice were anesthetized with xylazine/ketamine. The inguinal lymph node was surgically exposed, 10 μL RNA (20 μg) diluted in Ringer's solution and Rnase-free water were injected slowly using a single-use 0.3-ml syringe with an ultrafine needle (31G, BD Biosciences), and the wound was closed. After six immunization cycles the mice were sacrificed and spleen cells were isolated.

Harvest of Spleen Cells

Following their dissection under sterile conditions, the spleens were transferred to PBS containing falcon tubes. The spleens were mechanically disrupted with forceps and the cell suspensions were obtained with a cell strainer (40 μm). The splenocytes were washed with PBS centrifuged and resuspended in a hypotonic buffer for lysis of the erythrocytes. After 5 min incubation at RT, the reaction was stopped by adding 20-30 ml medium or PBS. The spleen cells were centrifuged and washed twice with PBS.

Single-Cell Sorting of Antigen-Specific CD8+ T Cells after CD137 Staining

For antigen-specific restimulation $2.5 \times 10^{\wedge}6$/well spleen cells from immunized A2/DR1 mice were seeded in a 24-well plate and pulsed with a pool of overlapping peptides encoding the antigen of interest or a control antigen. After 24 h incubation cells were harvested, stained with a FITC-conjugated anti-CD3 antibody, a PE-conjugated anti-CD4 antibody, a PerCP-Cy5.5-conjugated anti-CD8 antibody and a Dylight-649-conjugated anti-CD137 antibody. Sorting was conducted on a BD FACS Aria flow cytometer (BD Biosciences). Cells positive for CD137, CD3 and CD8 were sorted, one cell per well was harvested in a 96-well V-bottom-plate (Greiner Bio-One) containing human CCD-1079Sk cells as feeder cells, centrifuged at 4° C. and stored immediately at −80° C.

RNA Extraction, SMART-Based cDNA Synthesis and Unspecific Amplification from Sorted Cells RNA from sorted T cells was extracted with the RNeasy Micro Kit (Qiagen, Hilden, Germany) according to the instructions of the supplier. A template-switch protocol was used for cDNA synthesis: Mint Reverse Transcriptase (Evrogen JSC) was combined with oligo(dT)-T-primer long for priming of the first-strand synthesis reaction and TS-short (Eurofins Genomic) introducing an oligo(riboG) sequence to allow for creation of an extended template by the terminal transferase activity of the reverse transcriptase and for template switch (Matz, M. et al. (1999) Nucleic Acids Res. 27, 1558-1560). First strand cDNA synthesized according to the manufacturer's instructions was subjected to 21 cycles of amplification with 5 U PfuUltra Hotstart High-Fidelity DNA Polymerase (Agilent Technologies) and 0.48 μM primer TS-PCR primer in the presence of 200 μM dNTP (cycling conditions: 2 min at 95° C. for, 30 s at 94° C., 30 s at 65° C., 1 min at 72° C. for, final extension of 6 min at 72° C.). Successful amplification of TCR genes was controlled with murine TCR-β constant region specific primers and consecutive clonotype-specific murine Vα-/Vβ-PCRs were only performed if strong bands were detected.

Design of PCR Primers for TCR Amplification

For design of murine TCR consensus primers, all functional murine TCR-Vβ and -Vα genes as listed in the ImMunoGeneTics (IMGT) database (http://www.imgt.org) together with their corresponding leader sequences were aligned with the BioEdit Sequence Alignment Editor (e.g. http://www.bio-soft.net). Forward primers of 24 to 27 bp length with a maximum of 3 degenerated bases, a GC-content between 40-60% and a G or C at the 3'end were designed to anneal to as many leader sequences as possible and equipped with a 15 bp 5'extension featuring a rare restriction enzyme site and Kozak sequence. Reverse primers were designed to anneal to the first exons of the constant region genes, with primer mTRACex1_as binding to sequences corresponding to amino acids 24 to 31 of Cα and mTRBCex1_as to amino acids (aa) 8 to 15 in Cβ1 and Cβ2. Both oligonucleotides were synthesized with a 5' phosphate. Primers were bundled in pools of 2-6 forward oligos with identical annealing temperature.

PCR Amplification and Cloning of V(D)J Sequences

6 μl of preamplified cDNA from isolated T cells was subjected to 40 cycles of PCR in the presence of 0.6 μM mVα-/mVβ-specific oligo pool, 0.6 μM mCα- or mCβ-oligo, 200 μM dNTP and 5 U PfuUltra II Fusion HS DNA Polymerase (Agilent; cycling conditions: 1 min at 95° C., 30 s at 94° C., 30 s annealing temperature, 30 s at 72° C., final extension time of 3 min at 72° C.). PCR products were analyzed using Qiagen's capillary electrophoresis system. Samples with bands at 470-550 bp were size fractioned on agarose gels, the bands excised and purified using a Gel Extraction Kit (Qiagen, Hilden, Germany). Sequence analysis was performed to reveal the sequence of both the V(D)J domain and 13 constant region, as mTRBCex1_as and mTRBCex1_as primer, respectively, match to both TCR constant region genes Cβ1 and Cβ2 in mouse. DNA was digested and cloned into the IVT vectors containing the appropriate backbone for a complete murine TCR-α/β chain.

Flow Cytometric Analyses

Cell surface expression of transfected TCR genes was analyzed by flow cytometry using fluorochrome-conjugated anti-TCR antibody against the appropriate variable region family or the constant region of the TCR β chain (Beckman Coulter Inc., Fullerton, USA) in combination with antibodies directed against CD3, CD8 or CD4 (BD Biosciences). Cell surface expression of transfected CARs was analyzed using a fluorochrome-conjugated idiotype-specific antibodies (Ganymed Pharmaceuticals) recognizing the scFv fragments contained in the respective CAR construct. Flow cytometric analysis was performed on a FACS CANTO II flow cytometer using the FACS Diva software (BD Biosciences).

Luciferase Cytotoxicity Assay

For assessment of cell-mediated cytotoxicity a bioluminescence-based assay was used as an alternative and optimization to $^{51}$Cr release. In contrast to the standard chromium release assay, this assay measures lytic activity of effector cells by calculating the number of viable luciferase expressing target cells following coincubation. The target cells were stably or transiently transfected with the luciferase gene coding for the firefly luciferase from firefly Photinus pyralis (EC 1.13.12.7). Luciferase is an enzyme catalyzing the oxidation of luciferin. The reaction is ATP-dependent and takes place in two steps:

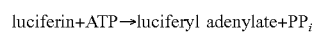

luciferin+ATP→luciferyl adenylate+PP$_i$

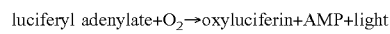

luciferyl adenylate+O$_2$→oxyluciferin+AMP+light

Target cells were plated at a concentration of $10^4$ cells per well in white 96-well plates (Nunc, Wiesbaden, Germany) and were cocultivated with varying numbers of TCR-transfected T cells in a final volume of 100 µl. 3 h later 50 µl of a D-Luciferin (BD Biosciences) containing reaction mix (Luciferin (1 µg/µl), HEPES-buffer (50 mM, pH), Adenosine 5'-triphosphatase (ATPase, 0.4 mU/µl, Sigma-Aldrich, St. Louis, USA) was added to the cells. By addition of ATPase to the reaction mix luminescence resulting from luciferase released from dead cells was diminished.

After a total incubation time of 4 h bioluminescence emitted by viable cells was measured using the Tecan Infinite 200 reader (Tecan, Crailsheim, Germany). Cell-killing activity was calculated in regard to luminescence values obtained after complete cell lysis induced by the addition of 2% Triton-X 100 and in relationship to luminescence emitted by target cells alone. Data output was in counts per second (CPS) and percent specific lysis was calculated as follows:

$$(1-(CPS_{exp}-CPS_{min})/(CPS_{max}-CPS_{min})) \ast 100.$$

Maximum luminescence (maximum counts per second, CPSmax) was assessed after incubating target cells without effectors and minimal luminescences (CPSmin) was assessed after treatment of targets with detergent Triton-X-100 for complete lysis.

ELISPOT (Enzyme-Linked ImmunoSPOT Assay)

Microtiter plates (Millipore, Bedford, Mass., USA) were coated overnight at room temperature either with an anti-human IFNγ antibody 1-D1k (Mabtech, Stockholm, Sweden) or overnight at 4° C. with an anti-murine IFNy antibody AN18 (Mabtech) and blocked with 2% human albumin (CSL Behring, Marburg, Germany) or with murine culture medium. In the murine setting $5\times10^5$ spleen cells were distributed per well, while in the human setting $2-5\times10^4$/well antigen presenting stimulator cells were plated in triplicates together with $0.3-3\times10^5$/well TCR-transfected CD4+ or CD8+ effector cells 24 h after electroporation. The plates were incubated overnight (37° C., 5% $CO_2$), washed with PBS 0.05% Tween 20, and incubated for 2 hours with the anti-human IFNγ biotinylated mAB 7-B6-1 (Mabtech) or anti-murine IFNγ biotinylated mAb R4-6A2 (Mabtech) at a final concentration of 1 µg/ml at 37° C. Avidin-bound horseradish peroxidase H (Vectastain Elite Kit; Vector Laboratories, Burlingame, USA) was added to the wells, incubated for 1 hour at room temperature and developed with 3-amino-9-ethyl carbazole (Sigma, Deisenhofen, Germany).

CFSE (Carboxyfluorescein Succinimidyl Ester) Proliferation Assay

CD8+ T cells were transfected with CAR RNA and about 20h later labeled with 0.8 µM CFSE. Labeled T cells were washed and cocultured with RNA-transfected autologous iDCs (E:T ratio=10:1). After 4 days of coculture cells were harvested and proliferation was analyzed by flow cytometry based on the progressive halving of CFSE fluorescence within daughter cells following cell divisions.

Animals

BALB/c mice were purchased from Javier Labs. Age (8 weeks old) and sex (female) matched animals were used throughout the experiments. Congenic BALB/c-Thy1.1 mice were bred in the animal facility of the BioNTech AG, Germany Retroviral Gene Manipulation and Preparation of CAR T Cells for Adoptive T Cell Transfer Splenocytes of BALB/c-Thy1.1 mice were isolated and pre-activated by 2 µg/mL soluble anti-CD3 (eBioscience) and 1 µg/mL soluble anti-CD28 (Novus Biologicals) in the presence of 5 ng/mL rh IL-7 and 10 ng/mL rh IL-15 (both Miltenyi). 24 h and 48 h after pre-activation, T cells were retrovirally (MLV-E) transduced with tricistronic vector encoding CLDN18.2-CAR-effLuc-GFP using RetroNectin-technique (Takara). Transduced T cells were then 3 days expanded in the presence of 5 ng/mL rh IL-7 and 10 ng/mL rh IL-15 and were subsequently ficoll cleaned with Ficoll-Paque PREMIUM (1.084) prior adoptive transfer into mice.

Mouse Experiments $5\times10^6$ CLDN18.2 CAR transduced BALB/c-Thy1.1+ T cells were intravenously (i.v.) transferred into BALB/c mice. Subsequently, mice were i.v. vaccinated with an F12:RNA ratio of 1.3:2 of $RNA_{(Lip)}$ 24 hours after adoptive T cells transfer (ACT). Whole body bioluminescence imaging was performed.

In Vivo Bioluminescence Imaging (BLI)

Expansion of CLDN18.2-CAR-effLuc-GFP transduced T cells was evaluated by in vivo bioluminescence imaging using the IVIS Lumina imaging system (Caliper Life Sciences). Briefly, 5 min after injection of an aqueous solution of D-luciferin (80 mg/kg body weight; Perkin Elmer), emitted photons were quantified (integration time of 1 min). The intensity of transmitted light originating from luciferase expressing cells within the animal was represented as a greyscale image, where black is the least intense and white to dark-grey the most intense bioluminescence signal. Greyscale reference images of mice were obtained under LED low light illumination. The images were superimposed using the Living Image 4.0 software.

Example 2: Isolation of High-Affinity HLA-A*02-Restricted Murine TCRs Specific for Claudin-18.2

We validated the immunogenic potential of CLDN18.2 in A2/DR1 mice by repetitive intranodal immunization with IVT-RNA encoding aa 1-80 of CLDN18.2. The human CLDN18 gene has two alternative first exons, giving rise to two protein isoforms (CLDN18.1 and CLDN18.2) differing in the N-terminal 69 amino acids (FIG. 4A). As CLDN18.1 is also expressed in normal tissues, especially in the lung, we only used the N-terminal part of CLDN18.2 in order to exclusively induce CLDN18.2-specific T cell reactivities. We used spleen cells of these mice for isolation of CLDN18.2-specific T cells and subsequent cloning of the corresponding TCR genes. Spleen cells of immunized mice were analyzed for the successful induction of CLDN18.2-specific T cells and their reactivity against predicted HLA-A*02 binding CLDN18.2 peptides ex-vivo by IFNγ-ELISPOT assay (FIG. 5).

Significant frequencies of CLDN18.2-specific T cells could be induced In all three mice by RNA immunization, whereas T cell reactivity was focused on two CLDN18.2 peptides predicted to bind to HLA-A*0201(CLDN18.2-A2-5 and -CLDN18.2-A2-6).

For isolation of CLDN18.2-specific T cells, spleen cells of immunized mice were restimulated in-vitro and single cells were isolated by flowcytometry based on the activation-induced upregulation of CD137 (FIG. 6).

CLDN18.2-specific CD8+ T cells could be retrieved from all three immunized A2/DR1 mice and a total of 6 CLDN18.2-specific TCRs were cloned from single-sorted murine T cells. TCRs were subjected to immunological validation assays, which revealed that all six CLDN18.2-TCRs recognized one or both of the two HLA-A*0201-restricted epitopes CLDN18.2 aa 7-15 (CLDN18.2-A2-5) and CLDN18.2 aa 8-16 (CLDN18.2-A2-6), which were previously identified by ex-vivo ELISPOT analysis (FIG. 7).

Example 3: Generation and In-Vitro Validation of a Claudin-18.2-Specific CAR We generated a second generation CAR targeting CLDN18.2 that contains the signaling and costimulatory moieties of CD3 and CD28, respectively. A deletion of the lck binding moiety in the CD28 endodomain abrogates IL2 secretion upon CAR engagement to prevent induction of regulatory T cells (Kofler D. M. et al., (2011) Molecular Therapy 19 (4), 760-767). A modification of the IgG1 Fc 'spacer' domain in the extracellular moiety of the CAR avoids 'off-target' activation and unintended initiation of an innate immune response (Hombach A. et al., (2010) Gene Therapy 17, 1206-1213).

To analyze the specific lysis of CLDN18.2-expressing target cells by CLDN18.2-CAR T cells a luciferase-based cytotoxicity assay was performed. CD8+ T cells were pre-activated and transfected with IVT-RNA encoding either the CLDN18.2-CAR or the CLDN6-specific CAR as a control. CAR surface expression was confirmed after staining with fluorochrome-conjugated antibodies by flowcytometry (FIG. 8). Both CARs were well expressed on the surface of CD8+ T cells. CAR-transfected T cells were cultured with autologous iDCs transfected either with CLDN18.2- or CLDN6-RNA using different effector-to-target ratios and the specific lysis was calculated after 4h of coculture (FIG. 9). Both, the CLDN18.2-CAR and the CLDN6-CAR, mediated specific lysis of iDCs expressing CLDN18.2 and CLDN6, respectively. No lysis could be observed, when iDCs expressed the respective control antigen.

In order to analyze, if the CLDN18.2-CAR-mediated lysis of CLDN18.2-expressing target cells may be inhibited by addition of an idiotype-specific antibody, CAR T cells were preincubated with or without the antibody that specifically binds to the scFv fragment contained in the CLDN18.2-CAR before coculture with target cells was initiated and lysis was analyzed using a luciferase-based cytotoxicity assay (FIG. 10).

The CLDN18.2-CAR-mediated lysis of CLDN18.2-expressing target cells could be efficiently inhibited even with a high E:T ratio of 30:1 by blocking the binding of the CLDN18.2-CAR to its target antigen. No inhibition of the CLDN6-CAR mediated lysis could be observed confirming the selective binding of the antibody to the CLDN18.2-CAR. This experiment confirmed on the one hand that the CLDN18.2-CAR-mediated lysis is exclusively dependent on the CLDN18.2 specificity of the CAR and on the other hand that the idiotype-specific antibody that is used for CLDN18.2-CAR detection could in principle also be applied for inhibition of CLDN18.2-CAR T cells in-vivo in case of a severe adverse event.

An essential prerequisite for the anti-tumoral efficacy of CAR-engineered T cells is their ability to proliferate and persist in the patient. In order to analyze, if CLDN18.2-CAR T cells efficiently proliferate in response to CLDN18.2 ectopically expressed in iDCs, a carboxyfluorescein succinimidyl ester (CFSE) based in vitro co-culture assay was performed. CD8+ T cells transfected with IVT-RNA encoding the CLDN18.2-CAR were labeled with CFSE and co-cultured with autologous iDCs transfected with IVT-RNA encoding either CLDN18.2 or the control antigens CLDN9 or CLDN6. CAR surface expression was analyzed by flow cytometry using a fluorochrome-coupled anti-idiotype-specific antibody (FIG. 11A). After four days of co-culture, the antigen-specific proliferation of CFSE-labeled CAR-transfected CD8+ T cells was analyzed by flow cytometry. The CLDN18.2-CAR mediated proliferation of about 86% of CD8+ T cells in response to CLDN18.2, while only background proliferation of CAR T cells in response to control antigen transfected iDCs (CLDN9, CLDN6) could be observed (FIG. 11B). These data confirm that efficient antigen-specific activation and expansion of CLDN18.2-CAR T cells can be achieved by ectopic CLDN18.2 expression in human iDCs.

The potency of the CLDN18.2-CAR to mediate antigen-specific activation and expansion of CAR bearing T cells in vivo was examined in a syngenic mouse model. To follow the fate of adoptively transferred CAR-T cells in vivo, a tricistronic retroviral vector was used which encodes luciferase (effLuc) and eGFP reporter genes downstream of CLDN18.2-CAR separated by viral T2A sequences.

Naïve BALB/c mice were engrafted with CLDN18.2-CAR transduced murine T cells. At the day of transfer, CLDN18.2-CAR expression on transduced T cells was assessed by flow cytometry using fluorochrome-coupled anti-idiotype-specific antibody in combination with eGFP reporter expression. The CLDN18.2-CAR was highly expressed in about 36% of CD8+ and in about 45% of CD4+ T cells (FIG. 12A). Engrafted mice were then treated with IVT-RNA encoding either CLDN18.2 or a control (Ctrl) antigen. A strong increase of light emission could be observed in CLDN18.2 RNA compared to control RNA treated mice two days after mRNA vaccination indicating significant activation and proliferation of CLDN18.2-CAR T cells in response to the cognate antigen (FIG. 12B). These data clearly showed the functionality and antigen specificity of the CLDN18.2 CAR in T cells in vivo.

```
CLDN18.2-specific T cell epitopes
A2-1 (aa 68-76)
                                                       (SEQ ID NO: 2)
TLLGLPAML A2-2 (aa 71-79)
                                                       (SEQ ID NO: 3)
GLPAMLQAV A2-3 (14-22)
                                                       (SEQ ID NO: 4)
SLIGIAGII A2-4 (17-25)
                                                       (SEQ ID NO: 5)
GIAGIIAAT A2-5 (7-15)
                                                       (SEQ ID NO: 6)
QGLGFVVSL
```

-continued

A2-6 (8-16)
(SEQ ID NO: 7)
GLGFVVSLI

CLDN18.2-specific T cell receptors
mTCR$_{CD8}$-CL18#2
>Alpha V12D.1 J33 C (MN lacks N-terminal; V → G und S → C)
(SEQ ID NO: 8)
MRPGTCSVLVLLLMLRRSNGDSVTQTEGLVTVTEGLPVKLNCTYQTTYLTIAFFWYVQ

YLNEAPQVLLKSSTDNKRTEHQGFHATLHKSSSSFHLQKSSAQLSDSALYYCALMDSNY

QLIWGSGTKLIIKPDIQNPEPAVYQLKDPRSQDSTLCLFTDFDSQINVPKTMESGTFITDK

TVLDMKAMDSKSNGAIAWSNQTSFTCQDIFKETNATYPSSDVPCDATLTEKSFETDMNL

NFQNLSVMGLRILLLKVAGFNLLMTLRLWSS*

>Beta V13.3 D1 J1.4*02 C1
(SEQ ID NO: 9)
MGSRLFFVVLILLCAKHMEAAVTQSPRSKVAVTGGKVTLSCHQTNNHDYMWYRQDT

GHGLRLIHYSYVADSTEKGDIPDGYKASRPSQENFSLILELASLSQTAVYFCASSINERLF

FGHGTKLSVLEDLRNVTPPKVSLFEPSKAEIANKQKATLVCLARGFFPDHVELSWWVNG

KEVHSGVSTDPQAYKESNYSYCLSSRLRVSATFWHNPRNHFRCQVQFHGLSEEDKWPE

GSPKPVTQNISAEAWGRADCGITSASYQQGVLSATILYEILLGKATLYAVLVSTLVVMA

MVKRKNS* mTCR$_{CD8}$-CL18#4
>Alpha V6D.7 *04 J26 C (S → F)
(SEQ ID NO: 10)
MNSITGFMTVMLLIFTRAHGDSVTQTEGQVALSEEDFLTIHCNYSASGYPALFWYVQYP

GEGPQFLFRASRDKEKGSSRGFEATYDKGTTSFHLRKASVQESDSAVYYCALGDYAQG

LTFGLGTRVSVFPYIQNPEPAVYQLKDPRSQDSTLCLFTDFDSQINVPKTMESGTFITDKT

VLDMKAMDSKSNGAIAWSNQTSFTCQDIFKETNATYPSSDVPCDATLTEKSFETDMNL

NFQNLSVMGLRILLLKVAGFNLLMTLRLWSS*

>Beta V2 D2 J2.7 C2 (CASSQEWGGYEQYF)
(SEQ ID NO: 11)
MGSIFLSCLAVCLLVAGPVDPKIIQKPKYLVAVTGSEKILICEQYLGHNAMYWYRQSAK

KPLEFMFSYSYQKLMDNQTASSRFQPQSSKKNHLDLQITALKPDDSATYFCASSQEWGG

YEQYFGPGTRLTVLEDLRNVTPPKVSLFEPSKAEIANKQKATLVCLARGFFPDHVELSW

WVNGKEVHSGVSTDPQAYKESNYSYCLSSRLRVSATFWHNPRNHFRCQVQFHGLSEED

KWPEGSPKPVTQNISAEAWGRADCGITSASYHQGVLSATILYEILLGKATLYAVLVSGL

VLMAMVKKKNS* mTCR$_{CD8}$-CL18#5
>Alpha V6D.7*04 J47 C (N → D und S → F)
(SEQ ID NO: 12)
MDSITGFMTVMLLIFTRAHGDSVTQTEGQVALSEEDFLTIHCNYSASGYPTLFWYVQYP

GEGPQLLFRASRDKEKGSSRGFEATYDKGTTSFHLRKASVQESDSAVYYCALSVDYAN

KMIFGLGTILRVRPHIQNPEPAVYQLKDPRSQDSTLCLFTDFDSQINVPKTMESGTFITDK

TVLDMKAMDSKSNGAIAWSNQTSFTCQDIFKETNATYPSSDVPCDATLTEKSFETDMNL

NFQNLSVMGLRILLLKVAGFNLLMTLRLWSS*

>Beta V1 D2 J2.7 C2
(SEQ ID NO: 13)
MWQFCILCLCLVMASVATDPTVTLLEQNPRWRLVPRGQAVNLRCILKNSQYPWMSWY

QQDLQKQLQWLFTLRSPGDKEVKSLPGADYLATRVTDTELRLQVANMSQGRTLYCTCS

PLTGSYEQYFGPGTRLTVLEDLRNVTPPKVSLFEPSKAEIANKQKATLVCLARGFFPDHV

```
ELSWWVNGKEVHSGVSTDPQAYKESNYSYCLSSRLRVSATFWHNPRNHFRCQVQFHG

LSEEDKWPEGSPKPVTQNISAEAWGRADCGITSASYHQGVLSATILYEILLGKATLYAVL

VSGLVLMAMVKKKNS*
``` mTCR$_{CD8}$-CL18#8
\>Alpha V8D.2*02 or V8N.2 J31 C
(SEQ ID NO: 14)

```
MNRFLGISLVTLWFQVAWAKSQWGEENLQALSIQEGEDVTMNCSYKTYTTVVQWYRQ

KSGKGPAQLILIRSNEREKRSGRLRATLDTSSQSSSLSITGTLATDTAVYFCATDNRIFFG

DGTQLVVKPNIQNPEPAVYQLKDPRSQDSTLCLFTDFDSQINVPKTMESGTFITDKTVLD

MKAMDSKSNGAIAWSNQTSFTCQDIFKETNATYPSSDVPCDATLTEKSFETDMNLNFQN

LSVMGLRILLLKVAGFNLLMTLRLWSS*
```

\>Beta V23 D2 J2.7 C2
(SEQ ID NO: 15)

```
MGARLICYVALCLLGAGSFDAAVTQKPRYLIKMKGQEAEMKCIPEKGHTAVFWYQQK

QSKELKFLIYFQNQQPLDQIDMVKERFSAVCPSSSLCSLGIRTCEAEDSALYLCSSSQSGG

YEQYFGPGTRLTVLEDLRNVTPPKVSLFEPSKAEIANKQKATLVCLARGFFPDHVELSW

WVNGKEVHSGVSTDPQAYKESNYSYCLSSRLRVSATFWHNPRNHFRCQVQFHGLSEED

KWPEGSPKPVTQNISAEAWGRADCGITSASYHQGVLSATILYEILLGKATLYAVLVSGL

VLMAMVKKKNS*
``` mTCR$_{CD8}$-CL18#9
\>Alpha V9N.3 J21 C (P → S)
(SEQ ID NO: 16)

```
MLLALLSVLGIHFLLRDAQAQSVTQPDARVTVSEGASLQLRCKYSYFGTPYLFWYVQY

PRQGLQLLLKYYPGDPVVQGVNGFEAEFSKSNSSFHLRKASVHWSDWAVYFCAVSKY

YNVLYFGSGTKLTVEPNIQNPEPAVYQLKDPRSQDSTLCLFTDFDSQINVPKTMESGTFIT

DKTVLDMKAMDSKSNGAIAWSNQTSFTCQDIFKETNATYPSSDVPCDATLTEKSFETD

MNLNFQNLSVMGLRILLLKVAGFNLLMTLRLWSS*
```

\>Beta V2 D2 J2.7 C2 (CASSQDQGGQGQYF)
(SEQ ID NO: 17)

```
MGSIFLSCLAVCLLVAGPVDPKIIQKPKYLVAVTGSEKILICEQYLGHNAMYWYRQSAK

KPLEFMFSYSYQKLMDNQTASSRFQPQSSKKNHLDLQITALKPDDSATYFCASSQDQGG

QGQYFGPGTRLTVLEDLRNVTPPKVSLFEPSKAEIANKQKATLVCLARGFFPDHVELSW

WVNGKEVHSGVSTDPQAYKESNYSYCLSSRLRVSATFWHNPRNHFRCQVQFHGLSEED

KWPEGSPKPVTQNISAEAWGRADCGITSASYHQGVLSATILYEILLGKATLYAVLVSGL

VLMAMVKKKNS*
``` mTCR$_{CD8}$-CL18#12
\>Alpha V6.3*02 or V6D.3 J26 C (N → T)
(SEQ ID NO: 18)

```
MNTSPALVTVMLFILGRTHGDSVIQMQGQVTLSENDFLFINCTYSTTGYPTLFWYVQYS

GEGPQLLLQVTTANNKGSSRGFEATYDKGTTSFHLQKTSVQEIDSAVYYCAIGNYAQGL

TFGLGTRVSVFPYIQNPEPAVYQLKDPRSQDSTLCLFTDFDSQINVPKTMESGTFITDKTV

LDMKAMDSKSNGAIAWSNQTSFTCQDIFKETNATYPSSDVPCDATLTEKSFETDMNLNF

QNLSVMGLRILLLKVAGFNLLMTLRLWSS*
```

\>Beta V2 D2 J2.7 C2 (CASSPDWGAEYEQYF)
(SEQ ID NO: 19)

```
MGSIFLSCLAVCLLVAGPVDPKIIQKPKYLVAVTGSEKILICEQYLGHNAMYWYRQSAK

KPLEFMFSYSYQKLMDNQTASSRFQPQSSKKNHLDLQITALKPDDSATYFCASSPDWGA

EYEQYFGPGTRLTVLEDLRNVTPPKVSLFEPSKAEIANKQKATLVCLARGFFPDHVELS
```

-continued

WWVNGKEVHSGVSTDPQAYKESNYSYCLSSRLRVSATFWHNPRNHFRCQVQFHGLSE

EDKWPEGSPKPVTQNISAEAWGRADCGITSASYHQGVLSATILYEILLGKATLYAVLVS

GLVLMAMVKKKNS*

---

The invention claimed is:

1. An artificial T cell receptor which binds to claudin-18.2 (CLDN18.2) but not to CLDN18.1 and, when expressed by a T cell, mediates specific lysis of a cell expressing CLDN18.2 on its surface, the artificial T cell receptor comprising a binding domain for CLDN18.2, a transmembrane domain, an IgG1-derived spacer region which links the binding domain for CLDN18.2 to the transmembrane domain, a T cell signaling domain, and a co-stimulation domain, wherein the binding domain for CLDN18.2 comprises (i) an antibody heavy chain variable region (VH) comprising a set of VH complementarity-determining regions VHCDR1, VHCDR2 and VHCDR3: GYTFTSYW (VHCDR1), IYPSDSYT (VHCDR2), and TRSWRGNSFDY (VHCDR3) and (ii) an antibody light chain variable region (VL) comprising a set of VL complementarity-determining regions VHCDR1, VHCDR2 and VHCDR3: QSLLNSGNQKNY (VLCDR1), WAS (VLCDR2), and QNDYSYPFT (VLCDR3) and wherein the transmembrane domain and the co-stimulation domain comprise an amino acid sequence represented by SEQ ID NO: 39.

2. The artificial T cell receptor of claim 1, wherein the T cell signaling domain comprises an amino acid sequence represented by SEQ ID NO: 40.

3. The artificial T cell receptor of claim 1, wherein the IgG1-derived spacer region comprises an amino acid sequence represented by SEQ ID NO: 38.

4. The artificial T cell receptor of claim 1, further comprising a signal peptide.

5. The artificial T cell receptor of claim 4, wherein the signal peptide comprises an amino acid sequence represented by SEQ ID NO: 37.

6. The artificial T cell receptor of claim 1, wherein the VH comprises an amino acid sequence represented by SEQ ID NO: 23 and the VL comprises an amino acid sequence represented by SEQ ID NO: 30.

7. The artificial T cell receptor of claim 6, wherein the IgG1-derived spacer region comprises an amino acid sequence represented by SEQ ID NO: 38 and wherein the T cell signaling domain comprises an amino acid sequence represented by SEQ ID NO: 40.

8. The artificial T cell receptor of claim 1, wherein the artificial T cell receptor comprises an amino acid sequence having at least 95% sequence identity to the amino acid sequence of SEQ ID NO: 41.

9. The artificial T cell receptor of claim 1, wherein the artificial T cell receptor comprises an amino acid sequence having at least 99% sequence identity to the amino acid sequence of SEQ ID NO: 41.

10. A T cell comprising the artificial T cell receptor of claim 1.

11. A plurality of T cells comprising the artificial T cell receptor of claim 1, wherein said plurality of T cells are activated and proliferate when exposed to CLDN18.2 in vivo.

12. A method for treating a patient having cancer characterized by cancer cells expressing CLDN18.2, the method comprising administering to the patient the plurality of T cells of claim 11.

13. A method for expanding the plurality of T cells of claim 11, the method comprising contacting the plurality of T cells with CLDN18.2.

14. The method of claim 13, wherein said contacting occurs in vivo.

15. The method of claim 13, wherein the method does not require providing exogenous IL-2.

16. A T cell comprising the artificial T cell receptor of claim 8.

17. A plurality of T cells comprising the artificial T cell receptor of claim 8, wherein said plurality of T cells are activated and proliferate when exposed to CLDN18.2 in vivo.

18. A method for treating a patient having cancer characterized by cancer cells expressing CLDN18.2, the method comprising administering to the patient the plurality of T cells of claim 17.

19. A method for expanding the plurality of T cells of claim 17, the method comprising contacting the plurality of T cells with CLDN18.2.

20. The method of claim 19, wherein said contacting occurs in vivo.

21. The method of claim 19, wherein the method does not require providing exogenous IL-2.

22. An artificial T cell receptor which binds to claudin-18.2 (CLDN18.2) but not to CLDN18.1 and, when expressed by a T cell, mediates specific lysis of a cell expressing CLDN18.2 on its surface, the artificial T cell receptor comprising a binding domain for CLDN18.2, a transmembrane domain, an IgG1-derived spacer region which links the binding domain for CLDN18.2 to the transmembrane domain, a T cell signaling domain, and a co-stimulation domain, wherein the binding domain for CLDN18.2 comprises (i) an antibody heavy chain variable region (VH) comprising a set of VH complementarity-determining regions VHCDR1, VHCDR2 and VHCDR3: GYTFTSYW (VHCDR1), IYPSDSYT (VHCDR2), and TRSWRGNSFDY (VHCDR3) and (ii) an antibody light chain variable region (VL) comprising a set of VL complementarity-determining regions VHCDR1, VHCDR2 and VHCDR3: QSLLNSGNQKNY (VLCDR1), WAS (VLCDR2), and QNDYSYPFT (VLCDR3).

23. The artificial T cell receptor of claim 22, wherein the IgG1-derived spacer region comprises an amino acid sequence represented by SEQ ID NO: 38.

24. The artificial T cell receptor of claim 22, wherein the transmembrane domain and the co-stimulation domain comprise an amino acid sequence represented by SEQ ID NO: 39.

25. The artificial T cell receptor of claim 22, wherein the T cell signaling domain comprises an amino acid sequence represented by SEQ ID NO: 40.

26. The artificial T cell receptor of claim 22, wherein the transmembrane domain and the co-stimulation domain comprise an amino acid sequence represented by SEQ ID NO: 39 and wherein the T cell signaling domain comprises an amino acid sequence represented by SEQ ID NO: 40.

27. A T cell comprising the artificial T cell receptor of claim 22.

28. A plurality of T cells comprising the artificial T cell receptor of claim 22, wherein said plurality of T cells are activated and proliferate when exposed to CLDN18.2 in vivo.

* * * * *

SEQUENCE LISTING

<160> NUMBER OF SEQ ID NOS: 47

<210> SEQ ID NO 1
<211> LENGTH: 261
<212> TYPE: PRT
<213> ORGANISM: Homo sapiens

<400> SEQUENCE: 1

```
Met Ala Val Thr Ala Cys Gln Gly Leu Gly Phe Val Val Ser Leu Ile
1               5                   10                  15

Gly Ile Ala Gly Ile Ile Ala Ala Thr Cys Met Asp Gln Trp Ser Thr
            20                  25                  30

Gln Asp Leu Tyr Asn Asn Pro Val Thr Ala Val Phe Asn Tyr Gln Gly
        35                  40                  45

Leu Trp Arg Ser Cys Val Arg Glu Ser Ser Gly Phe Thr Glu Cys Arg
    50                  55                  60

Gly Tyr Phe Thr Leu Leu Gly Leu Pro Ala Met Leu Gln Ala Val Arg
65                  70                  75                  80

Ala Leu Met Ile Val Gly Ile Val Leu Gly Ala Ile Gly Leu Leu Val
                85                  90                  95

Ser Ile Phe Ala Leu Lys Cys Ile Arg Ile Gly Ser Met Glu Asp Ser
            100                 105                 110

Ala Lys Ala Asn Met Thr Leu Thr Ser Gly Ile Met Phe Ile Val Ser
        115                 120                 125

Gly Leu Cys Ala Ile Ala Gly Val Ser Val Phe Ala Asn Met Leu Val
    130                 135                 140

Thr Asn Phe Trp Met Ser Thr Ala Asn Met Tyr Thr Gly Met Gly Gly
145                 150                 155                 160

Met Val Gln Thr Val Gln Thr Arg Tyr Thr Phe Gly Ala Ala Leu Phe
                165                 170                 175

Val Gly Trp Val Ala Gly Gly Leu Thr Leu Ile Gly Gly Val Met Met
            180                 185                 190

Cys Ile Ala Cys Arg Gly Leu Ala Pro Glu Glu Thr Asn Tyr Lys Ala
        195                 200                 205

Val Ser Tyr His Ala Ser Gly His Ser Val Ala Tyr Lys Pro Gly Gly
    210                 215                 220

Phe Lys Ala Ser Thr Gly Phe Gly Ser Asn Thr Lys Asn Lys Lys Ile
225                 230                 235                 240

Tyr Asp Gly Gly Ala Arg Thr Glu Asp Glu Val Gln Ser Tyr Pro Ser
                245                 250                 255

Lys His Asp Tyr Val
            260
```

<210> SEQ ID NO 2
<211> LENGTH: 9
<212> TYPE: PRT
<213> ORGANISM: Artificial Sequence
<220> FEATURE:
<223> OTHER INFORMATION: T cell epitope

```
<400> SEQUENCE: 2

Thr Leu Leu Gly Leu Pro Ala Met Leu
1               5

<210> SEQ ID NO 3
<211> LENGTH: 9
<212> TYPE: PRT
<213> ORGANISM: Artificial Sequence
<220> FEATURE:
<223> OTHER INFORMATION: T cell epitope

<400> SEQUENCE: 3

Gly Leu Pro Ala Met Leu Gln Ala Val
1               5

<210> SEQ ID NO 4
<211> LENGTH: 9
<212> TYPE: PRT
<213> ORGANISM: Artificial Sequence
<220> FEATURE:
<223> OTHER INFORMATION: T cell epitope

<400> SEQUENCE: 4

Ser Leu Ile Gly Ile Ala Gly Ile Ile
1               5

<210> SEQ ID NO 5
<211> LENGTH: 9
<212> TYPE: PRT
<213> ORGANISM: Artificial Sequence
<220> FEATURE:
<223> OTHER INFORMATION: T cell epitope

<400> SEQUENCE: 5

Gly Ile Ala Gly Ile Ile Ala Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: T cell epitope

<400> SEQUENCE: 6

Gln Gly Leu Gly Phe Val Val Ser Leu
1               5

<210> SEQ ID NO 7
<211> LENGTH: 9
<212> TYPE: PRT
<213> ORGANISM: Artificial Sequence
<220> FEATURE:
<223> OTHER INFORMATION: T cell epitope

<400> SEQUENCE: 7

Gly Leu Gly Phe Val Val Ser Leu Ile
1               5

<210> SEQ ID NO 8
<211> LENGTH: 268
<212> TYPE: PRT
<213> ORGANISM: Homo sapiens
```

<400> SEQUENCE: 8

```
Met Arg Pro Gly Thr Cys Ser Val Leu Val Leu Leu Met Leu Arg
1               5                   10                  15

Arg Ser Asn Gly Asp Ser Val Thr Gln Thr Glu Gly Leu Val Thr Val
            20                  25                  30

Thr Glu Gly Leu Pro Val Lys Leu Asn Cys Thr Tyr Gln Thr Thr Tyr
        35                  40                  45

Leu Thr Ile Ala Phe Phe Trp Tyr Val Gln Tyr Leu Asn Glu Ala Pro
    50                  55                  60

Gln Val Leu Leu Lys Ser Ser Thr Asp Asn Lys Arg Thr Glu His Gln
65                  70                  75                  80

Gly Phe His Ala Thr Leu His Lys Ser Ser Ser Phe His Leu Gln
                85                  90                  95

Lys Ser Ser Ala Gln Leu Ser Asp Ser Ala Leu Tyr Tyr Cys Ala Leu
            100                 105                 110

Met Asp Ser Asn Tyr Gln Leu Ile Trp Gly Ser Gly Thr Lys Leu Ile
        115                 120                 125

Ile Lys Pro Asp Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 9
<211> LENGTH: 301
<212> TYPE: PRT
<213> ORGANISM: Homo sapiens

<400> SEQUENCE: 9

```
Met Gly Ser Arg Leu Phe Phe Val Val Leu Ile Leu Leu Cys Ala Lys
1               5                   10                  15

His Met Glu Ala Ala Val Thr Gln Ser Pro Arg Ser Lys Val Ala Val
            20                  25                  30

Thr Gly Gly Lys Val Thr Leu Ser Cys His Gln Thr Asn Asn His Asp
        35                  40                  45

Tyr Met Tyr Trp Tyr Arg Gln Asp Thr Gly His Gly Leu Arg Leu Ile
    50                  55                  60

His Tyr Ser Tyr Val Ala Asp Ser Thr Glu Lys Gly Asp Ile Pro Asp
65                  70                  75                  80

Gly Tyr Lys Ala Ser Arg Pro Ser Gln Glu Asn Phe Ser Leu Ile Leu
                85                  90                  95
```

```
Glu Leu Ala Ser Leu Ser Gln Thr Ala Val Tyr Phe Cys Ala Ser Ser
                100                 105                 110

Ile Asn Glu Arg Leu Phe Phe Gly His Gly Thr Lys Leu Ser Val Leu
            115                 120                 125

Glu Asp Leu Arg Asn Val Thr Pro Pro Lys Val Ser Leu Phe Glu Pro
        130                 135                 140

Ser Lys Ala Glu Ile Ala Asn Lys Gln Lys Ala Thr Leu Val Cys Leu
145                 150                 155                 160

Ala Arg Gly Phe Phe Pro Asp His Val Glu Leu Ser Trp Trp Val Asn
                165                 170                 175

Gly Lys Glu Val His Ser Gly Val Ser Thr Asp Pro Gln Ala Tyr Lys
            180                 185                 190

Glu Ser Asn Tyr Ser Tyr Cys Leu Ser Ser Arg Leu Arg Val Ser Ala
        195                 200                 205

Thr Phe Trp His Asn Pro Arg Asn His Phe Arg Cys Gln Val Gln Phe
210                 215                 220

His Gly Leu Ser Glu Glu Asp Lys Trp Pro Glu Gly Ser Pro Lys Pro
225                 230                 235                 240

Val Thr Gln Asn Ile Ser Ala Glu Ala Trp Gly Arg Ala Asp Cys Gly
                245                 250                 255

Ile Thr Ser Ala Ser Tyr Gln Gln Gly Val Leu Ser Ala Thr Ile Leu
            260                 265                 270

Tyr Glu Ile Leu Leu Gly Lys Ala Thr Leu Tyr Ala Val Leu Val Ser
        275                 280                 285

Thr Leu Val Val Met Ala Met Val Lys Arg Lys Asn Ser
290                 295                 300

<210> SEQ ID NO 10
<211> LENGTH: 267
<212> TYPE: PRT
<213> ORGANISM: Homo sapiens

<400> SEQUENCE: 10

Met Asn Ser Phe Pro Gly Phe Met Thr Val Met Leu Leu Ile Phe Thr
1               5                   10                  15

Arg Ala His Gly Asp Ser Val Thr Gln Thr Glu Gly Gln Val Ala Leu
                20                  25                  30

Ser Glu Glu Asp Phe Leu Thr Ile His Cys Asn Tyr Ser Ala Ser Gly
            35                  40                  45

Tyr Pro Ala Leu Phe Trp Tyr Val Gln Tyr Pro Gly Glu Gly Pro Gln
        50                  55                  60

Phe Leu Phe Arg Ala Ser Arg Asp Lys Glu Lys Gly Ser Ser Arg Gly
65                  70                  75                  80

Phe Glu Ala Thr Tyr Asp Lys Gly Thr Thr Ser Phe His Leu Arg Lys
                85                  90                  95

Ala Ser Val Gln Glu Ser Asp Ser Ala Val Tyr Tyr Cys Ala Leu Gly
            100                 105                 110

Asp Tyr Ala Gln Gly Leu Thr Phe Gly Leu Gly Thr Arg Val Ser Val
        115                 120                 125

Phe Pro Tyr Ile Gln Asn Pro Glu Pro Ala Val Tyr Gln Leu Lys Asp
130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175
```

```
Lys Thr Val Leu Asp Met Lys Ala Met Asp Ser Lys Ser Asn Gly Ala
                180                 185                 190

Ile Ala Trp Ser Asn Gln Thr Ser Phe Thr Cys Gln Asp Ile Phe Lys
            195                 200                 205

Glu Thr Asn Ala Thr Tyr Pro Ser Ser Asp Val Pro Cys Asp Ala Thr
        210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Lys Val Ala Gly Phe
                245                 250                 255

Asn Leu Leu Met Thr Leu Arg Leu Trp Ser Ser
                260                 265
```

<210> SEQ ID NO 11
<211> LENGTH: 305
<212> TYPE: PRT
<213> ORGANISM: Homo sapiens

<400> SEQUENCE: 11

```
Met Gly Ser Ile Phe Leu Ser Cys Leu Ala Val Cys Leu Leu Val Ala
1               5                   10                  15

Gly Pro Val Asp Pro Lys Ile Ile Gln Lys Pro Lys Tyr Leu Val Ala
                20                  25                  30

Val Thr Gly Ser Glu Lys Ile Leu Ile Cys Glu Gln Tyr Leu Gly His
            35                  40                  45

Asn Ala Met Tyr Trp Tyr Arg Gln Ser Ala Lys Lys Pro Leu Glu Phe
        50                  55                  60

Met Phe Ser Tyr Ser Tyr Gln Lys Leu Met Asp Asn Gln Thr Ala Ser
65                  70                  75                  80

Ser Arg Phe Gln Pro Gln Ser Ser Lys Lys Asn His Leu Asp Leu Gln
                85                  90                  95

Ile Thr Ala Leu Lys Pro Asp Asp Ser Ala Thr Tyr Phe Cys Ala Ser
                100                 105                 110

Ser Gln Glu Trp Gly Gly Tyr Glu Gln Tyr Phe Gly Pro Gly Thr Arg
            115                 120                 125

Leu Thr Val Leu Glu Asp Leu Arg Asn Val Thr Pro Pro Lys Val Ser
        130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
                180                 185                 190

Gln Ala Tyr Lys Glu Ser Asn Tyr Ser Tyr Cys Leu Ser Ser Arg Leu
            195                 200                 205

Arg Val Ser Ala Thr Phe Trp His Asn Pro Arg Asn His Phe Arg Cys
        210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
                260                 265                 270

Ala Thr Ile Leu Tyr Glu Ile Leu Leu Gly Lys Ala Thr Leu Tyr Ala
            275                 280                 285
```

Val Leu Val Ser Gly Leu Val Leu Met Ala Met Val Lys Lys Lys Asn
    290                 295                 300

Ser
305

<210> SEQ ID NO 12
<211> LENGTH: 268
<212> TYPE: PRT
<213> ORGANISM: Homo sapiens

<400> SEQUENCE: 12

Met Asp Ser Phe Pro Gly Phe Met Thr Val Met Leu Leu Ile Phe Thr
1               5                   10                  15

Arg Ala His Gly Asp Ser Val Thr Gln Thr Glu Gly Gln Val Ala Leu
            20                  25                  30

Ser Glu Glu Asp Phe Leu Thr Ile His Cys Asn Tyr Ser Ala Ser Gly
        35                  40                  45

Tyr Pro Thr Leu Phe Trp Tyr Val Gln Tyr Pro Gly Glu Gly Pro Gln
    50                  55                  60

Leu Leu Phe Arg Ala Ser Arg Asp Lys Glu Lys Gly Ser Ser Arg Gly
65                  70                  75                  80

Phe Glu Ala Thr Tyr Asp Lys Gly Thr Thr Ser Phe His Leu Arg Lys
                85                  90                  95

Ala Ser Val Gln Glu Ser Asp Ser Ala Val Tyr Tyr Cys Ala Leu Ser
            100                 105                 110

Val Asp Tyr Ala Asn Lys Met Ile Phe Gly Leu Gly Thr Ile Leu Arg
        115                 120                 125

Val Arg Pro His Ile Gln Asn Pro Glu Pro Ala Val Tyr Gln Leu Lys
    130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
            180                 185                 190

Ala Ile Ala Trp Ser Asn Gln Thr Ser Phe Thr Cys Gln Asp Ile Phe
        195                 200                 205

Lys Glu Thr Asn Ala Thr Tyr Pro Ser Ser Asp Val Pro Cys Asp Ala
    210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265

<210> SEQ ID NO 13
<211> LENGTH: 307
<212> TYPE: PRT
<213> ORGANISM: Homo sapiens

<400> SEQUENCE: 13

Met Trp Gln Phe Cys Ile Leu Cys Leu Cys Val Leu Met Ala Ser Val
1               5                   10                  15

Ala Thr Asp Pro Thr Val Thr Leu Leu Glu Gln Asn Pro Arg Trp Arg
            20                  25                  30

```
Leu Val Pro Arg Gly Gln Ala Val Asn Leu Arg Cys Ile Leu Lys Asn
             35                  40                  45

Ser Gln Tyr Pro Trp Met Ser Trp Tyr Gln Asp Leu Gln Lys Gln
 50                  55                  60

Leu Gln Trp Leu Phe Thr Leu Arg Ser Pro Gly Asp Lys Glu Val Lys
 65                  70                  75                  80

Ser Leu Pro Gly Ala Asp Tyr Leu Ala Thr Arg Val Thr Asp Thr Glu
                 85                  90                  95

Leu Arg Leu Gln Val Ala Asn Met Ser Gln Gly Arg Thr Leu Tyr Cys
                100                 105                 110

Thr Cys Ser Pro Leu Thr Gly Ser Tyr Glu Gln Tyr Phe Gly Pro Gly
             115                 120                 125

Thr Arg Leu Thr Val Leu Glu Asp Leu Arg Asn Val Thr Pro Pro Lys
             130                 135                 140

Val Ser Leu Phe Glu Pro Ser Lys Ala Glu Ile Ala Asn Lys Gln Lys
145                 150                 155                 160

Ala Thr Leu Val Cys Leu Ala Arg Gly Phe Phe Pro Asp His Val Glu
                165                 170                 175

Leu Ser Trp Trp Val Asn Gly Lys Glu Val His Ser Gly Val Ser Thr
            180                 185                 190

Asp Pro Gln Ala Tyr Lys Glu Ser Asn Tyr Ser Tyr Cys Leu Ser Ser
            195                 200                 205

Arg Leu Arg Val Ser Ala Thr Phe Trp His Asn Pro Arg Asn His Phe
    210                 215                 220

Arg Cys Gln Val Gln Phe His Gly Leu Ser Glu Glu Asp Lys Trp Pro
225                 230                 235                 240

Glu Gly Ser Pro Lys Pro Val Thr Gln Asn Ile Ser Ala Glu Ala Trp
                245                 250                 255

Gly Arg Ala Asp Cys Gly Ile Thr Ser Ala Ser Tyr His Gln Gly Val
                260                 265                 270

Leu Ser Ala Thr Ile Leu Tyr Glu Ile Leu Leu Gly Lys Ala Thr Leu
            275                 280                 285

Tyr Ala Val Leu Val Ser Gly Leu Val Leu Met Ala Met Val Lys Lys
    290                 295                 300

Lys Asn Ser
305

<210> SEQ ID NO 14
<211> LENGTH: 264
<212> TYPE: PRT
<213> ORGANISM: Homo sapiens

<400> SEQUENCE: 14

Met Asn Arg Phe Leu Gly Ile Ser Leu Val Thr Leu Trp Phe Gln Val
 1               5                  10                  15

Ala Trp Ala Lys Ser Gln Trp Gly Glu Glu Asn Leu Gln Ala Leu Ser
                 20                  25                  30

Ile Gln Glu Gly Glu Asp Val Thr Met Asn Cys Ser Tyr Lys Thr Tyr
             35                  40                  45

Thr Thr Val Val Gln Trp Tyr Arg Gln Lys Ser Gly Lys Gly Pro Ala
         50                  55                  60

Gln Leu Ile Leu Ile Arg Ser Asn Glu Arg Glu Lys Arg Ser Gly Arg
 65                  70                  75                  80

Leu Arg Ala Thr Leu Asp Thr Ser Ser Gln Ser Ser Leu Ser Ile
                 85                  90                  95
```

```
Thr Gly Thr Leu Ala Thr Asp Thr Ala Val Tyr Phe Cys Ala Thr Asp
            100                 105                 110

Asn Arg Ile Phe Phe Gly Asp Gly Thr Gln Leu Val Val Lys Pro Asn
            115                 120                 125

Ile Gln Asn Pro Glu Pro Ala Val Tyr Gln Leu Lys Asp Pro Arg Ser
            130                 135                 140

Gln Asp Ser Thr Leu Cys Leu Phe Thr Asp Phe Asp Ser Gln Ile Asn
145                 150                 155                 160

Val Pro Lys Thr Met Glu Ser Gly Thr Phe Ile Thr Asp Lys Thr Val
            165                 170                 175

Leu Asp Met Lys Ala Met Asp Ser Lys Ser Asn Gly Ala Ile Ala Trp
            180                 185                 190

Ser Asn Gln Thr Ser Phe Thr Cys Gln Asp Ile Phe Lys Glu Thr Asn
            195                 200                 205

Ala Thr Tyr Pro Ser Ser Asp Val Pro Cys Asp Ala Thr Leu Thr Glu
            210                 215                 220

Lys Ser Phe Glu Thr Asp Met Asn Leu Asn Phe Gln Asn Leu Ser Val
225                 230                 235                 240

Met Gly Leu Arg Ile Leu Leu Leu Lys Val Ala Gly Phe Asn Leu Leu
            245                 250                 255

Met Thr Leu Arg Leu Trp Ser Ser
            260

<210> SEQ ID NO 15
<211> LENGTH: 305
<212> TYPE: PRT
<213> ORGANISM: Homo sapiens

<400> SEQUENCE: 15

Met Gly Ala Arg Leu Ile Cys Tyr Val Ala Leu Cys Leu Leu Gly Ala
1               5                   10                  15

Gly Ser Phe Asp Ala Ala Val Thr Gln Lys Pro Arg Tyr Leu Ile Lys
            20                  25                  30

Met Lys Gly Gln Glu Ala Glu Met Lys Cys Ile Pro Glu Lys Gly His
            35                  40                  45

Thr Ala Val Phe Trp Tyr Gln Gln Lys Gln Ser Lys Glu Leu Lys Phe
        50                  55                  60

Leu Ile Tyr Phe Gln Asn Gln Gln Pro Leu Asp Gln Ile Asp Met Val
65                  70                  75                  80

Lys Glu Arg Phe Ser Ala Val Cys Pro Ser Ser Ser Leu Cys Ser Leu
            85                  90                  95

Gly Ile Arg Thr Cys Glu Ala Glu Asp Ser Ala Leu Tyr Leu Cys Ser
            100                 105                 110

Ser Ser Gln Ser Gly Gly Tyr Glu Gln Tyr Phe Gly Pro Gly Thr Arg
            115                 120                 125

Leu Thr Val Leu Glu Asp Leu Arg Asn Val Thr Pro Pro Lys Val Ser
            130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
            165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
            195                 200                 205
```

```
Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Gly Lys Ala Thr Leu Tyr Ala
        275                 280                 285

Val Leu Val Ser Gly Leu Val Leu Met Ala Met Val Lys Lys Lys Asn
290                 295                 300

Ser
305

<210> SEQ ID NO 16
<211> LENGTH: 268
<212> TYPE: PRT
<213> ORGANISM: Homo sapiens

<400> SEQUENCE: 16

Met Leu Leu Ala Leu Leu Ser Val Leu Gly Ile His Phe Leu Leu Arg
1               5                   10                  15

Asp Ala Gln Ala Gln Ser Val Thr Gln Pro Asp Ala Arg Val Thr Val
                20                  25                  30

Ser Glu Gly Ala Ser Leu Gln Leu Arg Cys Lys Tyr Ser Tyr Phe Gly
            35                  40                  45

Thr Pro Tyr Leu Phe Trp Tyr Val Gln Tyr Pro Arg Gln Gly Leu Gln
50                  55                  60

Leu Leu Leu Lys Tyr Tyr Pro Gly Asp Pro Val Val Gln Gly Val Asn
65                  70                  75                  80

Gly Phe Glu Ala Glu Phe Ser Lys Ser Asn Ser Ser Phe His Leu Arg
                85                  90                  95

Lys Ala Ser Val His Trp Ser Asp Trp Ala Val Tyr Phe Cys Ala Val
                100                 105                 110

Ser Lys Tyr Tyr Asn Val Leu Tyr Phe Gly Ser Gly Thr Lys Leu Thr
            115                 120                 125

Val Glu Pro Asn Ile Gln Asn Pro Glu Pro Ala Val Tyr Gln Leu Lys
130                 135                 140

Asp Pro Arg Ser Gln Asp Ser Thr Leu Cys Leu Phe Thr Asp Phe Asp
145                 150                 155                 160

Ser Gln Ile Asn Val Pro Lys Thr Met Glu Ser Gly Thr Phe Ile Thr
                165                 170                 175

Asp Lys Thr Val Leu Asp Met Lys Ala Met Asp Ser Lys Ser Asn Gly
                180                 185                 190

Ala Ile Ala Trp Ser Asn Gln Thr Ser Phe Thr Cys Gln Asp Ile Phe
            195                 200                 205

Lys Glu Thr Asn Ala Thr Tyr Pro Ser Ser Asp Val Pro Cys Asp Ala
210                 215                 220

Thr Leu Thr Glu Lys Ser Phe Glu Thr Asp Met Asn Leu Asn Phe Gln
225                 230                 235                 240

Asn Leu Ser Val Met Gly Leu Arg Ile Leu Leu Leu Lys Val Ala Gly
                245                 250                 255

Phe Asn Leu Leu Met Thr Leu Arg Leu Trp Ser Ser
            260                 265
```

<210> SEQ ID NO 17
<211> LENGTH: 305
<212> TYPE: PRT
<213> ORGANISM: Homo sapiens

<400> SEQUENCE: 17

Met Gly Ser Ile Phe Leu Ser Cys Leu Ala Val Cys Leu Leu Val Ala
1               5                   10                  15

Gly Pro Val Asp Pro Lys Ile Ile Gln Lys Pro Lys Tyr Leu Val Ala
            20                  25                  30

Val Thr Gly Ser Glu Lys Ile Leu Ile Cys Glu Gln Tyr Leu Gly His
        35                  40                  45

Asn Ala Met Tyr Trp Tyr Arg Gln Ser Ala Lys Lys Pro Leu Glu Phe
    50                  55                  60

Met Phe Ser Tyr Ser Tyr Gln Lys Leu Met Asp Asn Gln Thr Ala Ser
65                  70                  75                  80

Ser Arg Phe Gln Pro Gln Ser Ser Lys Lys Asn His Leu Asp Leu Gln
                85                  90                  95

Ile Thr Ala Leu Lys Pro Asp Asp Ser Ala Thr Tyr Phe Cys Ala Ser
            100                 105                 110

Ser Gln Asp Gln Gly Gly Gln Gly Gln Tyr Phe Gly Pro Gly Thr Arg
        115                 120                 125

Leu Thr Val Leu Glu Asp Leu Arg Asn Val Thr Pro Pro Lys Val Ser
    130                 135                 140

Leu Phe Glu Pro Ser Lys Ala Glu Ile Ala Asn Lys Gln Lys Ala Thr
145                 150                 155                 160

Leu Val Cys Leu Ala Arg Gly Phe Phe Pro Asp His Val Glu Leu Ser
                165                 170                 175

Trp Trp Val Asn Gly Lys Glu Val His Ser Gly Val Ser Thr Asp Pro
            180                 185                 190

Gln Ala Tyr Lys Glu Ser Asn Tyr Ser Tyr Cys Leu Ser Ser Arg Leu
        195                 200                 205

Arg Val Ser Ala Thr Phe Trp His Asn Pro Arg Asn His Phe Arg Cys
    210                 215                 220

Gln Val Gln Phe His Gly Leu Ser Glu Glu Asp Lys Trp Pro Glu Gly
225                 230                 235                 240

Ser Pro Lys Pro Val Thr Gln Asn Ile Ser Ala Glu Ala Trp Gly Arg
                245                 250                 255

Ala Asp Cys Gly Ile Thr Ser Ala Ser Tyr His Gln Gly Val Leu Ser
            260                 265                 270

Ala Thr Ile Leu Tyr Glu Ile Leu Leu Gly Lys Ala Thr Leu Tyr Ala
        275                 280                 285

Val Leu Val Ser Gly Leu Val Leu Met Ala Met Val Lys Lys Lys Asn
    290                 295                 300

Ser
305

<210> SEQ ID NO 18
<211> LENGTH: 267
<212> TYPE: PRT
<213> ORGANISM: Homo sapiens

<400> SEQUENCE: 18

```
Met Asn Thr Ser Pro Ala Leu Val Thr Val Met Leu Phe Ile Leu Gly
1               5                   10                  15

Arg Thr His Gly Asp Ser Val Ile Gln Met Gln Gly Gln Val Thr Leu
            20                  25                  30

Ser Glu Asn Asp Phe Leu Phe Ile Asn Cys Thr Tyr Ser Thr Thr Gly
        35                  40                  45

Tyr Pro Thr Leu Phe Trp Tyr Val Gln Tyr Ser Gly Glu Gly Pro Gln
    50                  55                  60

Leu Leu Leu Gln Val Thr Thr Ala Asn Asn Lys Gly Ser Ser Arg Gly
65                  70                  75                  80

Phe Glu Ala Thr Tyr Asp Lys Gly Thr Thr Ser Phe His Leu Gln Lys
                85                  90                  95

Thr Ser Val Gln Glu Ile Asp Ser Ala Val Tyr Tyr Cys Ala Ile Gly
            100                 105                 110

Asn Tyr Ala Gln Gly Leu Thr Phe Gly Leu Gly Thr Arg Val Ser Val
        115                 120                 125

Phe Pro Tyr Ile Gln Asn Pro Glu Pro Ala Val Tyr Gln Leu Lys Asp
    130                 135                 140

Pro Arg Ser Gln Asp Ser Thr Leu Cys Leu Phe Thr Asp Phe Asp Ser
145                 150                 155                 160

Gln Ile Asn Val Pro Lys Thr Met Glu Ser Gly Thr Phe Ile Thr Asp
                165                 170                 175

Lys Thr Val Leu Asp Met Lys Ala Met Asp Ser Lys Ser Asn Gly Ala
            180                 185                 190

Ile Ala Trp Ser Asn Gln Thr Ser Phe Thr Cys Gln Asp Ile Phe Lys
        195                 200                 205

Glu Thr Asn Ala Thr Tyr Pro Ser Ser Asp Val Pro Cys Asp Ala Thr
    210                 215                 220

Leu Thr Glu Lys Ser Phe Glu Thr Asp Met Asn Leu Asn Phe Gln Asn
225                 230                 235                 240

Leu Ser Val Met Gly Leu Arg Ile Leu Leu Leu Lys Val Ala Gly Phe
                245                 250                 255

Asn Leu Leu Met Thr Leu Arg Leu Trp Ser Ser
            260                 265
```

<210> SEQ ID NO 19
<211> LENGTH: 306
<212> TYPE: PRT
<213> ORGANISM: Homo sapiens

<400> SEQUENCE: 19

```
Met Gly Ser Ile Phe Leu Ser Cys Leu Ala Val Cys Leu Leu Val Ala
1               5                   10                  15

Gly Pro Val Asp Pro Lys Ile Ile Gln Lys Pro Lys Tyr Leu Val Ala
            20                  25                  30

Val Thr Gly Ser Glu Lys Ile Leu Ile Cys Glu Gln Tyr Leu Gly His
        35                  40                  45

Asn Ala Met Tyr Trp Tyr Arg Gln Ser Ala Lys Lys Pro Leu Glu Phe
    50                  55                  60

Met Phe Ser Tyr Ser Tyr Gln Lys Leu Met Asp Asn Gln Thr Ala Ser
65                  70                  75                  80

Ser Arg Phe Gln Pro Gln Ser Ser Lys Lys Asn His Leu Asp Leu Gln
                85                  90                  95
```

```
Ile Thr Ala Leu Lys Pro Asp Asp Ser Ala Thr Tyr Phe Cys Ala Ser
            100                 105                 110

Ser Pro Asp Trp Gly Ala Glu Tyr Glu Gln Tyr Phe Gly Pro Gly Thr
            115                 120                 125

Arg Leu Thr Val Leu Glu Asp Leu Arg Asn Val Thr Pro Pro Lys Val
            130                 135                 140

Ser Leu Phe Glu Pro Ser Lys Ala Glu Ile Ala Asn Lys Gln Lys Ala
145                 150                 155                 160

Thr Leu Val Cys Leu Ala Arg Gly Phe Phe Pro Asp His Val Glu Leu
                165                 170                 175

Ser Trp Trp Val Asn Gly Lys Glu Val His Ser Gly Val Ser Thr Asp
            180                 185                 190

Pro Gln Ala Tyr Lys Glu Ser Asn Tyr Ser Tyr Cys Leu Ser Ser Arg
            195                 200                 205

Leu Arg Val Ser Ala Thr Phe Trp His Asn Pro Arg Asn His Phe Arg
            210                 215                 220

Cys Gln Val Gln Phe His Gly Leu Ser Glu Glu Asp Lys Trp Pro Glu
225                 230                 235                 240

Gly Ser Pro Lys Pro Val Thr Gln Asn Ile Ser Ala Glu Ala Trp Gly
                245                 250                 255

Arg Ala Asp Cys Gly Ile Thr Ser Ala Ser Tyr His Gln Gly Val Leu
                260                 265                 270

Ser Ala Thr Ile Leu Tyr Glu Ile Leu Leu Gly Lys Ala Thr Leu Tyr
            275                 280                 285

Ala Val Leu Val Ser Gly Leu Val Leu Met Ala Met Val Lys Lys Lys
            290                 295                 300

Asn Ser
305

<210> SEQ ID NO 20
<211> LENGTH: 117
<212> TYPE: PRT
<213> ORGANISM: Artificial Sequence
<220> FEATURE:
<223> OTHER INFORMATION: Antibody fragment

<400> SEQUENCE: 20

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Asp Tyr Pro Trp Phe Ala Tyr Trp Gly Gln Gly Thr Leu
            100                 105                 110

Val Thr Val Ser Ala
            115
```

<210> SEQ ID NO 21
<211> LENGTH: 118
<212> TYPE: PRT
<213> ORGANISM: Artificial Sequence
<220> FEATURE:
<223> OTHER INFORMATION: Antibody fragment

<400> SEQUENCE: 21

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
                20                  25                  30

Gly Met Asn Trp Val Lys Gln Ala Pro Gly Lys Gly Leu Lys Trp Met
            35                  40                  45

Gly Trp Ile Asn Thr Asn Thr Gly Glu Pro Thr Tyr Ala Glu Glu Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Leu Gly Phe Gly Asn Ala Met Asp Tyr Trp Gly Gln Gly Thr
            100                 105                 110

Ser Val Thr Val Ser Ser
        115

<210> SEQ ID NO 22
<211> LENGTH: 116
<212> TYPE: PRT
<213> ORGANISM: Artificial Sequence
<220> FEATURE:
<223> OTHER INFORMATION: Antibody fragment

<400> SEQUENCE: 22

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Asp Tyr
                20                  25                  30

Tyr Ile Asn Trp Val Lys Gln Arg Thr Gly Gln Gly Leu Glu Trp Ile
            35                  40                  45

Gly Glu Ile Tyr Pro Gly Ser Gly Asn Thr Tyr Tyr Asn Glu Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Ser Tyr Gly Ala Phe Asp Tyr Trp Gly Gln Gly Thr Thr Leu
            100                 105                 110

Thr Val Ser Ser
        115

<210> SEQ ID NO 23
<211> LENGTH: 118
<212> TYPE: PRT
<213> ORGANISM: Artificial Sequence
<220> FEATURE:
<223> OTHER INFORMATION: Antibody fragment

```
<400> SEQUENCE: 23

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser
            115

<210> SEQ ID NO 24
<211> LENGTH: 118
<212> TYPE: PRT
<213> ORGANISM: Artificial Sequence
<220> FEATURE:
<223> OTHER INFORMATION: Antibody fragment

<400> SEQUENCE: 24

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Val Ile Ser Trp Val Lys Gln Arg Thr Gly Gln Gly Leu Glu Trp Ile
        35                  40                  45

Gly Glu Ile Tyr Pro Gly Ser Gly Ser Thr Tyr Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Ser Ser Leu Thr Ser Glu Asp Ser Ala Val Tyr Phe Cys
                85                  90                  95

Ala Arg Gly Val Leu Leu Arg Ala Met Asp Tyr Trp Gly Gln Gly Thr
            100                 105                 110

Ser Val Thr Val Ser Ser
            115

<210> SEQ ID NO 25
<211> LENGTH: 120
<212> TYPE: PRT
<213> ORGANISM: Artificial Sequence
<220> FEATURE:
<223> OTHER INFORMATION: Antibody fragment

<400> SEQUENCE: 25

Gln Val His Leu Gln Gln Ser Gly Ser Glu Leu Arg Ser Pro Gly Ser
1               5                   10                  15

Ser Val Lys Leu Ser Cys Lys Asp Phe Asp Ser Glu Val Phe Pro Phe
            20                  25                  30

Ala Tyr Met Ser Trp Ile Arg Gln Lys Pro Gly His Gly Phe Glu Trp
        35                  40                  45
```

Ile Gly Asp Ile Leu Pro Ser Ile Gly Arg Thr Ile Tyr Gly Glu Lys
50              55                  60

Phe Glu Asp Lys Ala Thr Leu Asp Ala Asp Val Ser Asn Thr Ala
65              70                  75                  80

Tyr Leu Glu Leu Asn Ser Leu Thr Ser Glu Asp Ser Ala Ile Tyr Tyr
                85                  90                  95

Cys Ala Arg Gly Glu Gly Tyr Gly Ala Trp Phe Ala Tyr Trp Gly Gln
            100                 105                 110

Gly Thr Leu Val Thr Val Ser Ala
        115                 120

<210> SEQ ID NO 26
<211> LENGTH: 113
<212> TYPE: PRT
<213> ORGANISM: Artificial Sequence
<220> FEATURE:
<223> OTHER INFORMATION: Antibody fragment

<400> SEQUENCE: 26

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys

<210> SEQ ID NO 27
<211> LENGTH: 106
<212> TYPE: PRT
<213> ORGANISM: Artificial Sequence
<220> FEATURE:
<223> OTHER INFORMATION: Antibody fragment

<400> SEQUENCE: 27

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Pro Thr
                85                  90                  95

Phe Gly Gly Gly Thr Lys Leu Glu Ile Lys
            100                 105

-continued

```
<210> SEQ ID NO 28
<211> LENGTH: 107
<212> TYPE: PRT
<213> ORGANISM: Artificial Sequence
<220> FEATURE:
<223> OTHER INFORMATION: Antibody fragment

<400> SEQUENCE: 28

Asp Ile Val Met Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Gly Gly Thr Lys Leu Glu Ile Lys
            100                 105

<210> SEQ ID NO 29
<211> LENGTH: 113
<212> TYPE: PRT
<213> ORGANISM: Artificial Sequence
<220> FEATURE:
<223> OTHER INFORMATION: Antibody fragment

<400> SEQUENCE: 29

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 30
<211> LENGTH: 113
<212> TYPE: PRT
<213> ORGANISM: Artificial Sequence
<220> FEATURE:
<223> OTHER INFORMATION: Antibody fragment

<400> SEQUENCE: 30

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30
```

```
Gly Asn Gln Lys Asn Tyr Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
65                   70                  75                  80

Ile Ser Ser Val Gln Ala Glu Asp Leu Ala Val Tyr Tyr Cys Gln Asn
                 85                  90                  95

Asp Tyr Ser Tyr Pro Phe Thr Phe Gly Ser Gly Thr Lys Leu Glu Ile
                100                 105                 110

Lys
```

<210> SEQ ID NO 31
<211> LENGTH: 112
<212> TYPE: PRT
<213> ORGANISM: Artificial Sequence
<220> FEATURE:
<223> OTHER INFORMATION: Antibody fragment

<400> SEQUENCE: 31

```
Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
                20                  25                  30

Arg Thr Arg Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Gly Thr Asp Phe Thr Leu Thr
65                   70                  75                  80

Ile Ser Ser Val Gln Ala Glu Asp Leu Ala Val Tyr Tyr Cys Lys Gln
                 85                  90                  95

Ser Tyr Asn Leu Tyr Thr Phe Gly Gly Gly Thr Lys Leu Glu Ile Lys
                100                 105                 110
```

<210> SEQ ID NO 32
<211> LENGTH: 113
<212> TYPE: PRT
<213> ORGANISM: Artificial Sequence
<220> FEATURE:
<223> OTHER INFORMATION: Antibody fragment

<400> SEQUENCE: 32

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
 50                  55                  60

Pro Asp Arg Phe Thr Gly Ser Gly Ser Ala Thr Asp Phe Thr Leu Thr
65                   70                  75                  80

Ile Ser Ser Val Gln Ala Glu Asp Leu Ala Asp Tyr His Cys Gly Gln
                 85                  90                  95
```

```
Gly Tyr Ser Tyr Pro Tyr Thr Phe Gly Gly Gly Thr Lys Leu Glu Ile
                100                 105                 110
Lys

<210> SEQ ID NO 33
<211> LENGTH: 113
<212> TYPE: PRT
<213> ORGANISM: Artificial Sequence
<220> FEATURE:
<223> OTHER INFORMATION: Antibody fragment

<400> SEQUENCE: 33

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
                20                  25                  30

Ser Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys

<210> SEQ ID NO 34
<211> LENGTH: 107
<212> TYPE: PRT
<213> ORGANISM: Artificial Sequence
<220> FEATURE:
<223> OTHER INFORMATION: Antibody fragment

<400> SEQUENCE: 34

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Val Val Thr Tyr
                20                  25                  30

Val Ser Trp Tyr Gln Gln Lys Pro Glu Gln Ser Pro Lys Leu Leu Ile
            35                  40                  45

Tyr Gly Ala Ser Asn Arg Tyr Thr Gly Val Pro Asp Arg Phe Thr Gly
        50                  55                  60

Ser Gly Ser Ala Thr Asp Phe Thr Leu Thr Ile Ser Ser Val Lys Ala
65                  70                  75                  80

Glu Asp Leu Ala Val Tyr Tyr Cys Gln Gln Tyr Tyr Ser Tyr Pro Leu
                85                  90                  95

Thr Phe Gly Ala Gly Thr Lys Leu Glu Leu Lys
                100                 105

<210> SEQ ID NO 35
<211> LENGTH: 251
<212> TYPE: PRT
<213> ORGANISM: Artificial Sequence
<220> FEATURE:
<223> OTHER INFORMATION: mouse IgG Vh-Vl (kappa)
```

<400> SEQUENCE: 35

```
Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Val Lys Gln Arg Pro Gly Gln Gly Leu Glu Trp Ile
        35                  40                  45

Gly Asn Ile Tyr Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Thr Arg Ser Trp Arg Gly Asn Ser Phe Asp Tyr Trp Gly Gln Gly Thr
            100                 105                 110

Thr Leu Thr Val Ser Ser Gly Gly Gly Gly Ser Gly Gly Gly Gly Ser
        115                 120                 125

Gly Gly Gly Gly Ser Asp Ile Val Met Thr Gln Ser Pro Ser Ser Leu
    130                 135                 140

Thr Val Thr Ala Gly Glu Lys Val Thr Met Ser Cys Lys Ser Ser Gln
145                 150                 155                 160

Ser Leu Leu Asn Ser Gly Asn Gln Lys Asn Tyr Leu Thr Trp Tyr Gln
                165                 170                 175

Gln Lys Pro Gly Gln Pro Pro Lys Leu Leu Ile Tyr Trp Ala Ser Thr
            180                 185                 190

Arg Glu Ser Gly Val Pro Asp Arg Phe Thr Gly Ser Gly Ser Gly Thr
        195                 200                 205

Asp Phe Thr Leu Thr Ile Ser Ser Val Gln Ala Glu Asp Leu Ala Val
    210                 215                 220

Tyr Tyr Cys Gln Asn Asp Tyr Ser Tyr Pro Phe Thr Phe Gly Ser Gly
225                 230                 235                 240

Thr Lys Leu Glu Ile Lys Arg Ser Asp Pro Ala
                245                 250
```

<210> SEQ ID NO 36
<211> LENGTH: 15
<212> TYPE: PRT
<213> ORGANISM: Artificial Sequence
<220> FEATURE:
<223> OTHER INFORMATION: Linker

<400> SEQUENCE: 36

```
Gly Gly Gly Gly Ser Gly Gly Gly Gly Ser Gly Gly Gly Gly Ser
1               5                   10                  15
```

<210> SEQ ID NO 37
<211> LENGTH: 19
<212> TYPE: PRT
<213> ORGANISM: Artificial Sequence
<220> FEATURE:
<223> OTHER INFORMATION: Signal peptide

<400> SEQUENCE: 37

```
Met Asp Trp Ile Trp Arg Ile Leu Phe Leu Val Gly Ala Ala Thr Gly
1               5                   10                  15

Ala His Ser
```

```
<210> SEQ ID NO 38
<211> LENGTH: 231
<212> TYPE: PRT
<213> ORGANISM: Artificial Sequence
<220> FEATURE:
<223> OTHER INFORMATION: human IgG1 Fc fragment

<400> SEQUENCE: 38

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ala Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 39
<211> LENGTH: 68
<212> TYPE: PRT
<213> ORGANISM: Artificial Sequence
<220> FEATURE:
<223> OTHER INFORMATION: human CD28 (TM + ic)

<400> SEQUENCE: 39

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Ala Tyr Ala Ala Ala Arg Asp Phe Ala
    50                  55                  60

Ala Tyr Arg Ser
65
```

```
<210> SEQ ID NO 40
<211> LENGTH: 113
<212> TYPE: PRT
<213> ORGANISM: Artificial Sequence
<220> FEATURE:
<223> OTHER INFORMATION: human CD3-zeta (ic)

<400> SEQUENCE: 40

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 41
<211> LENGTH: 686
<212> TYPE: PRT
<213> ORGANISM: Artificial Sequence
<220> FEATURE:
<223> OTHER INFORMATION: Artificial T cell receptor

<400> SEQUENCE: 41

Met Asp Trp Ile Trp Arg Ile Leu Phe Leu Val Gly Ala Ala Thr Gly
1               5                   10                  15

Ala His Ser Gln Val Gln Leu Gln Gln Pro Gly Ala Glu Leu Val Arg
            20                  25                  30

Pro Gly Ala Ser Val Lys Leu Ser Cys Lys Ala Ser Gly Tyr Thr Phe
        35                  40                  45

Thr Ser Tyr Trp Ile Asn Trp Val Lys Gln Arg Pro Gly Gln Gly Leu
    50                  55                  60

Glu Trp Ile Gly Asn Ile Tyr Pro Ser Asp Ser Tyr Thr Asn Tyr Asn
65                  70                  75                  80

Gln Lys Phe Lys Asp Lys Ala Thr Leu Thr Val Asp Lys Ser Ser Ser
                85                  90                  95

Thr Ala Tyr Met Gln Leu Ser Ser Pro Thr Ser Glu Asp Ser Ala Val
            100                 105                 110

Tyr Tyr Cys Thr Arg Ser Trp Arg Gly Asn Ser Phe Asp Tyr Trp Gly
        115                 120                 125

Gln Gly Thr Thr Leu Thr Val Ser Ser Gly Gly Gly Gly Ser Gly Gly
    130                 135                 140

Gly Gly Ser Gly Gly Gly Gly Ser Asp Ile Val Met Thr Gln Ser Pro
145                 150                 155                 160

Ser Ser Leu Thr Val Thr Ala Gly Glu Lys Val Thr Met Ser Cys Lys
                165                 170                 175

Ser Ser Gln Ser Leu Leu Asn Ser Gly Asn Gln Lys Asn Tyr Leu Thr
            180                 185                 190
```

```
Trp Tyr Gln Gln Lys Pro Gly Gln Pro Pro Lys Leu Leu Ile Tyr Trp
            195                 200                 205
Ala Ser Thr Arg Glu Ser Gly Val Pro Asp Arg Phe Thr Gly Ser Gly
    210                 215                 220
Ser Gly Thr Asp Phe Thr Leu Thr Ile Ser Ser Val Gln Ala Glu Asp
225                 230                 235                 240
Leu Ala Val Tyr Tyr Cys Gln Asn Asp Tyr Ser Tyr Pro Phe Thr Phe
                245                 250                 255
Gly Ser Gly Thr Lys Leu Glu Ile Lys Arg Ser Asp Pro Ala Glu Pro
            260                 265                 270
Lys Ser Pro Asp Lys Thr His Thr Cys Pro Pro Cys Pro Ala Pro Pro
            275                 280                 285
Val Ala Gly Pro Ser Val Phe Leu Phe Pro Pro Lys Pro Lys Asp Thr
    290                 295                 300
Leu Met Ile Ala Arg Thr Pro Glu Val Thr Cys Val Val Val Asp Val
305                 310                 315                 320
Ser His Glu Asp Pro Glu Val Lys Phe Asn Trp Tyr Val Asp Gly Val
                325                 330                 335
Glu Val His Asn Ala Lys Thr Lys Pro Arg Glu Glu Gln Tyr Asn Ser
            340                 345                 350
Thr Tyr Arg Val Val Ser Val Leu Thr Val Leu His Gln Asp Trp Leu
            355                 360                 365
Asn Gly Lys Glu Tyr Lys Cys Lys Val Ser Asn Lys Ala Leu Pro Ala
            370                 375                 380
Pro Ile Glu Lys Thr Ile Ser Lys Ala Lys Gly Gln Pro Arg Glu Pro
385                 390                 395                 400
Gln Val Tyr Thr Leu Pro Pro Ser Arg Asp Glu Leu Thr Lys Asn Gln
                405                 410                 415
Val Ser Leu Thr Cys Leu Val Lys Gly Phe Tyr Pro Ser Asp Ile Ala
            420                 425                 430
Val Glu Trp Glu Ser Asn Gly Gln Pro Glu Asn Asn Tyr Lys Thr Thr
            435                 440                 445
Pro Pro Val Leu Asp Ser Asp Gly Ser Phe Phe Leu Tyr Ser Lys Leu
    450                 455                 460
Thr Val Asp Lys Ser Arg Trp Gln Gln Gly Asn Val Phe Ser Cys Ser
465                 470                 475                 480
Val Met His Glu Ala Leu His Asn His Tyr Thr Gln Lys Ser Leu Ser
                485                 490                 495
Leu Ser Pro Gly Lys Lys Asp Pro Lys Phe Trp Val Leu Val Val Val
            500                 505                 510
Gly Gly Val Leu Ala Cys Tyr Ser Leu Leu Val Thr Val Ala Phe Ile
            515                 520                 525
Ile Phe Trp Val Arg Ser Lys Arg Ser Arg Leu Leu His Ser Asp Tyr
            530                 535                 540
Met Asn Met Thr Pro Arg Arg Pro Gly Pro Thr Arg Lys His Tyr Gln
545                 550                 555                 560
Ala Tyr Ala Ala Ala Arg Asp Phe Ala Ala Tyr Arg Ser Leu Arg Val
                565                 570                 575
Lys Phe Ser Arg Ser Ala Asp Ala Pro Ala Tyr Gln Gln Gly Gln Asn
            580                 585                 590
Gln Leu Tyr Asn Glu Leu Asn Leu Gly Arg Arg Glu Glu Tyr Asp Val
            595                 600                 605
```

```
Leu Asp Lys Arg Arg Gly Arg Asp Pro Glu Met Gly Lys Pro Arg
    610                 615                 620

Arg Lys Asn Pro Gln Glu Gly Leu Tyr Asn Glu Leu Gln Lys Asp Lys
625                 630                 635                 640

Met Ala Glu Ala Tyr Ser Glu Ile Gly Met Lys Gly Glu Arg Arg Arg
                645                 650                 655

Gly Lys Gly His Asp Gly Leu Tyr Gln Gly Leu Ser Thr Ala Thr Lys
            660                 665                 670

Asp Thr Tyr Asp Ala Leu His Met Gln Ala Leu Pro Pro Arg
    675                 680                 685

<210> SEQ ID NO 42
<211> LENGTH: 8
<212> TYPE: PRT
<213> ORGANISM: Artificial Sequence
<220> FEATURE:
<223> OTHER INFORMATION: CDR sequence

<400> SEQUENCE: 42

Gly Tyr Thr Phe Thr Ser Tyr Trp
1               5

<210> SEQ ID NO 43
<211> LENGTH: 8
<212> TYPE: PRT
<213> ORGANISM: Artificial Sequence
<220> FEATURE:
<223> OTHER INFORMATION: CDR sequence

<400> SEQUENCE: 43

Ile Tyr Pro Ser Asp Ser Tyr Thr
1               5

<210> SEQ ID NO 44
<211> LENGTH: 11
<212> TYPE: PRT
<213> ORGANISM: Artificial Sequence
<220> FEATURE:
<223> OTHER INFORMATION: CDR sequence

<400> SEQUENCE: 44

Thr Arg Ser Trp Arg Gly Asn Ser Phe Asp Tyr
1               5                   10

<210> SEQ ID NO 45
<211> LENGTH: 12
<212> TYPE: PRT
<213> ORGANISM: Artificial Sequence
<220> FEATURE:
<223> OTHER INFORMATION: CDR sequence

<400> SEQUENCE: 45

Gln Ser Leu Leu Asn Ser Gly Asn Gln Lys Asn Tyr
1               5                   10

<210> SEQ ID NO 46
<211> LENGTH: 3
<212> TYPE: PRT
<213> ORGANISM: Artificial Sequence
<220> FEATURE:
<223> OTHER INFORMATION: CDR sequence

<400> SEQUENCE: 46

Trp Ala Ser
1
```

```
<210> SEQ ID NO 47
<211> LENGTH: 9
<212> TYPE: PRT
<213> ORGANISM: Artificial Sequence
<220> FEATURE:
<223> OTHER INFORMATION: CDR sequence

<400> SEQUENCE: 47

Gln Asn Asp Tyr Ser Tyr Pro Phe Thr
1               5
```